(12) United States Patent
Farha et al.

(10) Patent No.: US 11,530,404 B2
(45) Date of Patent: Dec. 20, 2022

(54) ENZYME IMMOBILIZATION IN HIERARCHICAL METAL-ORGANIC FRAMEWORKS

(71) Applicant: Northwestern University, Evanston, IL (US)

(72) Inventors: Omar K. Farha, Glenview, IL (US); Peng Li, Chicago, IL (US); Justin A. Modica, Chicago, IL (US); Milan Mrksich, Hinsdale, IL (US); Joseph T. Hupp, Northfield, IL (US)

(73) Assignee: Northwestern University, Evanston, IL (US)

( * ) Notice: Subject to any disclaimer, the term of this patent is extended or adjusted under 35 U.S.C. 154(b) by 314 days.

(21) Appl. No.: 16/306,563

(22) PCT Filed: May 25, 2017

(86) PCT No.: PCT/US2017/034416
§ 371 (c)(1),
(2) Date: Dec. 1, 2018

(87) PCT Pub. No.: WO2017/213871
PCT Pub. Date: Dec. 14, 2017

(65) Prior Publication Data
US 2019/0112591 A1    Apr. 18, 2019

Related U.S. Application Data

(60) Provisional application No. 62/345,656, filed on Jun. 3, 2016.

(51) Int. Cl.
*C12N 11/02* (2006.01)
*C12N 11/14* (2006.01)
(Continued)

(52) U.S. Cl.
CPC ............... *C12N 11/02* (2013.01); *A62D 3/02* (2013.01); *C12N 9/16* (2013.01); *C12N 9/18* (2013.01);
(Continued)

(58) Field of Classification Search
None
See application file for complete search history.

(56) References Cited

U.S. PATENT DOCUMENTS

2012/0130691 A1    5/2012  Li et al.
2015/0086413 A1    3/2015  Wolverton et al.
(Continued)

FOREIGN PATENT DOCUMENTS

WO    WO 2013/058844    4/2013
WO    WO 2015/183813    12/2015
(Continued)

OTHER PUBLICATIONS

Hill et al. Bioorganic Chemistry 29, 27-35 (2001).*
(Continued)

*Primary Examiner* — Clinton A Brooks

(57) ABSTRACT

Enzyme-immobilizing MOFs and methods for their use in enzymatically catalyzed reactions are provided. The MOFs are channel-type MOFs that present a hierarchical pore structure comprising a first set of large channels sized for enzyme immobilization and a second set of smaller channels running alongside of the large channels that remain enzyme-free and allow for reactant delivery to the enzymes and product expulsion from the larger channels.

18 Claims, 51 Drawing Sheets

(51) Int. Cl.
| | |
|---|---|
| C12P 9/00 | (2006.01) |
| A62D 3/02 | (2007.01) |
| C12N 9/16 | (2006.01) |
| C12N 9/18 | (2006.01) |
| A62D 101/02 | (2007.01) |
| A62D 101/26 | (2007.01) |

(52) U.S. Cl.
CPC ........... *C12N 11/14* (2013.01); *C12P 9/00* (2013.01); *C12Y 301/01074* (2013.01); *C12Y 301/08002* (2013.01); *A62D 2101/02* (2013.01); *A62D 2101/26* (2013.01)

(56) References Cited

U.S. PATENT DOCUMENTS

| | | |
|---|---|---|
| 2015/0087044 A1 | 3/2015 | Ma et al. |
| 2017/0166661 A1 | 6/2017 | Liang et al. |

FOREIGN PATENT DOCUMENTS

| | | |
|---|---|---|
| WO | WO 2016/010522 | 1/2016 |
| WO | WO 2016/010525 | 1/2016 |
| WO | WO 2017/213871 | 12/2017 |

OTHER PUBLICATIONS

Mondloch et al. Nature Materials, vol. 14, 2015, 512-516.*

Kate Ong thesis. Encapsulation of Organophosphorus Acid Anhydrolase (OPAA) in Nanostructured Materials for the Detection and Decontamination of Chemical Warfare Agents, May 2006, 1-235.*

Aykol et al., "High-throughput Computational Design of Cathode Coatings for Li-ion Batteries," Nature Communications, 2016, pp. 1-12.

Chen et al., "Size-Selective Biocatalysis of Myoglobin Immobilized into a Mesoporous Metal-Organic Framework with Hierarchical Pore Sizes," Inorganic Chemistry, 2012, vol. 51, pp. 9156-9158.

Chen, Yijing, et al. "Acid-Resistant Mesoporous Metal—Organic Framework toward Oral Insulin Delivery: Protein Encapsulation, Protection, and Release." *Journal of the American Chemical Society* 140.17 (2018): 5678-5681.

Chen et al., "How Can Proteins Enter the Interior of a MOF? Investigation of Cytochrome c Translocation into a MOF Consisting of Mesoporous Cages with Microporous Windows," J. Am. Chem. Soc., 2012, vol. 134, pp. 13188-13191.

Deng, et al., "Large-Pore Apertures in a Series of Metal-Organic Frameworks," Science, May 25, 2012, vol. 336, pp. 1018-1023.

Feng et al., "Stable Metal-Organic Frameworks Containing Single-Molecule Traps for Enzyme Encapsulation," Nature Communications, vol. 6, pp. 1-8.

Feng et al., "Zirconium-Metalloporphyrin PCN-222: Mesoporous Metal-Organic Frameworks with Ultrahigh Stability as Biomimetic Catalysts," Angew. Chem. Int. Ed., 2012, vol. 51, pp. 10307-10310.

Horcajada et al., "Metal-Organic Frameworks in Biomedicine," Chemical Reviews, 2012, vol. 112, pp. 1232-1268.

Howarth et al., Chemical, Thermal and Mechanical Stabilities of Metal-Organic Frameworks, Nature Reviews, Mar. 2016, vol. 1, pp. 1-15.

Islamoglu et al., "Revisiting the Structural Homogeneity of NU-1000, a Zr-based Metal-Organic Framework," CrystEngComm, 2018, pp. 1-6.

The International Search Report & Written Opinion dated Nov. 29, 2017 for International Application No. PCT/US17/34416, pp. 1-9.

Kirklin, et al. "High-Throughput Computational Screening of New Li-Ion Battery Anode Materials," Adv. Energy Mater., 2013, vol. 3, pp. 252-262.

Li et al., "Synthesis of Nanocrystals of Zr-based Metal-Organic Frameworks with CSQ-Net: Significant Enhancement in the Degradation of a Nerve Agent Stimulant," Chem. Commun., 2015, vol. 51, pp. 10925-10928.

Li et al., "Encapsulation of a Nerve Agent Detoxifying Enzyme by a Mesoporous Zirconium Metal-Organic Framework Engenders Thermal and Long-Term Stability,". J. Am. Chem. Soc., 2016, vol. 138 No. 26, pp. 8052-8055.

Li et al., "Toward Design Rules for Enzyme Immobilization in Hierarchical Mesoporous Metal-Organic Frameworks," Chem., Jul. 7, 2016, vol. 1, pp. 154-169.

Liang et al., "Biomimetic Mineralization of Metal-Organic Frameworks as Protective Coatings for Biomacromolecules," Nature Communications, 2015, DOI: 10.1038/ncomms8240, pp. 1-8.

Ling et al., "High-throughput Theoretical Design of Lithium Batter Materials," Chin. Phys. B., 2016, vol. 25, No. 1, pp. 0182018-018208-9.

Lo et al., "A Mesoporous Aluminium Metal-Organic Framework with 3 nm open porest," Journal of Materials Chemistry A, 2013, vol. 1, pp. 324-329.

Lykourinou et al., "Immobilization of Mp-11 into a Mesoporous Metal-Organic Framework, Mp-11@Mesomof: A New Platform for Enzymatic Catalysis," J. Am. Chern. Soc., 2011, vol. 133, No. 27, pp. 10382-10385.

Lyu et al., "One-Pot Synthesis of Protein-Embedded Metal-Organic Frameworks with Enhanced Biological Activities," Nano Lett., vol. 14, pp. 5761-5765.

Ma et al., "Toward Topology Prediction in Zr-Based Microporous Coordination Polymers: The Role of Linker Geometry and Flexibility," Crystal Growth & Design, 2016, vol. 16, No. 7, pp. 4148-4153.

Mehta et al., "Recent Advances in Enzyme Immobilization Techniques: Metal-Organic Frameworks as Novel Substrates," Coord. Chem. Rev., 2016, vol. 322, pp. 30-40.

Mondloch et al., "Vapor-Phase Metalation by Atomic Layer Deposition in a Metal-Organic Framework," J. Am. Chem. Soc., 2013, vol. 135, No. 28, pp. 10294-10297.

Morris et al., "Synthesis, Structure, and Metalation of Two New Highly Porous Zirconium Metal-Organic Frameworks," Inorg. Chem., 2012, vol. 51, No. 12, pp. 6443-6445.

Mueller et al., "Evaluation of Tavorite-Structured Cathode Materials for Lithium-Ion Batteries Using High-Throughput Computing," Chemistry of Materials, 2011, vol. 23, pp. 3854-3862.

Shieh et al., "Imparting Functionality to Biocatalysts via Embedding Enzymes into Nanoporous Materials by a de Novo Approach: Size-Selective Sheltering of Catalase in Metal-Organic Framework Microcrystals," J. Am. Chem. Soc., 2015, vol. 137, pp. 4276-4279.

Wang et al., "A Series of Highly Stable Mesoporous Metalloporphyrin Fe-Mofs," J. Am. Chem. Soc., 2014, vol. 136, No. 40, pp. 13983-13986.

Wu et al., "Metal-Organic Frameworks and Inorganic Nanoflowers: a Type of Emerging Inorganic Crystal Nanocarrier for Enzyme Immobilization," Catalysis Science & Technology, 2015, vol. 5, pp. 5077-5085.

Zhang et al., "Piezofluorochromic Metal-Organic Framework: A Microscissor Lift," J. Am. Chem. Soc., 2015, vol. 137, pp. 10064-10067.

Zhou et al., "Recent Progress in Biocatalysis with Enzymes Immobilized on Mesoporous Hosts," Top. Catal., 2012, vol. 55, pp. 1081-1100.

\* cited by examiner

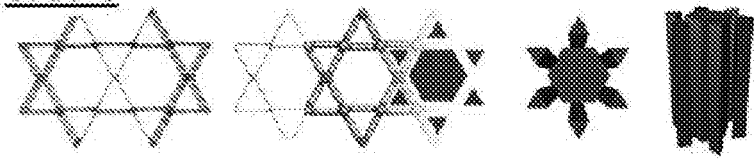
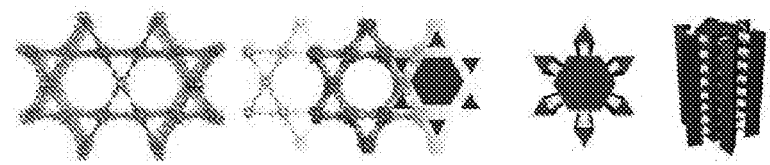

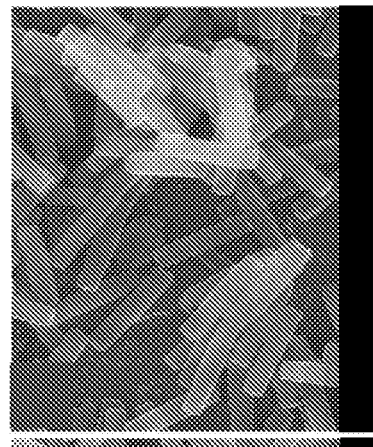
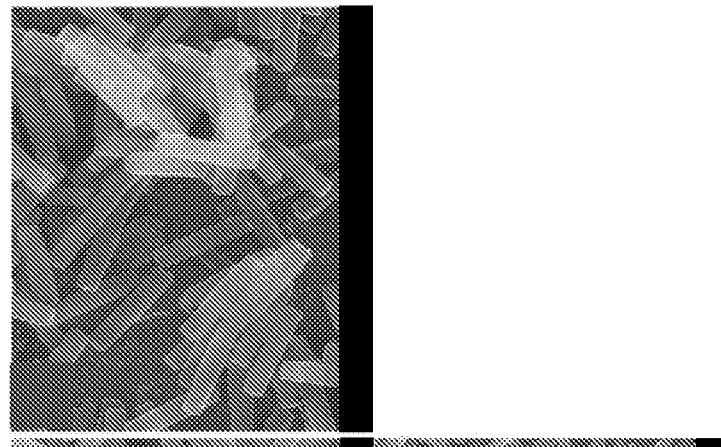
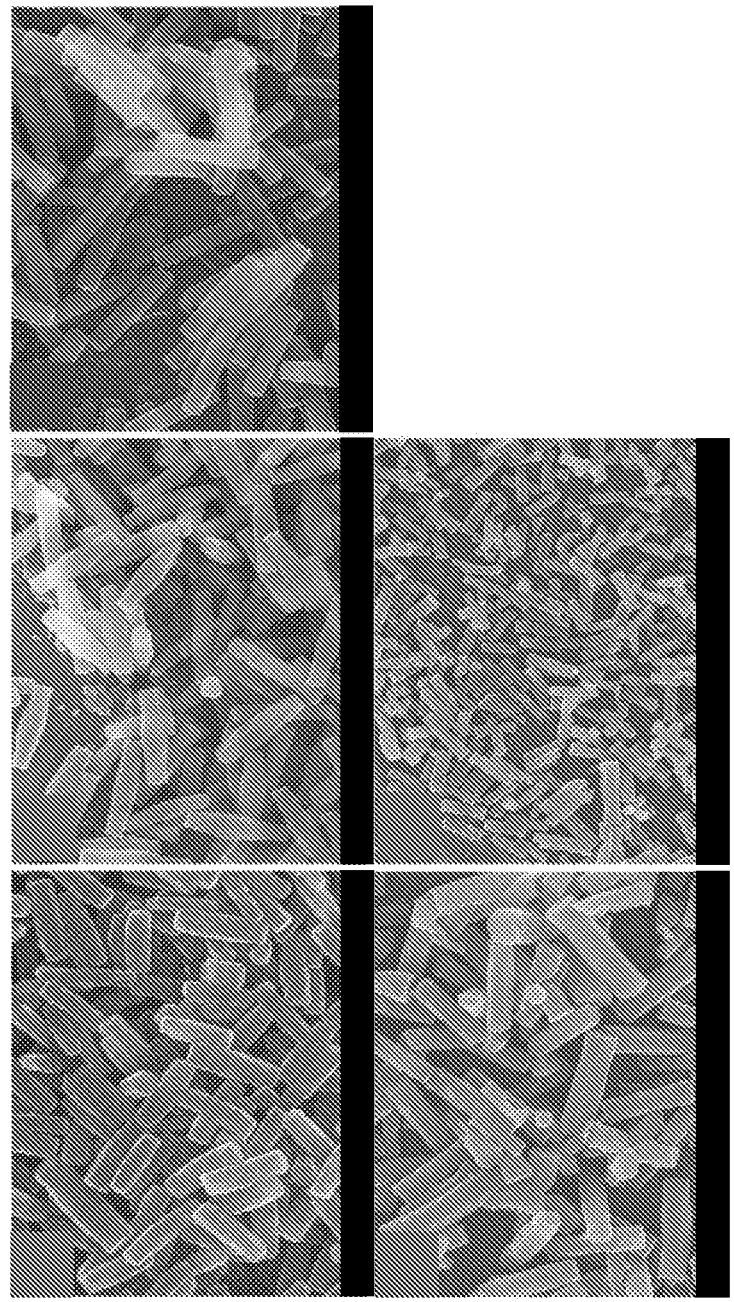

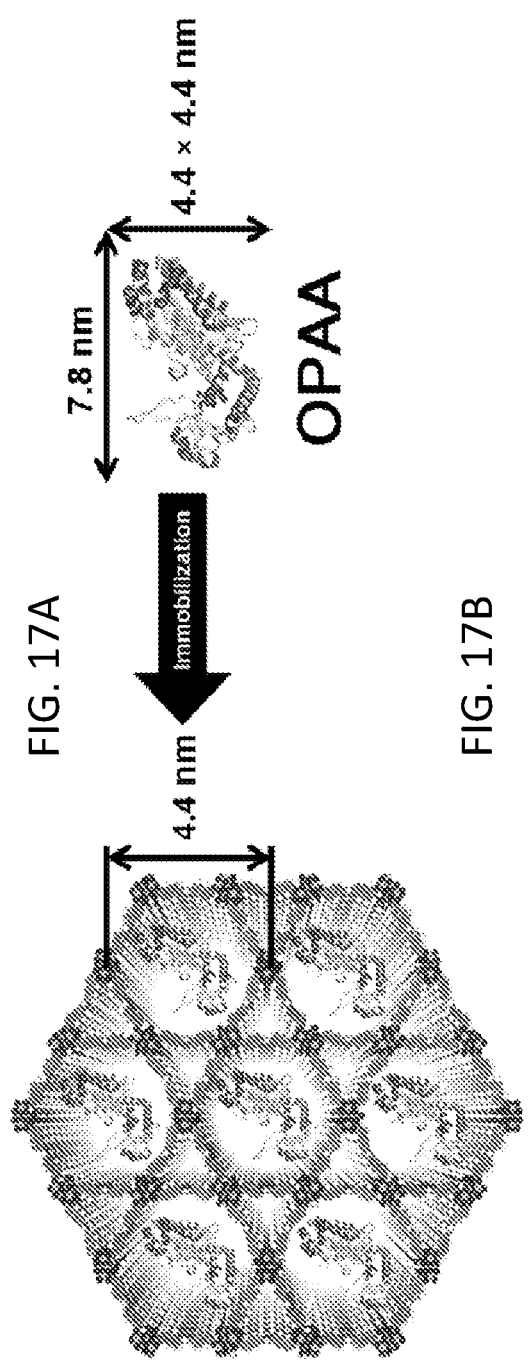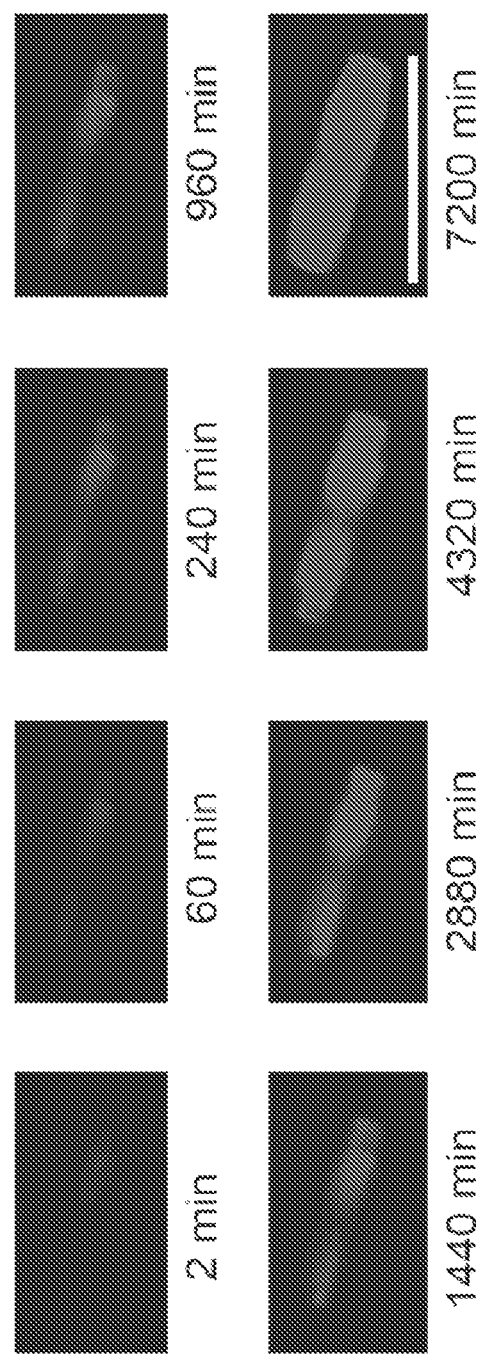
FIG. 17A
FIG. 17B

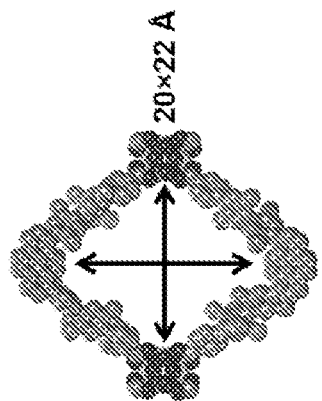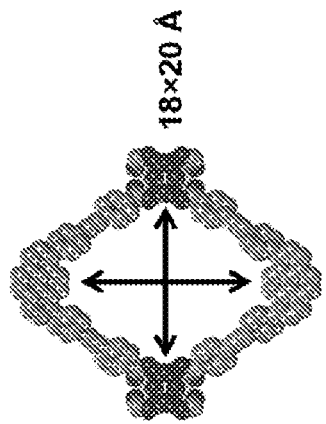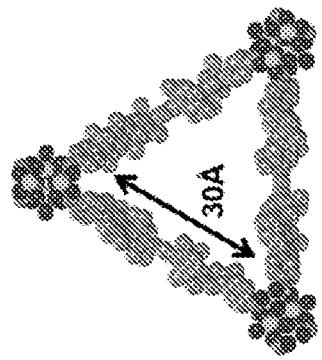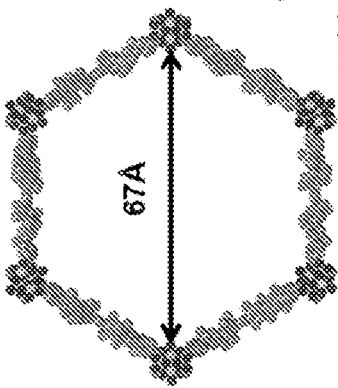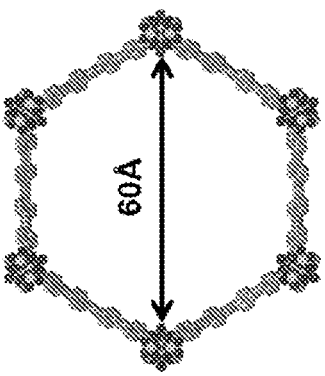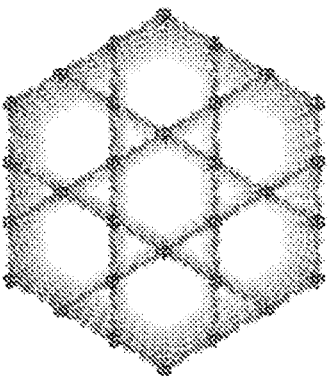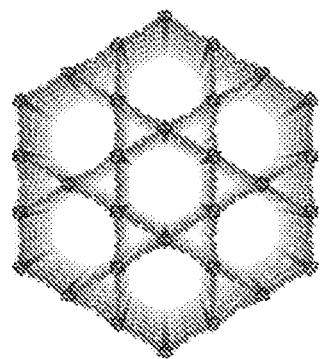
NU-1007
FIG. 20A
NU-1006
FIG. 20B

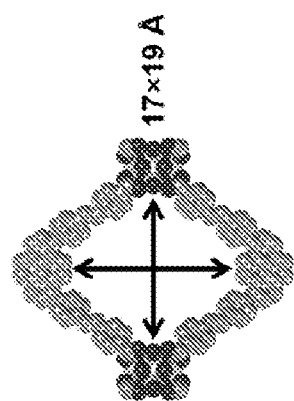 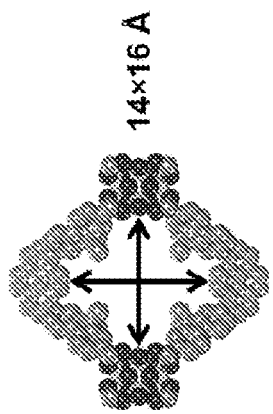
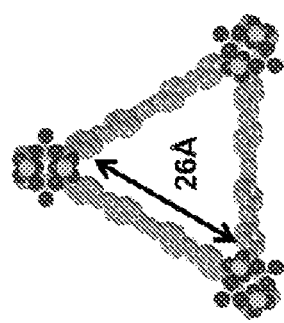 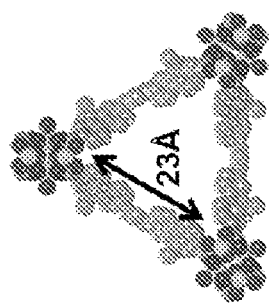
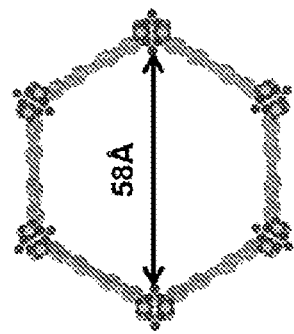 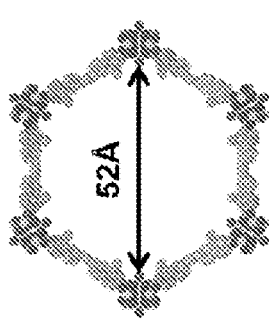
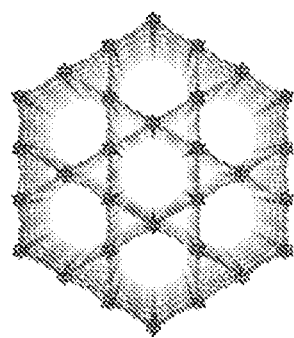 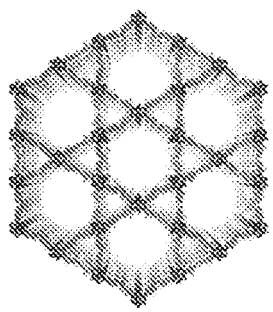
NU-1005
FIG. 20C
NU-1004
FIG. 20D

NU-1003

NU-1000

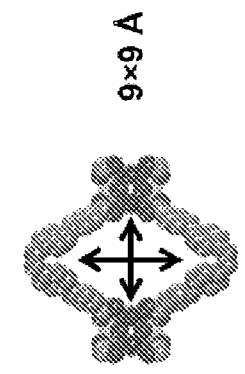
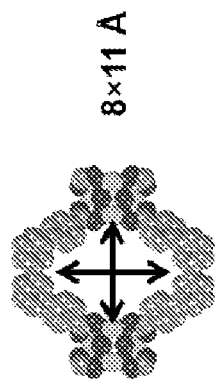
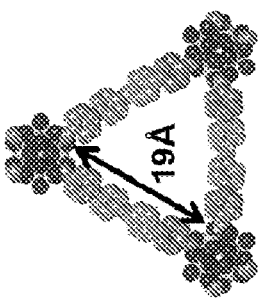
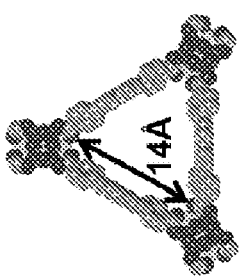
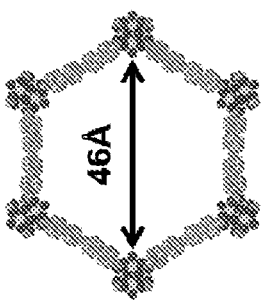
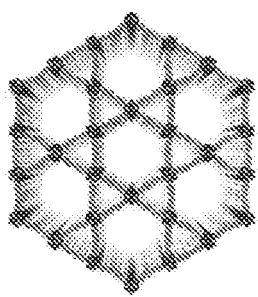
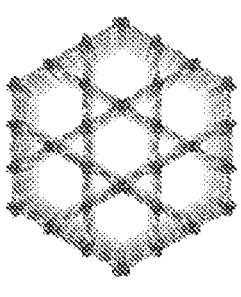
PCN-128
FIG. 21
UMCM-313
FIG. 22

ENZYME IMMOBILIZATION IN HIERARCHICAL METAL-ORGANIC FRAMEWORKS

CROSS-REFERENCE TO RELATED APPLICATIONS

The present application is a National Stage of International Application No. PCT/US2017/034416 that was filed on May 25, 2017, which claims priority from U.S. provisional patent application No. 62/345,656 that was tiled on Jun. 3, 2016, the entire contents of which are hereby incorporated by reference.

REFERENCE TO GOVERNMENT RIGHTS

This invention was made with government support under HDTRA-1-10-0023 awarded by the Defense Threat Reduction Agency and FA9550-16-1-0150 awarded by the Air Force Office of Scientific Research. The government has certain rights in the invention.

BACKGROUND

Enzyme-mediated catalysis is a practical, sustainable and environmentally benign strategy for the production of industrially relevant chemicals ranging from biofuels to pharmaceuticals and food additives. Advances in protein engineering have led to the creation of enzymes with enhanced catalytic performance, yet their use industrially has often been hampered by the lack of long-term stability, recyclability and efficient recovery. These issues can be overcome by using a solid support to immobilize the enzymes and shield them from deactivating reaction conditions (e.g. organic solvents and denaturants), in addition to providing for enzyme recyclability via recovery of the heterogenized catalyst and support.

Some metal-organic frameworks (MOFs) have been used for enzyme immobilization. MOFs are a class of highly tunable, porous materials that have shown promise in a wide range of potential applications including gas storage and release, light harvesting and energy conversion, drug delivery and catalysis. MOFs are potentially superior to other porous materials commonly used to immobilize proteins and enzymes such as sol gels, zeolites and mesoporous silica supports, since MOFs are finely tunable and crystalline, thus exhibiting uniformity and long-range ordering from the atomic to the microscale regime. Enzyme immobilization in less uniform solid supports typically leads to low protein loading efficiency, low stability at elevated temperatures and/or enzyme leaching. Initial studies have shown that some of these challenges can be overcome by using MOFs for enzyme immobilization. These initial studies focused on placing enzymes in cage-like materials without emphasis on the spatial distribution, accessibility, and conformation of the encapsulated enzyme or the diffusion of reactants and products throughout a given support. These characteristics coupled with composite stability, however, are critical design elements of an optimal MOF bioreactor.

Nerve agents are the most toxic of all chemical weapons. Development of antidotal therapy for chemical agent poisoning has been a significant research focus since World War II. The use of catalytic enzymes for nerve agent detoxification has sparked widespread interest due to the excellent biocompatibility and high efficiency of these enzymes. Organophosphorus Acid Anhydrolase (OPAA; EC.3.1.8.2) is a prolidase enzyme that catalyzes the hydrolysis of P—F, P—O, P—CN, and P—S bonds commonly found in toxic organophosphorus compounds and G-type chemical agents. However, the use of OPAA in nerve agent detoxification applications is made difficult by the poor stability of this enzyme in organic solvents, at elevated temperature and when storing the enzyme long-term. Field application requires that the enzyme antidote be easy to handle in dry powder form to reduce complicated and burdensome storage and shipping logistics.

Significant effort has been devoted to developing useful materials as solid supports for encapsulation of OPAA to afford stable and convenient formulation for use in chemical agent detoxification and detection. Previously, various materials including polymers, silica gel, functionalized mesoporous silicas (FMS), and porous silica (PSi)[16] have been used to immobilize OPAA. (See, Furukawa, H., et al. (2013). O. M. The Chemistry and Applications of Metal-Organic Frameworks. *Science* 341, 1230444; Li, J. R., et al. (2009). Selective gas adsorption and separation in metal-organic frameworks. *Chem. Soc. Rev.* 38, 1477-1504; Mason, J. A., et al. (2014). Evaluating metal-organic frameworks for natural gas storage. *Chem. Sci.* 5, 32-51; Peng, Y., et al. (2013). Methane Storage in Metal-Organic Frameworks: Current Records, Surprise Findings, and Challenges. *J. Am. Chem. Soc.* 135, 11887-11894.) For example, FMS encapsulated OPAA shows enhanced tolerance to organic solvents. Nevertheless, due to a lack of long-range ordering, the loading capacity of OPAA in FMS is usually very low (<0.01 wt %). (See, Peng, Y., et al. (2013). Methane Storage in Metal-Organic Frameworks: Current Records, Surprise Findings, and Challenges. *J. Am. Chem. Soc.* 135, 11887-11894.) In addition, enhanced thermal and long-term stability of immobilized OPAA has not yet been achieved. Therefore, the development of new host materials is important for targeting both high enzyme loading and enhanced stability for OPAA immobilization.

SUMMARY

Hierarchical, MOFs having enzymes immobilized therein and methods of using the MOFs in enzymatically catalyzed reactions are provided.

One embodiment of an enzyme-immobilizing metal-organic framework comprises: a channel-type metal-organic framework compound having a hierarchical pore structure comprising a first set of large channels, a second set of small channels running alongside of the large channels, and openings defined between the large channels and the small channels, the large channels having a larger diameter than the small channels; and catalytically active enzymes immobilized in the large channels, wherein the small channels are free of the catalytically active enzymes.

One embodiment of a method of enzymatically catalyzing a reaction using an enzyme-immobilizing metal-organic framework compound comprises the step of exposing the enzyme-immobilizing metal-organic framework compound to a sample comprising chemical reactants under conditions in which the immobilied enzymes catalyze a reaction between the reactants to form one or more reaction products.

Other principal features and advantages of the invention will become apparent to those skilled in the art upon review of the following drawings, the detailed description, and the appended claims.

BRIEF DESCRIPTION OF THE DRAWINGS

Illustrative embodiments of the invention will hereafter be described with reference to the accompanying drawings.

FIG. 2A shows simulated PXRD of NU-1000 and experimental PXRD of NU-1000 before and after cutinase loading. FIG. 2B shows an $N_2$ sorption isotherm of NU-1000 and Cutinase@NU-1000 at 77 K. FIG. 2C shows the pore size distribution of as-synthesized NU-1000 and cutinase@NU-1000.

FIG. 3A shows scanning electron microscopy images of 10 µm long crystals (inset image shows the typical hexagonal cylinder morphology of NU-1000 crystals). FIG. 3B shows scanning electron microscopy images of 1.5 µm long crystals. FIG. 3C shows confocal laser scanning microscopy images of a 10-µm NU-1000 crystal (scale bar depicted is 10 µm) after immersion in 100 µM Cut647 solution over time. FIG. 3D shows confocal laser scanning microscopy images of a 1.5-µm NU-1000 crystal (scale bar depicted is 1.5 µm) after immersion in 100 µM Cut647 solution over time. FIG. 3E shows an overlay of experimental Cut647 concentration (dots) and corresponding simulated fits (lines) along the middle of a 10-µm NU-1000 crystal. FIG. 3F shows and an overlay of experimental Cut647 concentration (dots) and corresponding simulated fits (lines) along the middle of a 1.5-µm NU-1000 crystal at different time points. In FIGS. 3A-3F, the lowest line is for 2 minutes and the time increases as the lines go up, so that the highest line is for 7200 minutes (FIG. 3E) or 600 minutes (FIG. 3F).

FIG. 4A depicts a model of cutinase@NU-1000 after geometry optimization (NU-1000 and active triad of cutinase—Ser126, Asp180, and His194—are displayed in CPK model). FIG. 4B shows dye molecules fluorescein and (4,4',4'',4'''-(porphine-5,10,15,20-tetrayl)tetrakis(benzoic acid) (TCPP) used to test reactant diffusion in cutinase@NU-1000-10 µm. FIG. 4C shows a 3D reconstructed image of Cut647@NU-1000-10 µm crystals containing fluorescein (scale bar depicted is 10 µm). FIG. 4D shows 2D CLSM images taken using different laser channels to view Cut647, TCPP, both Cut647 and TCPP in a single NU-1000-10 µm crystal (scale bar depicted is 10 µm). FIGS. 4E-4H show in silico modeling of structure of Cutinase@NU-1000. FIG. 4E shows a perspective view. FIG. 4F shows the side. FIG. 4G shows orthogonal views of overlapped cutinase molecules before and after geometry optimization in an NU-1000 channel. FIG. 4H is a schematic showing the change in cutinase size and shape before and after encapsulation.

FIG. 5A show a magnified CLSM image of a single NU-1000-10 µm crystal containing active cutinase blocked by deactivated cutinase. FIG. 5B show a magnified CLSM image of multiple crystals of NU-1000 showing active and deactivated cutinase. FIG. 5C shows a CLSM image of the in-situ hydrolysis of resorufin butyrate using cutinase@NU-1000 containing active and deactivated cutinase for 5 seconds. FIG. 5D shows a CLSM image of in-situ hydrolysis of resorufin butyrate using cutinase@NU-1000 containing active and deactivated cutinase for 60 seconds in buffer solution at room temperature (scale bars in FIGS. 5A-5D depicted are 10 µm).

FIG. 6A shows reaction kinetics of PNPB hydrolysis by cutinase@NU-1000, NU-1000, and the supernatant solution used to soak cutinase@NU-1000 (final wash). FIG. 6B depicts a kinetic study of hydrolysis of PNPB by cutinase@NU-1000 and free cutinase in buffer with detergent. FIG. 6C shows a kinetic study of hydrolysis of PNPB by cutinase@NU-1000 and free cutinase in buffer without detergent. FIG. 6D shows a kinetic study of hydrolysis of PNPB by cutinase@NU-1000 and free cutinase in buffer with urea. FIG. 6E shows a kinetic study of hydrolysis of PNPB by cutinase@NU-1000 and free cutinase in buffer with THF. FIG. 6F depicts a recyclability test of cutinase@NU-1000 in buffer without detergent.

FIG. 7A shows a perspective view of one-dimensional channels of PCN-600, CYCU-3, and NU-1000. Cylinders represent the channels and tunnels indicate the connectivity between neighboring channels. FIG. 7B is a schematic of an enzyme loading and surface treatment process. FIG. 7C is a graph of the maximum loading capacity, enzymes encapsulated in channels, and accessible enzymes in nanosized MOFs.

FIG. 16A shows an SEM image of crystals with length of 300 nm. FIG. 16B shows an SEM image of crystals with length of 1000 nm. FIG. 16C shows an SEM image of crystals with length of 2000 nm. FIG. 16D shows shows an SEM image of crystals with length of 7000 nm. FIG. 16E shows an SEM image of crystals with length of 10000 nm.

FIG. 17A is a schematic representation of immobilization of OPAA in the mesoporous channels of NU-1003. FIG. 17B shows CLSM images of a single crystal of OPAA@NU-1003-10000 nm with time (scale bar is 10 μm).

FIG. 20A shows the structure of MOF NU-1007. FIG. 20B shows the structure of MOF NU-1006. FIG. 20C shows the structure of MOF NU-1005. FIG. 20D shows the structure of MOF NU-1004.

FIG. 21 shows the structure of MOF PCN-128.

FIG. 22 shows the structure of MOF UMCM-313.

DETAILED DESCRIPTION

Figure 1:
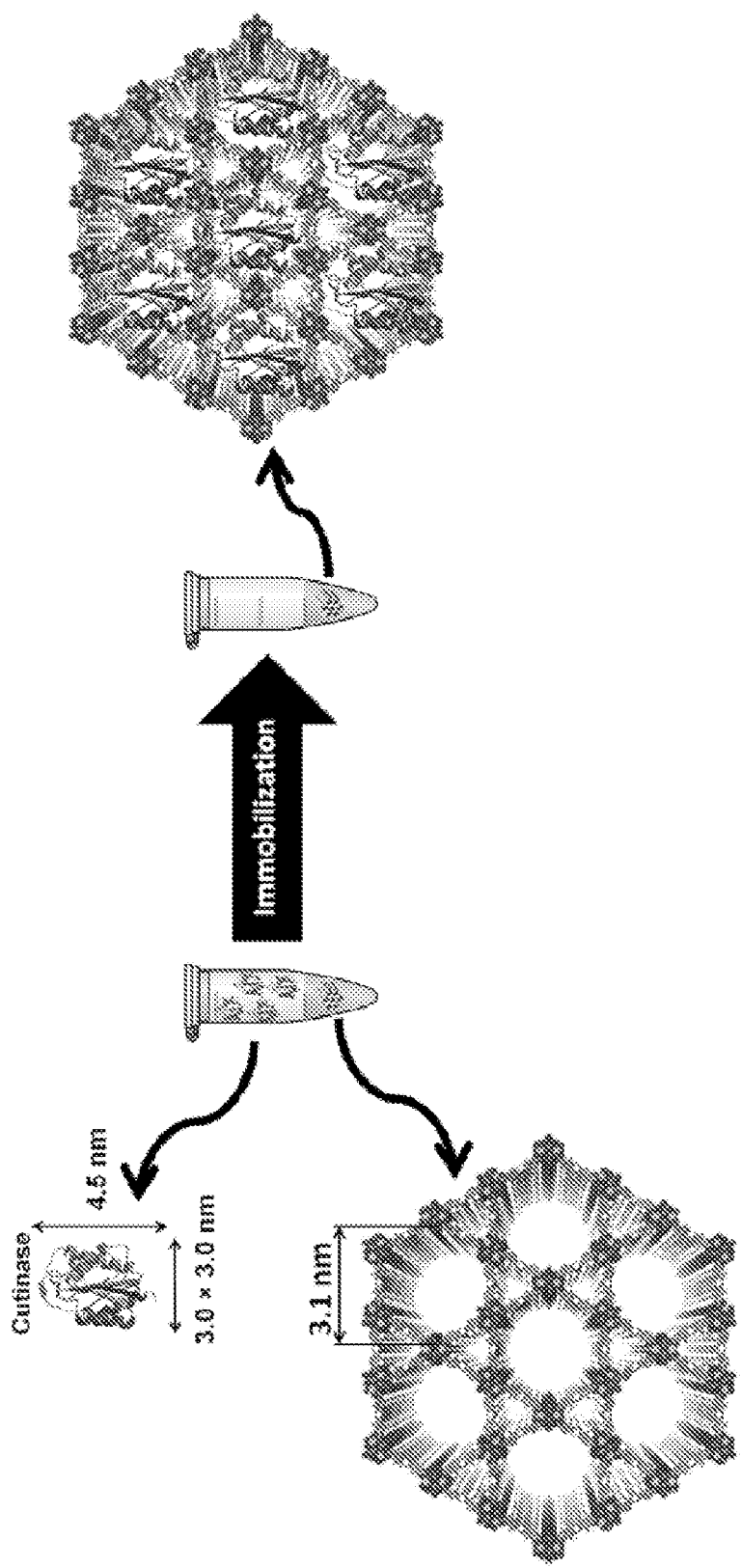
FIG. 1 depicts immobilization of cutinase in the mesoporous channels of NU-1000.

Hierarchical, mesoporous MOFs having enzymes immobilized therein and methods of making and using the MOFs are provided.

MOFs constitute a particular class of solid-state compounds that are built up from multitopic organic molecular linkers that bridge and interconnect metal-based nodes in the compounds.

The MOFs used in the present methods have a hierarchical pore structure and a combination of properties that render them well-suited for use as scaffolds for immobilizing enzymes, such that the enzymes maintain full, or substantially full, enzymatic catalytic activity. In some embodiments, the immobilized enzymes have greater resistance to attack by organic solvents, such as urea and tetrahyrofuran, and denaturization than their corresponding free (i.e., not immobilized) enzymes. In addition, the immobilized enzymes can have greater reactant accessibility and higher activity than the same enzymes encapsulated in topologically simpler metal-organic frameworks. In some embodiments of these methods, the catalytic efficiency of the immobilized enzyme is the same as, or even greater than, that of its free counterpart in solution under the same conditions.

The MOFs are channel-type MOFs that present a hierarchical pore structure comprising a first set of large channels sized for enzyme immobilization and a second set of smaller channels, running alongside of the large channels that may remain enzyme-free and that allow for reactant delivery to the enzymes and for product expulsion from the larger channels. (By "smaller" it is meant that the channels have smaller diameters than the large channels.) The large channels may be sized such that the diameter of the channel is larger than the small axis length of the enzyme to be immobilized, such that the enzymes are oriented along their long axis when they are immobilized within a channel. In some embodiments, the MOF and the enzymes are oppositely charged and Coulombic forces help to immobilize the enzymes within the MOF. In some embodiments, the interior surfaces of the channels are functionalized with fluorocarbons, polypeptides, organic acids and/or bases, luminescent dyes, and/or metal-sulfide clusters.

The smaller channels are desirably sufficiently small that they cannot be infiltrated by the enzymes to be immobilized and, typically, have a different cross-sectional shape than the larger channels. By way of illustration, MOFs having a framework with a csq-net topology characterized by large hexagonal channels and smaller triangular channels may be used to immobilize various enzymes. MOFs of this type are described in Mondloch et al., *J. Am. Chem. Soc.* 2013, 135 (28), 10294-10297; Feng, et al., *Angew. Chem., Int. Ed.* 2012, 51 (41), 10307-10310; Morris, et al., *Inorg. Chem.* 2012, 51 (12), 6443-6445; and Gomez-Gualdron, et al., *Chem. Mater.* 2014, 26 (19), 5632-5639. The disclosures of these references are incorporated herein for the purpose of describing the structure of the MOFs. In the MOFs, there are openings (or "windows") between the large and small channels that allow for reactant diffusion between the differently sized channels. These openings define holes in the structure that forms the channel walls.

One specific example of a MOF having such a pore structure is the water-stable, mesoporous, zirconium-based MOF denoted NU-1000 in Mondloch, et al. Vapor-Phase Metalation by Atomic Layer Deposition in a Metal-Organic Framework. *J. Am. Chem. Soc.* 135, 10294-10297 (2013). NU-1000 has hexagonal channels with a diameter of 3.1 nm as well as triangular channels with an edge length of 1.5 nm, with windows connecting the two channels. Another specific example is the MOF denoted PCN-128y in Zhang et al., *J. Am. Chem. Soc.* 2015, 137 (32), 10064-10067.

Figure 23:
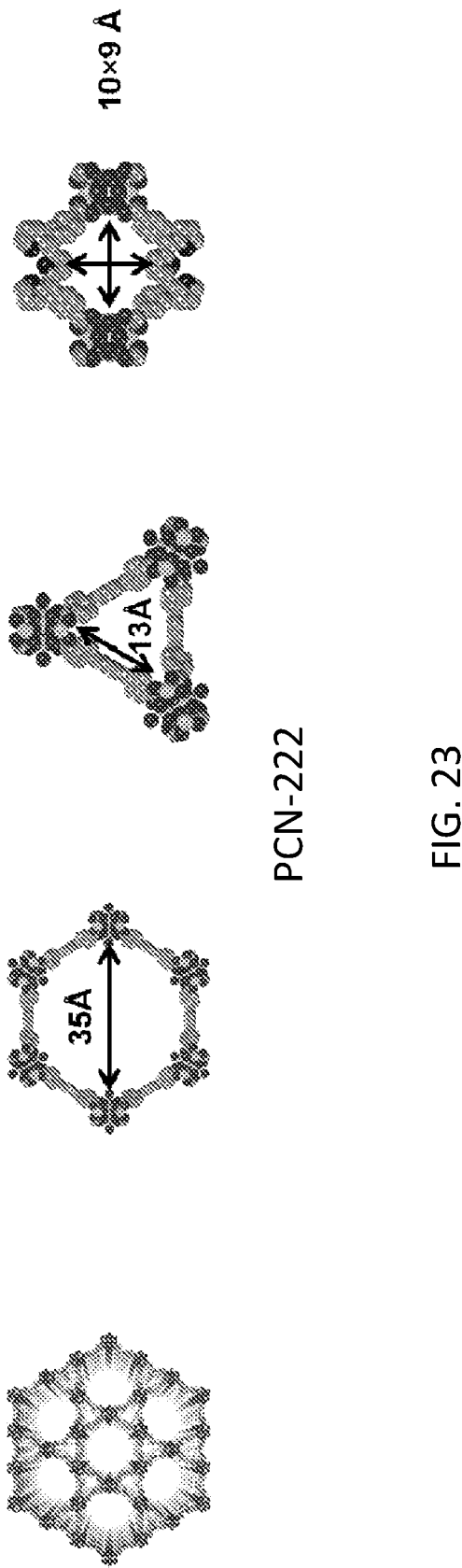
FIG. 23 shows the structure of MOF PCN-222.
Figure 24:
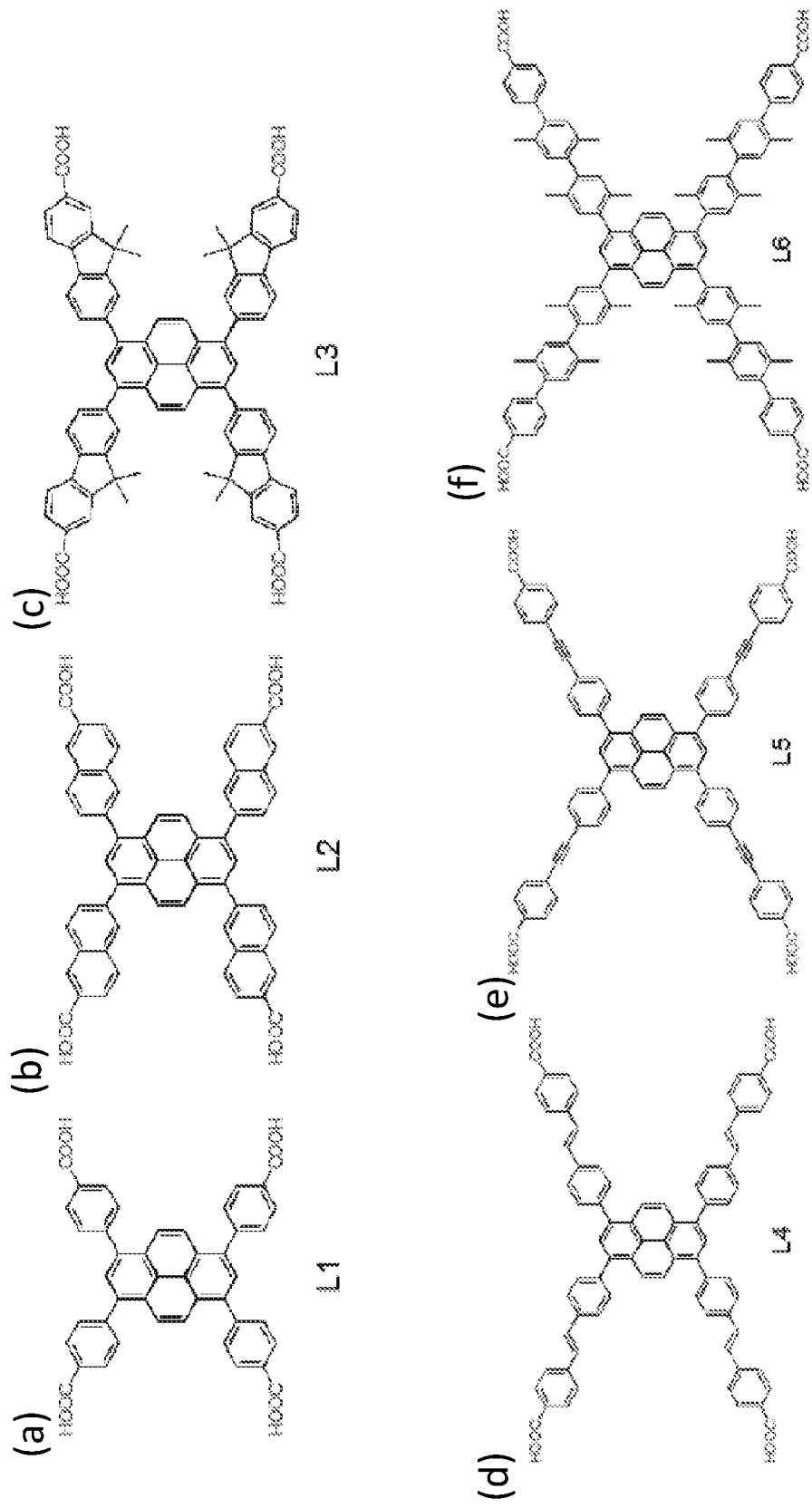
FIG. 24, panels (a) through (f), shows examples of organic molecules that can be used to form different pyrene-based organic linkers in the synthesis of a MOF.

The MOF having a csq-net topology include mesoporous zirconium MOFs having eight $Zr_6$ cluster nodes connected by tetratropic linkers, where a Zr6 cluster node has the structure $Zr_6(\mu_3\text{-O})_4(\mu_3\text{-OH})_4(OH)_4(H_2O)_4$ or a variation of that structure in which some or all of the hydroxo ligands are replaced with oxo and/or hydroxo ligands. For example, one family of such MOFs has pyrene-based tetratopic linkers connecting the metal cluster nodes. The pyrene-based linkers can include various aryl groups in their linker chains, including phenyl groups, bi-phenyl groups, and napthyl groups. The structure of these types of MOFs is illustrated in FIGS. 20A, 20B, 20C, 20D, 20E, and 20F, which show MOFs designated NU-1007, NU-1006, NU-1005, NU-1004, NU-1003, and NU-1000, respectively. Other csq-net topology MOFs include those having eight $Zr_6$ cluster nodes connected by ethene-1,1,2,2-tetrayl)tetrakis-(([1,1'-biphenyl]-4-carboxylic acid))) (ETTC) linkers. The structure of the PCN-128 MOF is shown in FIG. 21 and described in Zhang et al, *J. Am. Chem. Soc.*, 2015, 137, 10064-10067, which is incorporated herein for the purposed of describing the structure of the MOF. Still other csq-net topology MOFs have $Zr_6$ cluster nodes connected by parylene-based tetratopic linkers. The structure for one such MOF, UMCM-313 is shown in FIG. 22 and described in Ma et al., *Cryst. Growth Des.*, 2016, 16 (7), pp 4148-4153, which is incorporated herein by reference for the purpose of describing the structure of the MOF. MOFs having a csq-net topology formed from $Zr_6$ clusters connected by porphyrin-based linkers can also be used. FIG. 23 shows the structure on one such MOF, denoted PCN-222. In each of FIGS. 20A through 23, the approximate diameter of the larger, hexagonal channel, the approximate side length of the smaller, triangular channel, and the approximate height and width dimensions of the windows between the large and small channels is provided. Methods for making the MOFs are illustrated in the Examples. Examples of organic molecules that can be used to form different pyrene-based organic linkers in the synthesis of a MOF are shown in FIG. 24, panels (a) through (f).

A particular heirarchical MOF can be selected, based on the dimensions of its large channels, small channels, and windows, depending on the dimensions of the enzyme to be immobilized and the sizes of the reactants and products of the reaction to be catalyzed. By way of illustration only, some embodiments of the MOFs have large channels with diameters in the range from 2 nm to 8 nm, including from 3 nm to 7 nm; smaller channels with a side length in the range from 0.5 nm to 5 nm, including from 0.9 nm to 3 nm; and/or window dimensions (heights and widths) in the range from 0.5 nm to 3 nm, including from 0.8 nm to 2.5 nm.

The enzyme loading in the MOFs can be quite high, with the enzymes uniformly permeating to the center of the MOFs. For example, in some embodiments of the enzyme-immobilizing MOFs, the enzyme loading is at least 5 weight percent (wt %). This includes embodiments of the enzyme-immobilizing MOFs having an enzyme loading of at least 10 wt % and further includes embodiments of the enzyme-immobilizing MOFs having an enzyme loading of at least 12 wt %.

Once the enzymes have been immobilized in the larger channels of the hierarchical MOFs, they can be used to catalyze enzymatic reactions by exposing the MOFs to a sample comprising chemical reactants under conditions (for example, temperatures, pressures, and durations) in which the immobilied enzymes catalyze a reaction between the reactants. The resulting reaction products can then diffuse out of the MOF and be collected and the immobilized enzymes can be recovered and recycled. As illustrated in the examples below, the types of enzymes that can immobilized include, but are not limited to, biocatalytic enzymes, prolidase enzymes, and enzymes that catalyze the hydrolysis of nerve agents.

The sizes of the MOF crystals used to immobilize the enzymes and catalyst reactions is not particularly limited. However, in order to increase the time needed for reactants and products to diffuse into and out of the MOFs, it may be advantageous to use smaller MOF crystals. By way of illustration only, the MOF crystals may include those having lengths in the range from 100 nm to 10 μm. This includes MOF crystals having lengths in the range from 100 to 1 μm. In some such embodiments, the average length of the MOF crystals in a given MOF crystal sample will lie within these ranges.

EXAMPLES

Example 1: Immobilization of *F. solani Pisi* Cutinase by NU-1000

This Example illustrates the use of the MOF NU-1000 to immobilize *F. solani pisi* cutinase. *F. solani pisi* cutinase (PDB ID:1CEX) is an esterase that has shown promise as a biocatalyst in the preparation of aliphatic esters. The larger channels of NU-1000 have sizes that are matched to cutinase, an ellipsoid-shaped protein featuring a small-axis length of ~3.0 nm. These features in addition to the high chemical (including pH 1-11) and thermal stability (>450° C.) of NU-1000, make this MOF a useful material for use as a solid support in biocatalysis.

Results and Discussion
Cutinase Immobilization

Figure 2A:
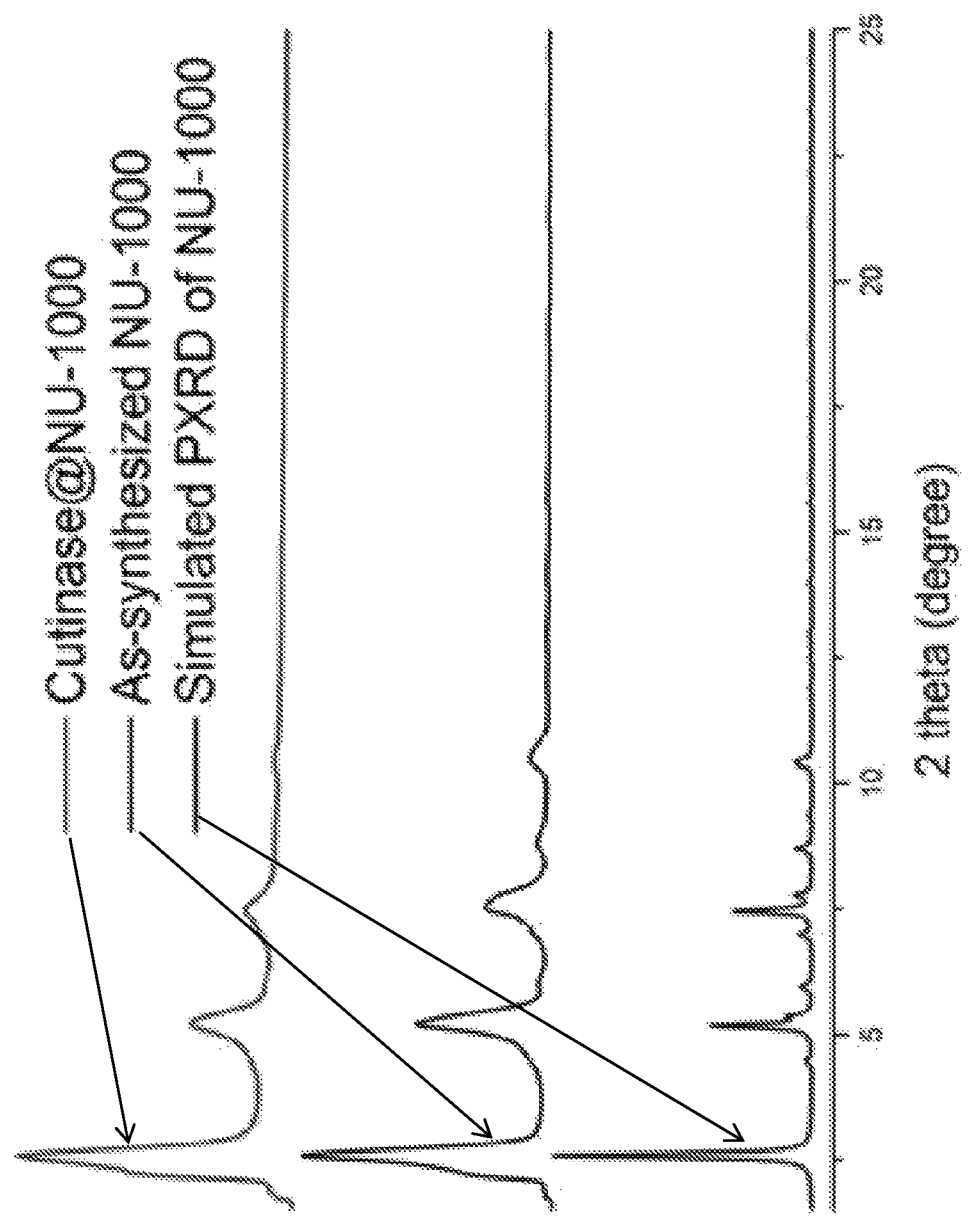
FIGS. 2A-2C depict PXRD and $N_2$ isotherms of Cutinase@NU-1000.
Figure 2B:
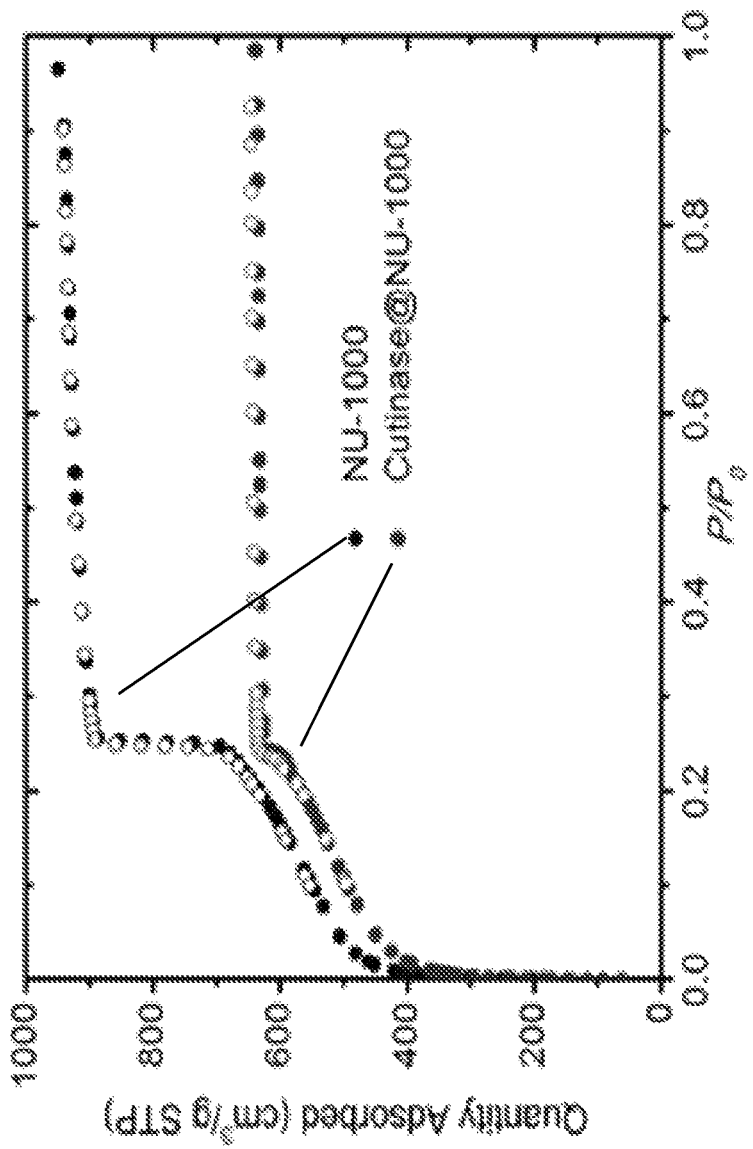
Figure 2C:
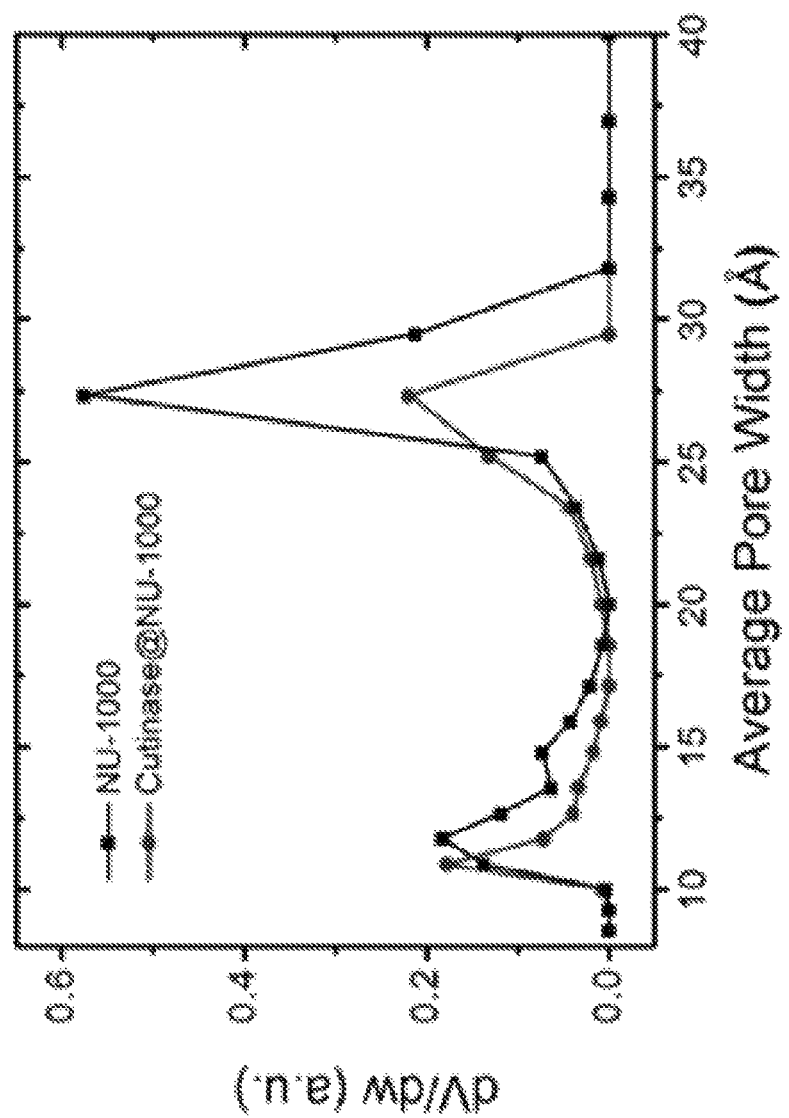

Five μm long activated crystals of the MOF (NU-1000-5 μm) were treated with a tris buffered saline (TBS) solution of cutinase (100 μM, pH 7.4) at 25° C. (FIG. 1). The uptake of cutinase by NU-1000-5 μm was determined using UV-vis spectroscopy and a maximum loading of 5 μmol/g was reached after ~75 h. The solid sample (hereafter denoted as cutinase@NU-1000-5 μm) was then washed with detergent-containing buffer solution five times to ensure full removal of any loosely bound cutinase. Inductively coupled plasma-optical emission spectroscopy (ICP-OES) of the washed cutinase@NU-1000-5 μm sample also revealed a cutinase uptake of 5 μmol/g. The powder X-ray diffraction (PXRD) pattern of NU-1000-5 μm before and after cutinase immobilization confirms that bulk crystallinity was retained after cutinase encapsulation (FIG. 2A). Cutinase@NU-1000-5 μm exhibits a type IV $N_2$ adsorption-desorption isotherm much like NU-1000-5 μm itself, but not surprisingly, the MOF exhibits a lower $N_2$ uptake capacity when cutinase is present in the pores (FIG. 2B). The density functional theory (DFT) pore size distribution analysis of activated NU-1000-5 μm and cutinase@NU-1000-5 μm shows the two different pores comprising the hierarchical structure (FIG. 2C). The pore volume corresponding to the triangular channels of NU-1000-5 μm drops from 0.50 $cm^3/g$ to 0.44 $cm^3/g$, while the pore volume corresponding to the hexagonal channels drops from 0.75 $cm^3/g$ to 0.22 $cm^3/g$ after cutinase encapsulation.

Figure 3B:
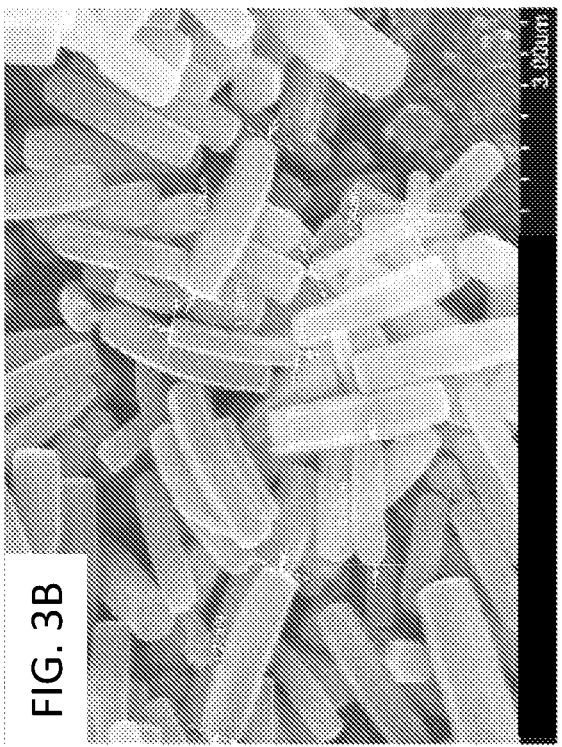
FIGS. 3A-3F depict the diffusion of Cut647 into NU-1000 crystals with different lengths.
Figure 3D:
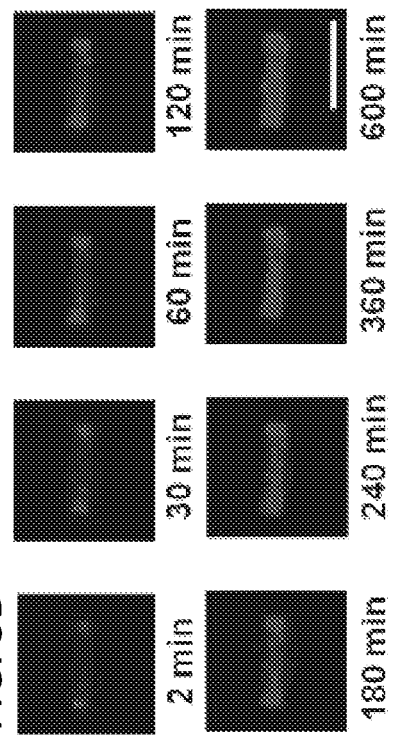
Figure 3A:
Figure 3C:
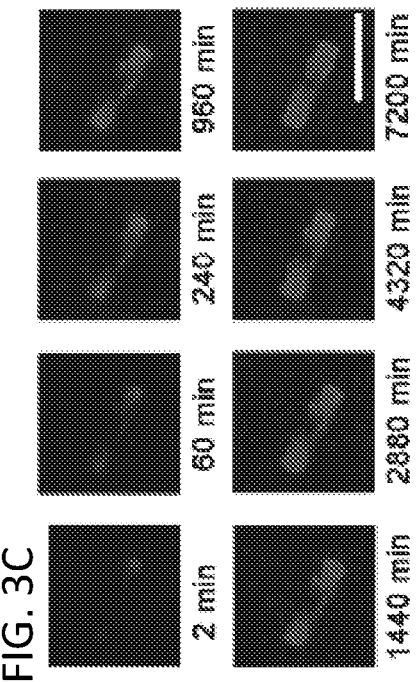

To confirm that cutinase was internalized within NU-1000 and not simply adsorbed on the external surface or within defects of the crystal, in-situ confocal laser scanning microscopy (CLSM) was used to image the cutinase encapsulation process with an AlexaFluor-647-labeled enzyme (Cut647). To study the effect of crystal length on enzyme diffusion, NU-1000 crystals were synthesized with an average length of 10 μm and 1.5 μm (FIGS. 3A-3B). The crystals were immersed in a 50 μM solution of Cut647 while two-dimensional (xy) fluorescence intensity profiles of the MOF samples were obtained at a fixed z depth corresponding to the center layer of the crystal. These images (FIGS. 3C-3D) indicate that the dye-labeled enzyme is in fact directed to the center of NU-1000 and that by decreasing the size of the particle from 10 to 1.5 μm, the time required to reach cutinase saturation decreased by approximately ten-fold.

Figure 3E:
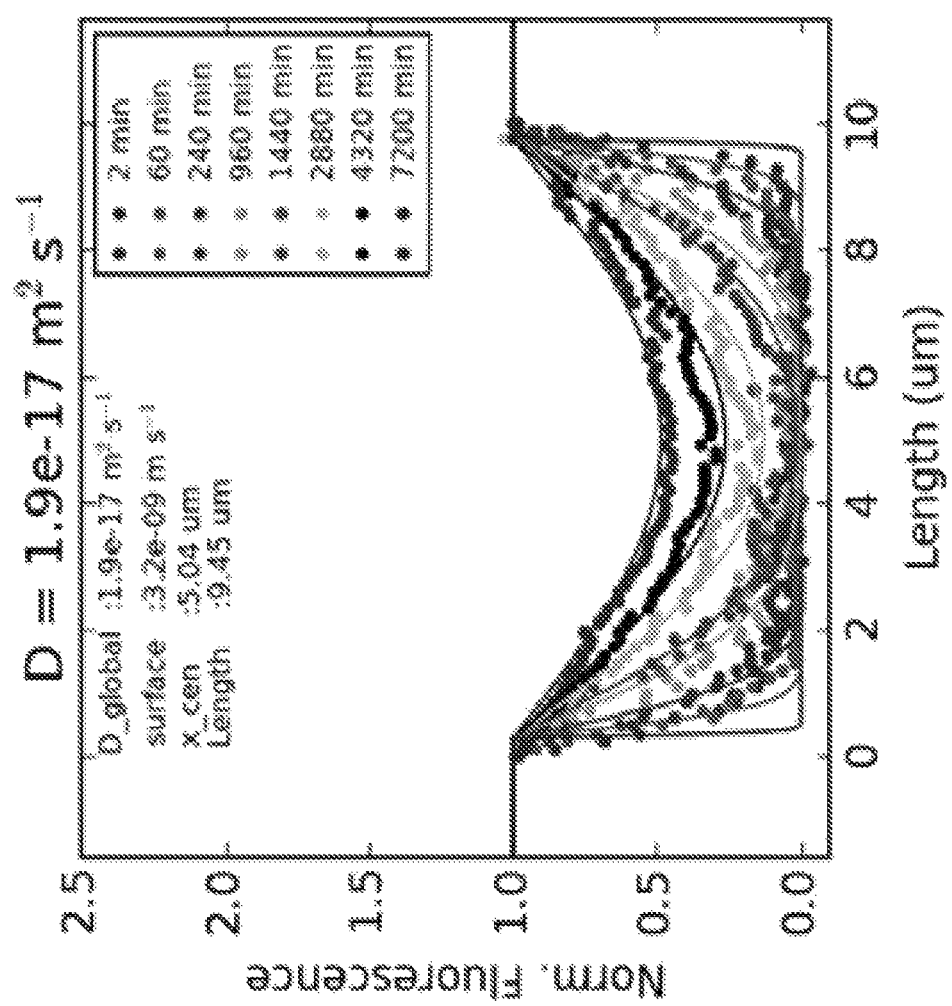
Figure 3F:
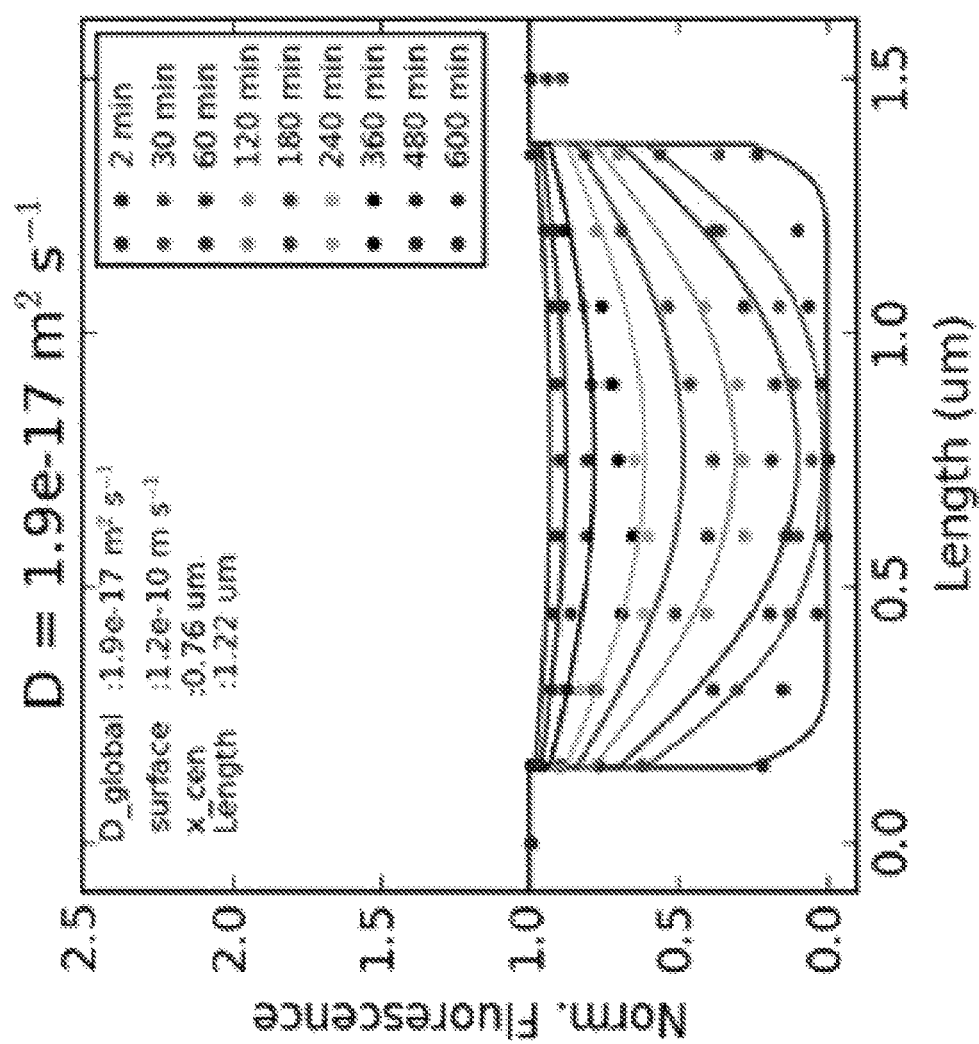

The diffusion process was also modeled using Fick's second law in one dimension (FIGS. 3E-3F). The best-fit value for the diffusion coefficient for Cut647 within NU-1000 was $2\times10^{-13}$ cm$^2$/s, which is consistent with diffusive transport through the crystalline channels. The coefficient was found to be identical for 10 µm and 1.5 µm NU-1000 crystals. For comparison, the diffusion coefficient of cutinase on a 2D trymyristin support was found to be $8.0\times10^{-10}$ cm$^2$/s[36]. These results suggest a strong interaction between Cut647 and NU-1000. In order to explain the nature of this strong interaction, the zeta potential of NU-1000 was examined with varying pH, which indicates an isoelectric point at approximately pH 4.3. This isoelectric point is consistent with a previous study on the Brønsted acidity of NU-1000. Cutinase is known to have isoelectric point at approximately pH 7.8. Thus, in pH 7 buffer solution, cutinase and NU-1000 are positively and negatively charged respectively. The strong interaction between Cut647 and NU-1000 can therefore be attributed to columbic forces.

Molecular mechanics calculations were also used to computationally introduce a reported crystal structure of *F. solani pisi* cutinase into the hexagonal channels of NU-1000. The results indicated that in order to infiltrate the MOF, the long axis of the enzyme must orient along the mesoporous channel of NU-1000. In addition, the shape of cutinase changed slightly to allow for diffusion into the channels of NU-1000, resulting in an ellipsoid that is further elongated compared to that of the original cutinase structure (FIG. 4A and FIGS. 4E, 4F, 4G, and 4H). These models qualitatively support the observed small diffusion coefficients, as the enzyme must slightly deform to fit within the mesopore. Additionally, the models indicate that the catalytically active site in cutinase, composed of amino acid residues Ser126, Asp180, and His194, should remain accessible after encapsulation, with no indication of blocking by any framework components.

Cutinase Accessibility in NU-1000

Figure 4A:
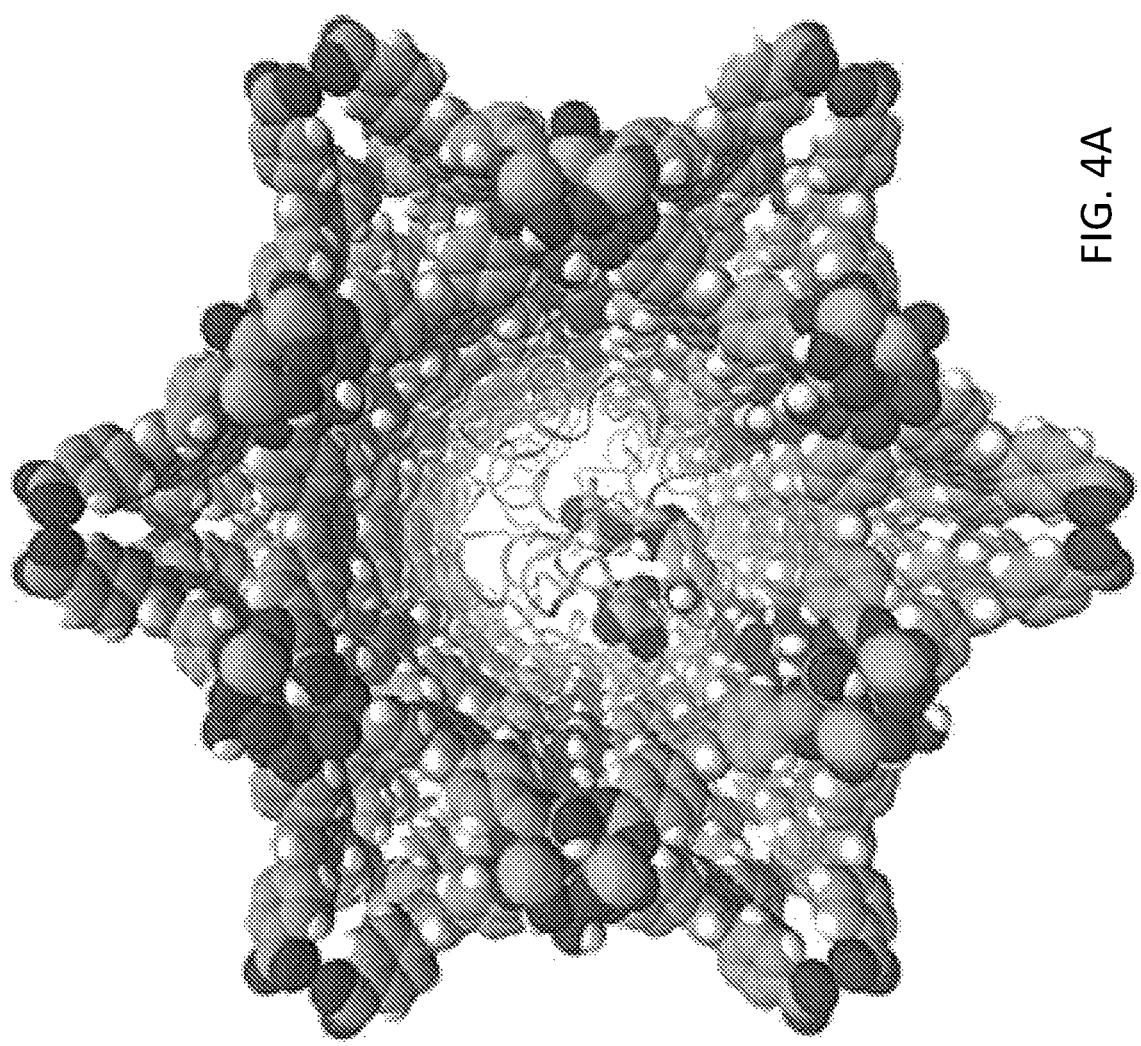
FIGS. 4A-4H show a simulation model and substrate permeability of cutinase@NU-1000.
Figure 4B:
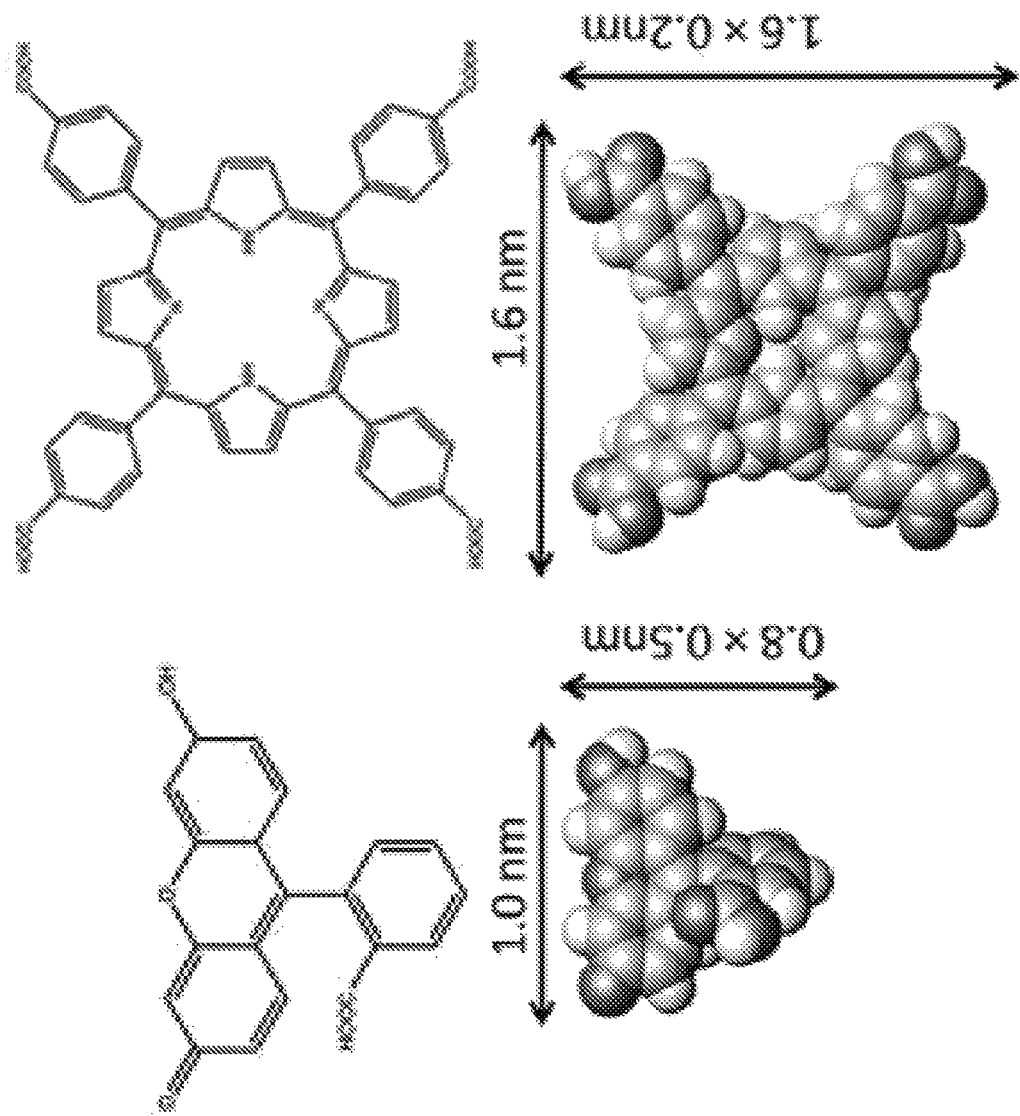
Figure 4D:
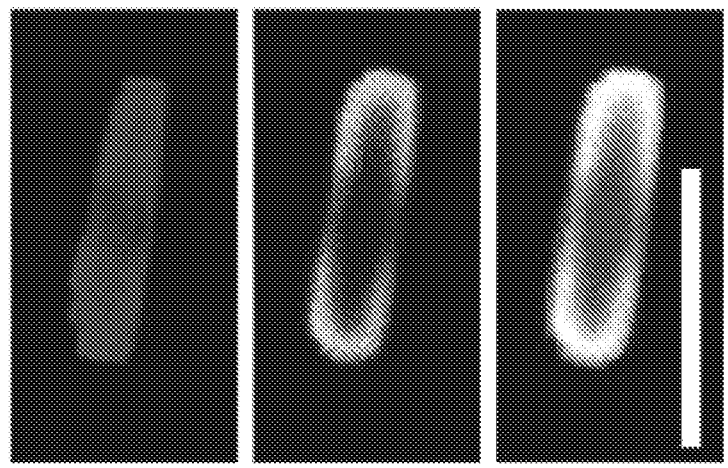
Figure 4C:
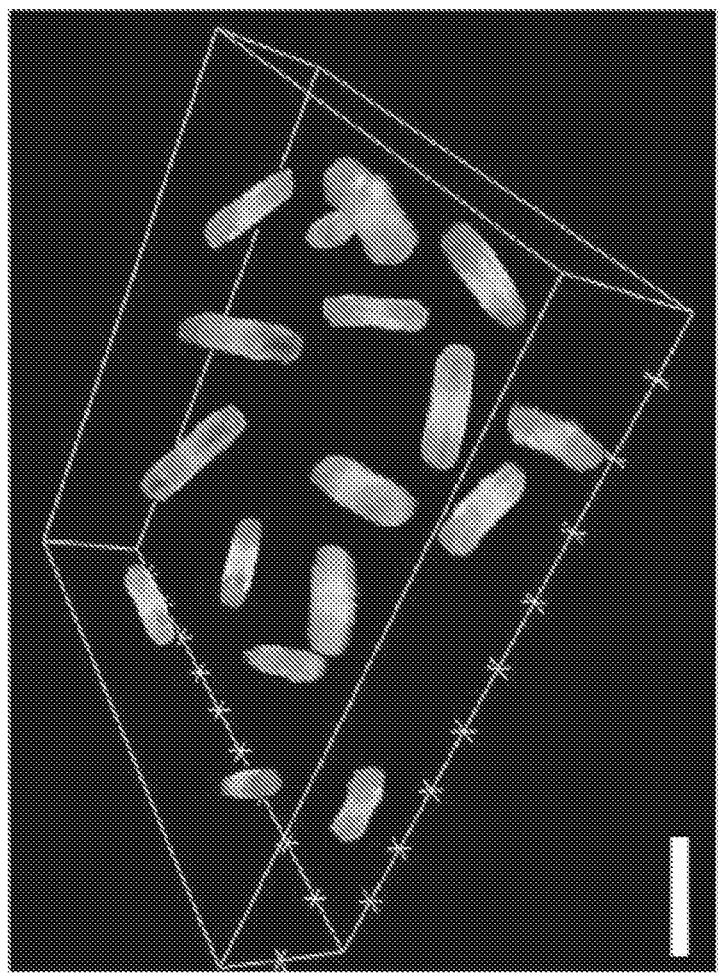
Figure 4E:
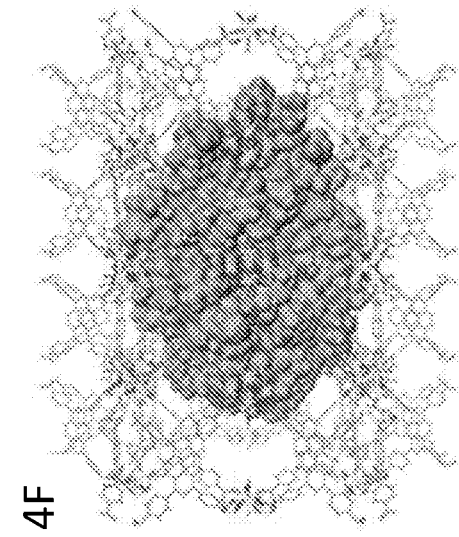
Figure 4F:
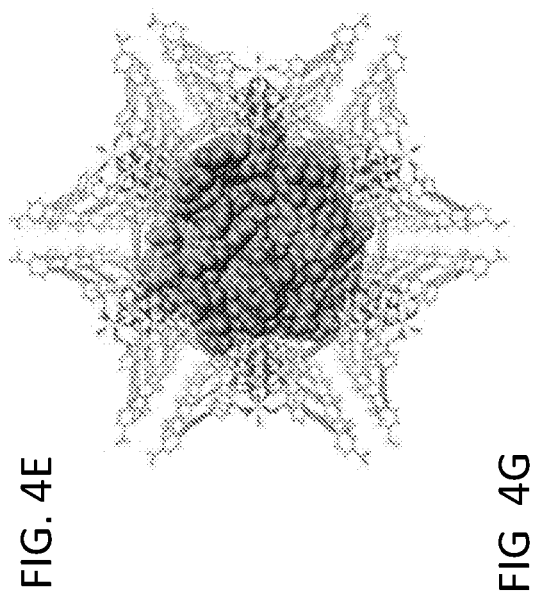
Figure 4G:
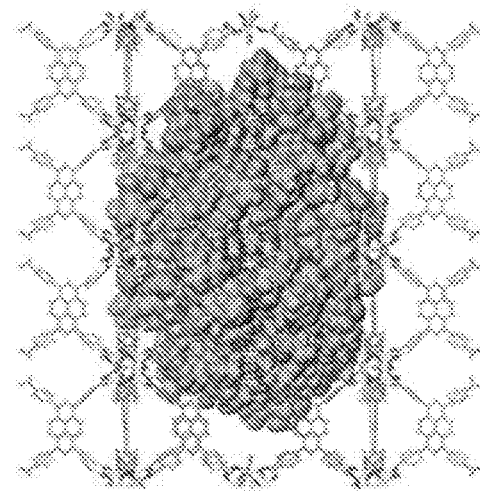
Figure 4H:
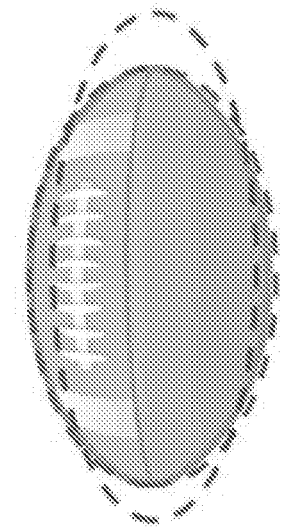

One property of MOF-encapsulated enzymes that had yet to be explicitly addressed was the permeability of the crystals to small molecule reactants after enzyme immobilization. It was reasoned that the hierarchical pore structure of NU-1000 would allow molecules of appropriate dimensions to diffuse into the interior of the crystal, even after enzyme encapsulation, either longitudinally via the triangular pore or laterally via the crystal windows. Molecules larger than either of these apertures should be excluded from the crystal due to blocking of the larger channels by cutinase. To test this idea, two dye molecules were chosen (FIG. 4B)—one with dimensions small enough to diffuse through the smaller apertures (fluorescein (1.0×0.8×0.5 nm, $\lambda_{ex}$=488 nm, $\lambda_{em}$=512 nm)) and one too large to do so (4,4',4",4"'-(porphine-5,10,15,20-tetrayl)tetrakis(benzoic acid) (1.6× 1.6×0.2 nm, $\lambda_{ex}$=405 nm, $\lambda_{em}$=640 nm)), and the ability of each dye to permeate empty versus Cut647-loaded NU-1000-10 µm using CLSM was compared. Both dyes had fluorescence emission maxima that lay well outside those of AlexaFluor-647. For empty NU-1000-10 µm, micrographs taken of samples immersed in solutions of fluorescein and porphyrin showed that both dyes could freely permeate the crystal. In the case of Cut647@NU-1000-10 µm, merged 3D reconstructions of z-stacks from the 633 nm (dye-labeled cutinase) and 488 nm (fluorescein) laser channels showed the presence of Cut647 and that fluorescein retained access to the whole of the matrix (FIG. 4C). In the case of the larger porphyrin dye (UV 405 nm laser channel), a size-exclusion effect was observed where the molecule was blocked from entering the interior of the crystal and resided primarily on the surface (FIG. 4D). This demonstrated that although the large, hexagonal channels of NU-1000 were blocked by encapsulated cutinase, a reactant small enough to fit into the smaller triangular channels could still freely diffuse in and out of the framework.

Given that the computational model suggested that the active site of cutinase would remain accessible after immobilization, a real-time in-situ CLSM experiment was performed on cutinase@NU-1000-10 µm following the addition of a small aliquot of resorufin butyrate (RB) to determine whether the enzyme was accessible and active. Enzymatic hydrolysis of RB by cutinase produced resorufin ($\lambda_{ex}$=500 nm, $\lambda_{em}$=593 nm), a highly fluorescent dye that can be used to monitor the catalytic activity of the encapsulated enzyme. When RB was added to a solid sample of cutinase@NU-1000-10 µm, the crystals of the MOF rapidly began to fluoresce at 593 nm throughout the crystal, indicating that the reactant not only reached the interior of the matrix but that the encapsulated cutinase was accessible and reactive there. As the reaction proceeded, the fluorescence intensity of resorufin in solution increased, suggesting that the product can quickly diffuse out of the channels of NU-1000. Control experiments using empty NU-1000-10 µm showed no increase in fluorescence over the course of the experiment, indicating the support had no catalytic activity of its own. To probe specifically the activity of enzymes sited in the MOF interior, a sample of NU-1000 was prepared containing active enzyme only in the interior of the crystal by treating NU-1000-10 µm with a 100 µM solution of cutinase for 2.5 hours followed by extensive washing. The sample was then placed in a 100 µM solution of catalytically inactive cutinase for 2 d to backfill the mesopores. In situ hydrolysis of resorufin butyrate was used to probe the enzyme accessibility and reactivity. Hydrolysis was found to still occur efficiently, indicating that reactant molecules could access cutinase not only on the MOF exterior but also in its crystalline interior.

Figure 5B:
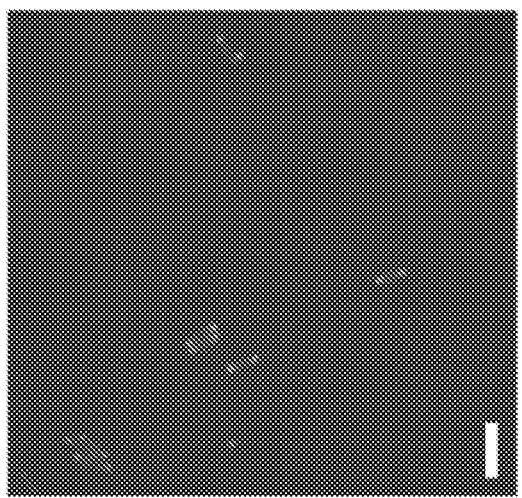
FIGS. 5A-5D show in-situ hydrolysis of resorufin by blocked cutinase@NU-1000.
Figure 5D:
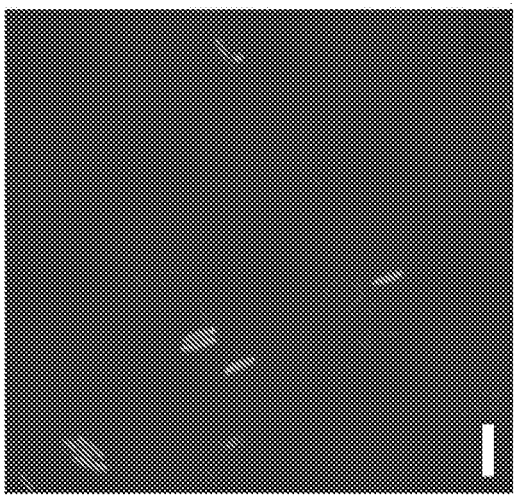
Figure 5A:
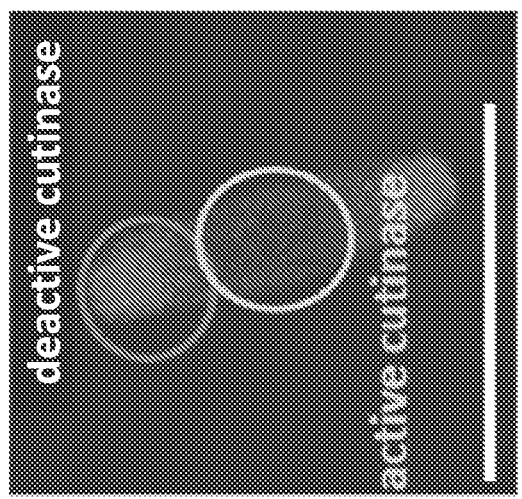
Figure 5C:
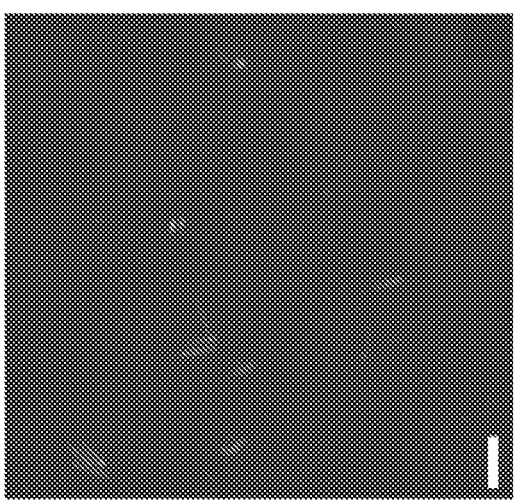
Figure 6A:
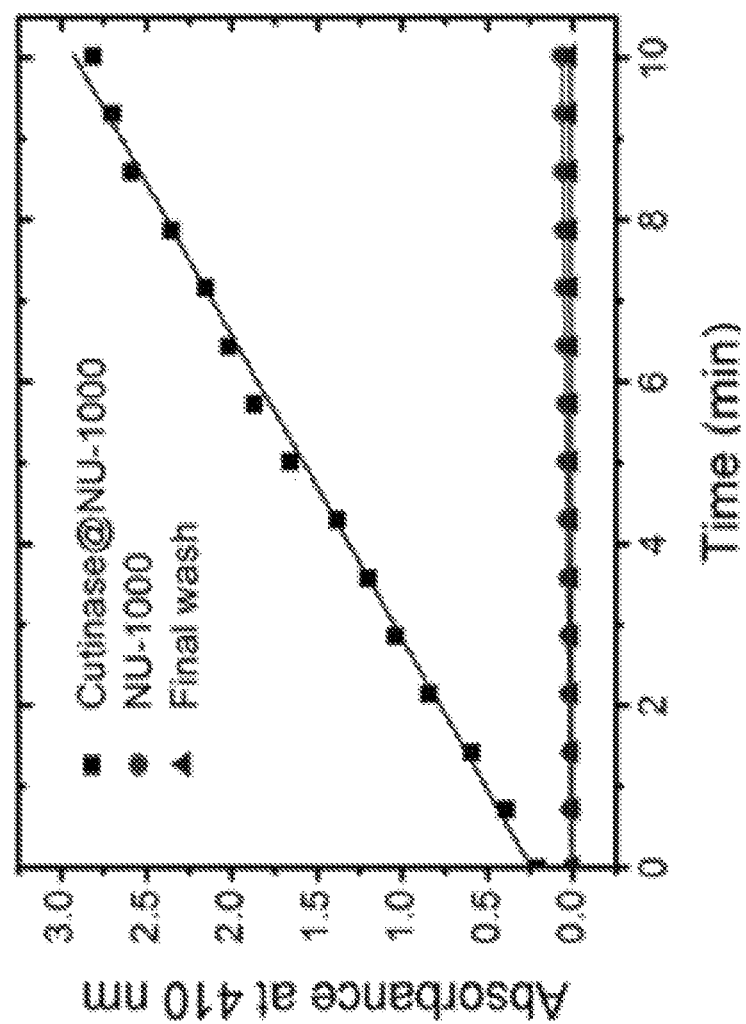
FIGS. 6A-6F show activity and stability assays.

FIG. 5A shows a CLSM image of a magnified image of a single NU-1000-10 µm crystal containing active cutinase blocked by deactivated cutinase. FIG. 5B shows a CLSM image of a magnified image of multiple crystals of NU-1000 showing active and deactivated cutinase similar to image in 7A. FIG. 5C shows in-situ hydrolysis of resorufin butyrate using cutinase@NU-1000 containing active and deactivated cutinase for 5 seconds. FIG. 5D shows in-situ hydrolysis of resorufin butyrate using cutinase@NU-1000 containing active and deactivated cutinase for 60 seconds in buffer solution at room temperature Activity and Stability of Immobilized Cutinase Before testing the activity and stability of immobilized cutinase, the hydrolysis of p-nitrophenyl butyrate (PNPB) was compared using cutinase@NU-1000, NU-1000, and the final solution used to soak cutinase@NU-1000 as catalysts (FIG. 6A). The results indicated there was no activity for NU-1000 and no active cutinase detectable in the final solution. To gain further insight into the influence of immobilization on activity, the enzyme kinetic parameters $k_{cat}$ and $K_M$ for free cutinase and cutinase@NU-1000-5 µm were determined for the hydrolysis of three representative substrates (esters offering different aliphatic chain lengths: p-nitrophenyl acetate (PNPA), p-nitrophenyl butyrate (PNPB), p-nitrophenyl octanoate (PNPO)).

TABLE 1

Hydrolysis of esters catalyzed by cutinase and cutinase@NU-1000a.

| Entry | Catalyst | R | $K_m$ (mM) | $k_{cat}$ (s$^{-1}$) | $k_{cat}/K_m$ (mM$^{-1}$ s$^{-1}$) |
|---|---|---|---|---|---|
| 1 | cutinase@NU-1000 | CH$_3$ | 0.8 | 5.88 × 10$^2$ | 6.93 × 10$^2$ |
| 2 | cutinase@NU-1000 | (CH2)$_2$CH$_3$ | 0.29 | 2.35 × 10$^3$ | 8.16 × 10$^3$ |
| 3 | cutinase@NU-1000 | (CH2)$_6$CH$_3$ | 0.12 | 2.35 × 10$^2$ | 1.90 × 10$^3$ |
| 4 | Free cutinase | CH$_3$ | 2.4 | 1.11 × 10$^3$ | 4.59 × 10$^2$ |
| 5 | Free cutinase | (CH2)$_2$CH$_3$ | 0.32 | 2.00 × 10$^3$ | 6.23 × 10$^3$ |
| 6 | Free cutinase | (CH2)$_6$CH$_3$ | 0.068 | 1.67 × 10$^2$ | 2.46 × 10$^3$ |

The results showed that immobilized cutinase had similar overall activity to free cutinase in solution. Next, the stability of cutinase@NU-1000-5 µm was compared relative to that of soluble cutinase, under several challenging conditions. As a measure of stability, the catalytic hydrolysis of a common esterase substrate p-nitrophenyl butyrate (PNPB) by the free and encapsulated enzyme was monitored (FIGS. 6B, 6C, 6D, and 6E) and the activity was compared in terms of turnover number (TON), as summarized in Table 2.

TABLE 2

Turnover number of hydrolysis of PNPB catalyzed by cutinase and cutinase@NU-1000 in different solvent.

| Entry | Catalyst | Solvent | Time (min) | TON, s−1 |
|---|---|---|---|---|
| 1 | cutinase@NU-1000 | buffer with detergent$^a$ | 15 | 2.35 × 10$^3$ |
| 2 | cutinase@NU-1000 | buffer without detergent | 30 | 2.13 × 10$^3$ |
| 3 | cutinase@NU-1000 | buffer with urea$^b$ | 60 | 2.24 × 10$^3$ |
| 4 | cutinase@NU-1000 | buffer with THF$^c$ | 60 | 1.06 × 10$^3$ |
| 5 | Free cutinase | buffer with detergent$^a$ | 15 | 2.00 × 10$^3$ |
| 6 | Free cutinase | buffer without detergent | 30 | 1.13 × 10$^3$ |
| 7 | Free cutinase | buffer with urea$^b$ | 60 | 3.82 × 10$^2$ |
| 8 | Free cutinase | buffer with THF$^c$ | 60 | 1.87 × 10$^2$ |

Figure 6B:
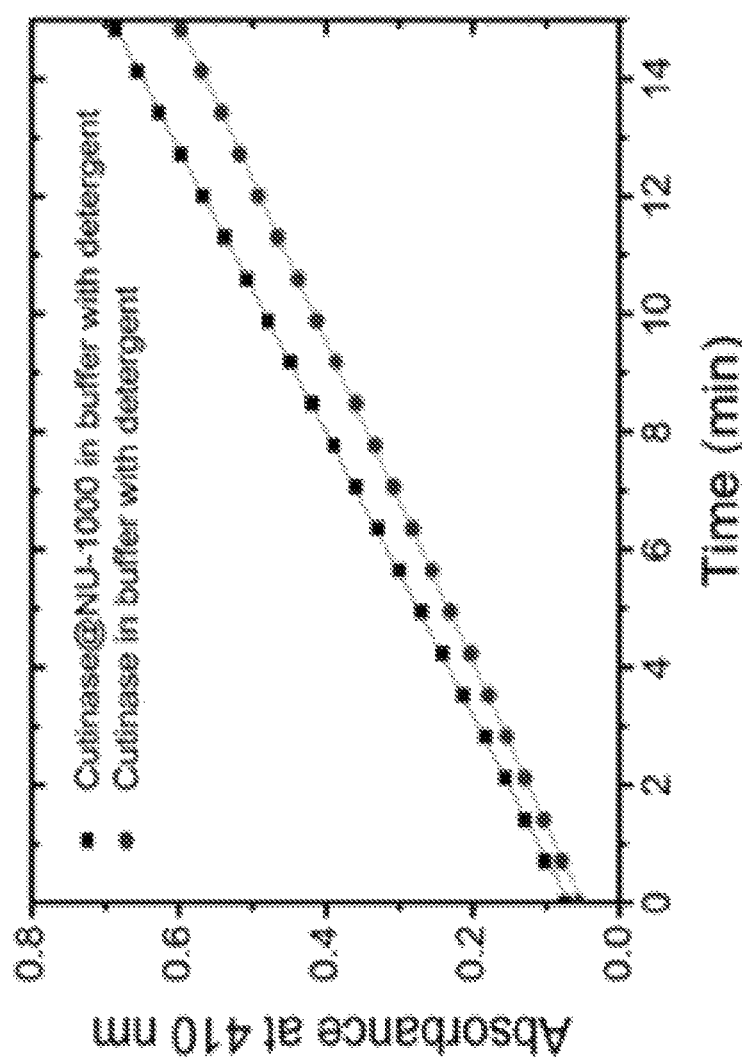
Figure 6C:
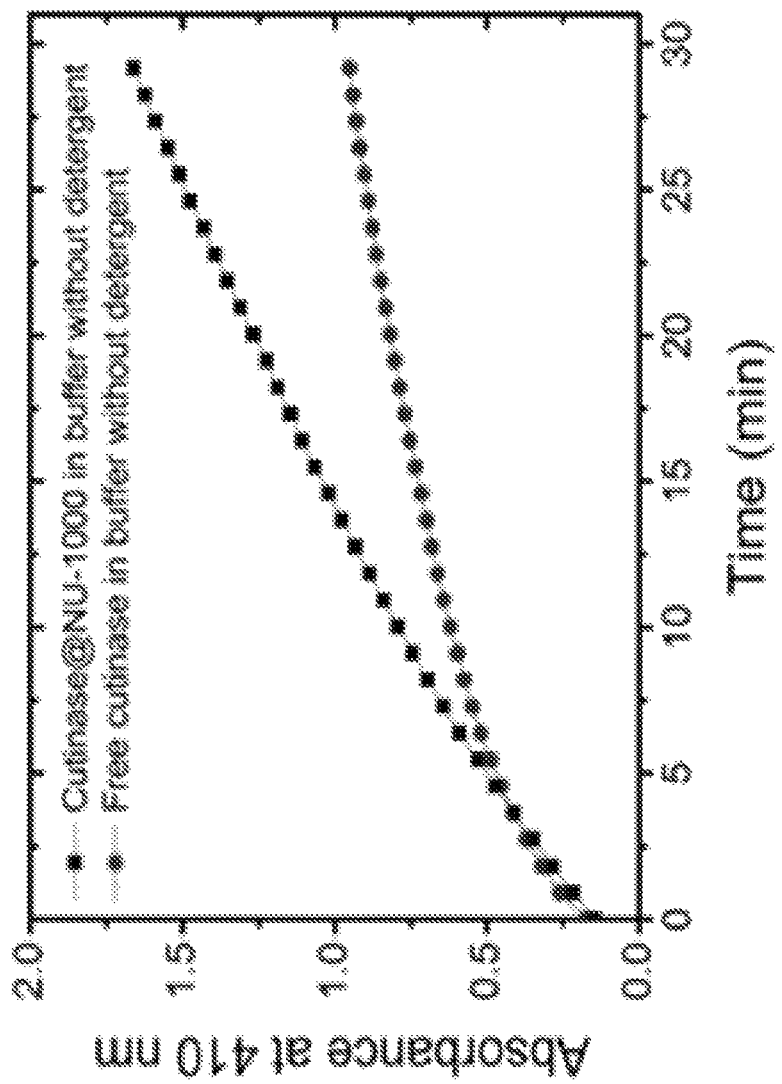
Figure 6D:
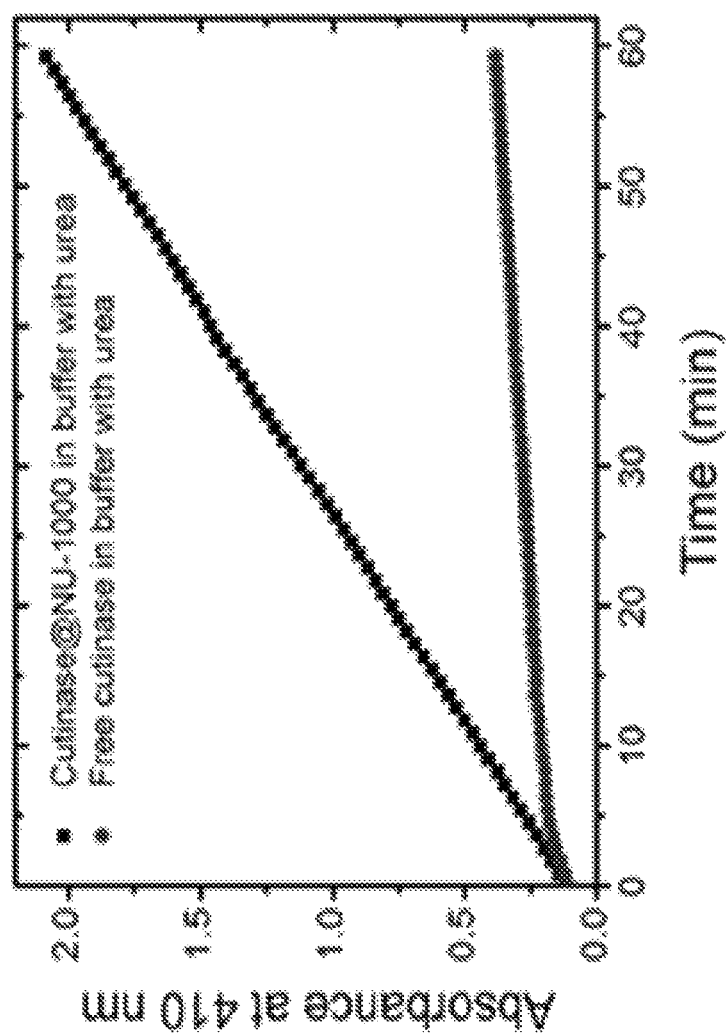
Figure 6E:
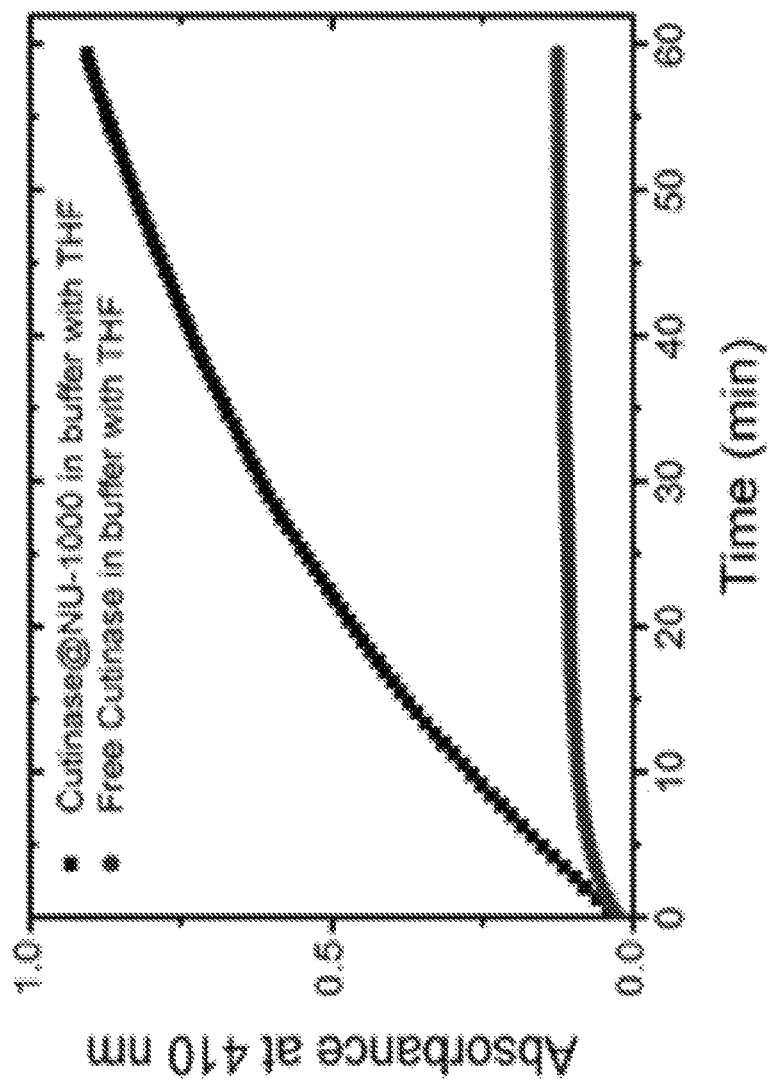
Figure 6F:
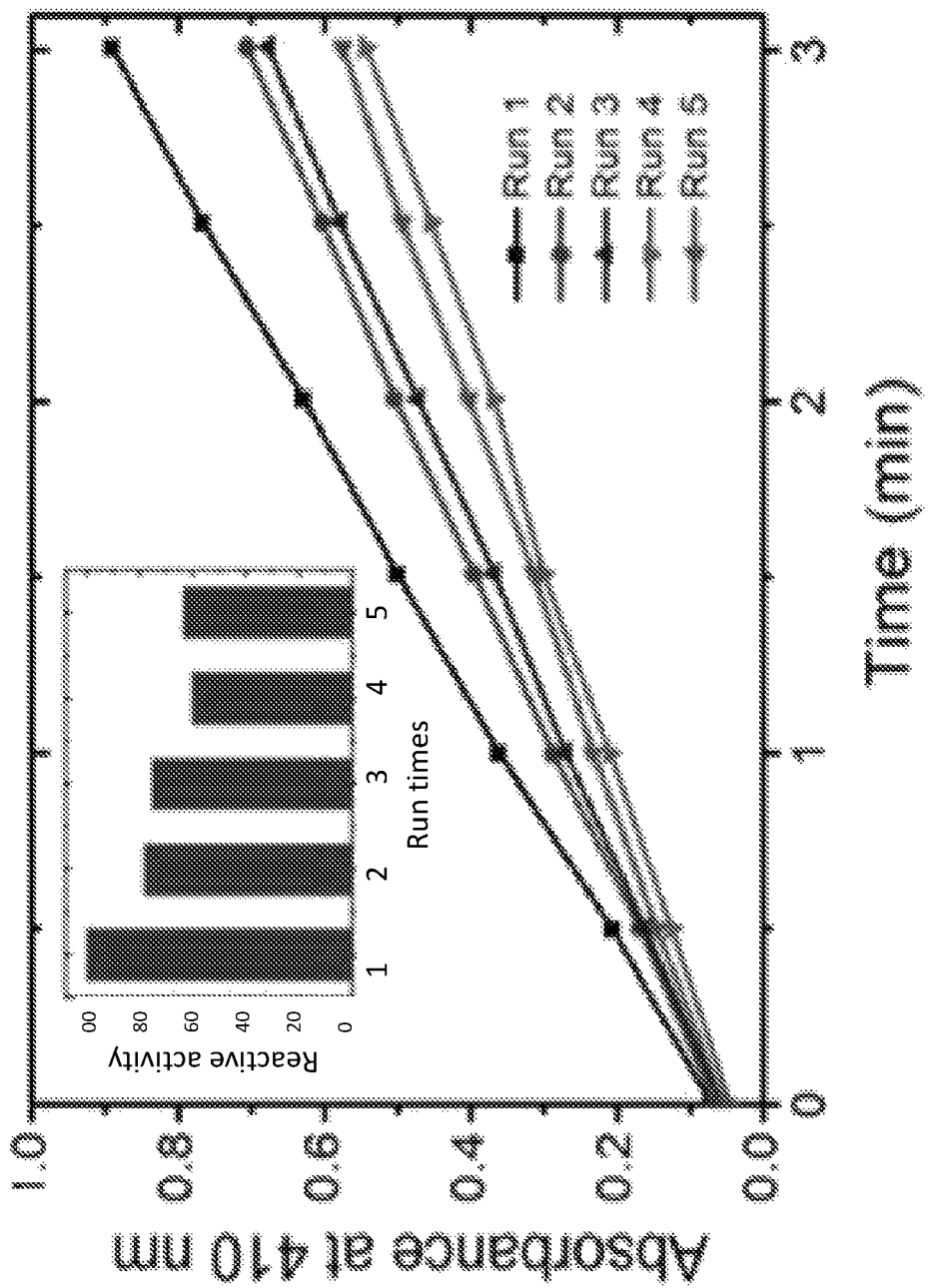

The activity was monitored: a) in detergent-containing buffer, b) in detergent-free buffer, and also in buffers containing c) the denaturant urea, or d) the organic solvent tetrahydrofuran (THF). Esterases like cutinase that also hydrolyze lipids are known to show protein concentration dependent aggregation in the absence of detergents or stabilizing additives upon reaction with hydrophobic substrates. In the buffer containing detergent, cutinase@NU-1000-5 µm and free cutinase showed comparable catalytic performance (FIG. 6B). In buffer without detergent, however, solution-phase cutinase gradually lost its catalytic activity, while cutinase@NU-1000-5 µm maintained turnover (FIG. 6C). In 30 minutes, the TON of cutinase@NU-1000-5 µm was almost twice as much as that of free cutinase. In buffer solution containing urea (560 mM), soluble cutinase was completely deactivated after 5 min; in contrast, the catalytic activity of cutinase@NU-1000-5 µm was unchanged after 60 min (FIG. 6D). The TON for cutinase@NU-1000-5 µm was almost 5 times that of free cutinase in 60 minutes. Similarly, in a buffer solution containing 2.5% THF, free cutinase was rapidly deactivated (8 min), while cutinase@NU-1000-5 µm was little affected (FIG. 6E). Under these conditions, the TON for cutinase@NU-1000-5 µm was still 5 times that of free cutinase in 60 minutes. Finally, the stability of the complex to repeated reaction was tested by following the hydrolysis of 300 µm PNPB catalyzed by 20 µg cutinase@NU-1000-5 µm over 5 reaction cycles. After each cycle, the complex was isolated by centrifugation, washed extensively with buffer and subjected to another round of reaction. After five cycles, around 60% of the catalytic activity of cutinase@NU-1000-5 µm was retained (FIG. 6F).

Figure 7A:
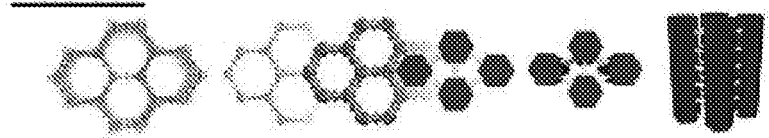
FIGS. 7A-7C show active site accessibility of immobilized cutinases in MOFs.
Figure 7B:
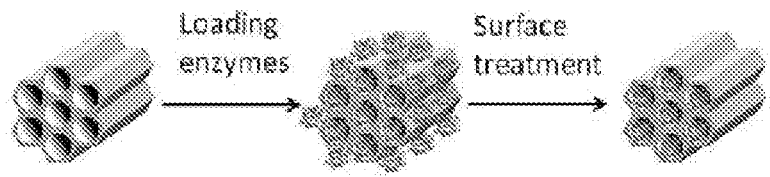
Figure 7C:
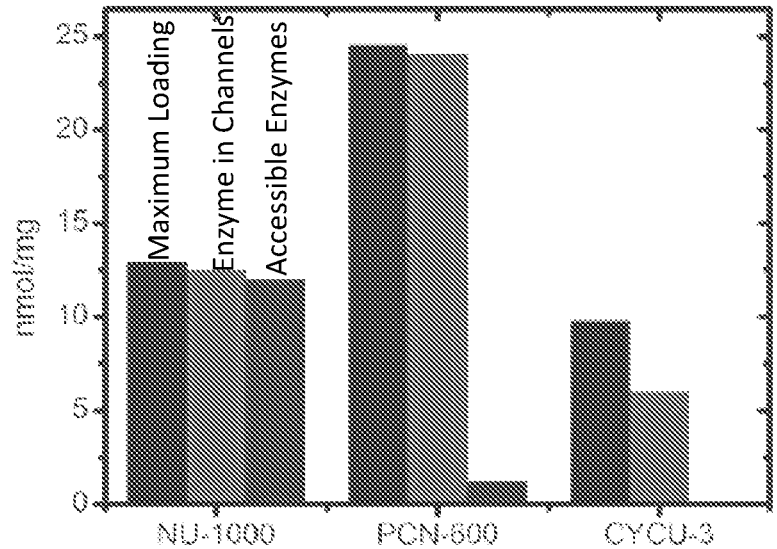
Figure 8A:
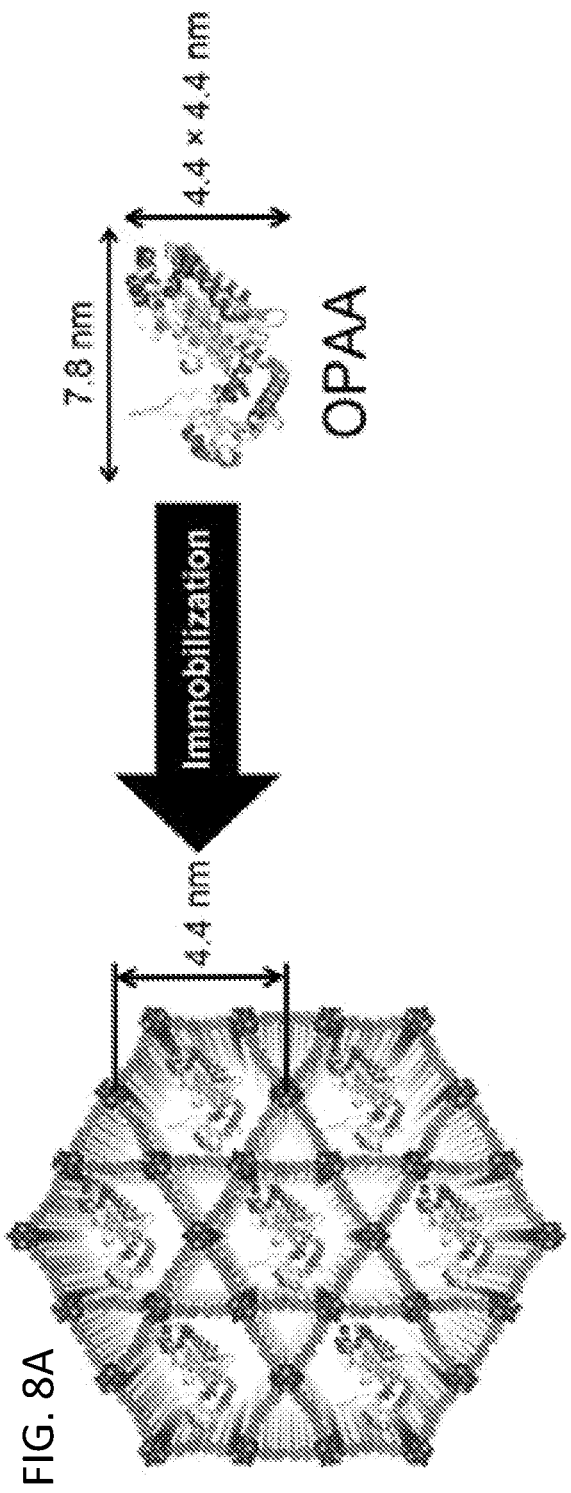
FIG. 8A shows immobilization of OPAA in the mesoporous channels of PCN-128y.
Figure 8B:
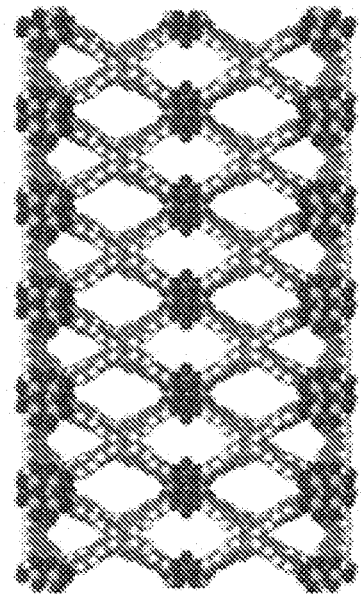
FIG. 8B is a side view of PCN-128y with open windows between mesoporous channels and microporous channels.
Figure 8C:
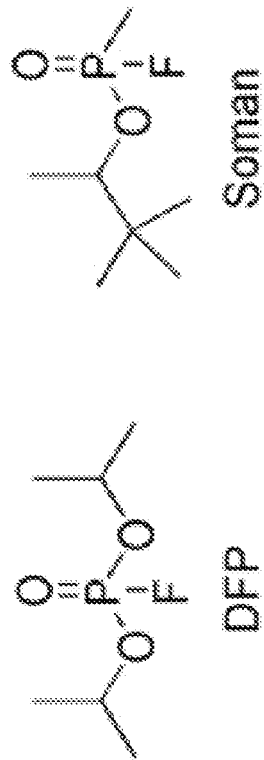
FIG. 8C shows chemical structures of nerve agents used in the Example.

Comparing the Accessibility of Cutinase Immobilized in NU-1000 Versus Other MOF Supports To investigate the role of the hierarchical structure of NU-1000 for enzyme encapsulation applications, the activity of cutinase immobilized in representative channel-type mesoporous MOFs was compared. CYCU-3 and PCN-600 were chosen as control MOFs to compare with NU-1000 (FIG. 7A). All of these channel-type MOFs possess mesopores approximately 3.0 nm in diameter, but differ in the identity of the metal nodes, organic linkers, and connectivity, resulting in different channel systems and accessibility within these frameworks. PCN-600 contains only hexagonal mesopores, which can, however, communicate via channel windows. CYCU-3 features a hierarchical micro-mesopore architecture similar to NU-1000; however, the walls of the channels in CYCU-3 are too condensed to allow reactant to diffuse freely between neighboring channels. In contrast, NU-1000 has open windows between the microporous and mesoporous channels, allowing for free communication between the different sized pores. To observe the diffusion of cutinase into PCN-600 and CYCU-3, micro-sized crystals of each MOF were prepared for comparison with NU-1000-5 µm and the loading of Cut647 in these MOFs was followed by CLSM over 5 days. The diffusion behavior of cutinase in all three MOFs was similar, where cutinase slowly diffused from the two ends of each crystal into the center of the MOF. This demonstrated the generality of immobilization of enzymes into channel-type MOFs. To compare enzyme accessibility in CYCU-3, PCN-600 and NU-1000, nano-sized crystals of these three MOFs were synthesized to ensure that the rate of diffusion was maximized and that the maximum loading of cutinase in each framework was achieved within 24 hours. The final amounts of cutinase encapsulated by nanosized NU-1000, CYCU-3, and PCN-600 were 12.9 nmol/mg, 9.8 nmol/mg, and 24.5 nmol/mg, respectively, as determined by ICP-OES. These findings were broadly consistent with the available mesopore volumes, i.e. ~0.95 cm$^3$/g for NU-1000, versus 0.90 cm$^3$/g for CYCU-3 and 1.80 cm$^3$/g for PCN-600. To ensure complete removal of any enzyme immobilized on the external surface of each nanosized MOF prior to accessibility testing, the proteolytic agent trypsin was used to decompose cutinase on the outer surface (FIG. 7B). The dimensions of trypsin are similar to those of cutinase and thus cutinase sited within the MOF should not be decomposed by this process. The percentages of cutinase removed from the exteriors of NU-1000, CYCU-3, and PCN-600 were 3%, 39%, and 2%, respectively (FIG. 7C). The comparatively large percentage of cutinase removed from CYCU-3 can be attributed to its comparatively poor stability in water, and therefore CYCU-3 was not studied further.

To accurately evaluate the accessibility of cutinase after immobilization in NU-1000 versus PCN-600, an organophosphorus ester with a fluorescent resorufin group was synthesized and used as an active-site titrant. The titration results show that in PCN-600, only 1.5 nmol/mg (6% of the total amount) of cutinase encapsulated in the channels shows activity. Given that PCN-600 contains only hexagonal mesoporous channels, this result was not surprising since many of the mesopores are expected to be blocked by encapsulated cutinase leaving little room for reactant diffusion. On the other hand, in NU-1000, 93% of the encapsulated cutinase was found to be accessible and catalytically active (FIG. 7C). This demonstrates that in addition to the importance of hierarchical pore structure for reactant diffusion, the presence of windows between the pores is key to achieving enzyme accessibly and hence enzyme turnover in a solid support.

CONCLUSION

By immobilizing an enzyme in the water-stable, hierarchical, channel-type MOF NU-1000, the enzyme could be stabilized in the array of larger channels, while reactants and products could diffuse through the array of smaller channels in the framework. This integration of large and small channels—with the windows that connect them throughout the crystal—allowed the MOF to be optimized for both binding and stabilization of the enzyme and diffusion of reactants and products. It has been shown that NU-1000 is an excellent support for stabilizing the encapsulated enzyme in varying media such as THF and urea, whereas the free enzyme degrades rapidly under these conditions. For optimization of enzyme activity, the degree of channel hydrophobicity in NU-1000 has been found to be highly tunable, as has the (bio)chemical composition of the channel lining, e.g. fluorocarbons, polypeptides, organic acids and bases, luminescent dyes, and even metal-sulfide clusters. The tunability of MOFs and their ability to stabilize enzymes in an accessible fashion makes them suitable for the immobilization of a vast array of useful enzyme catalysts.

Experimental Procedures

Materials.

Zirconyl chloride octahydrate ($ZrOCl_2.8H_2O$), benzoic acid ($C_6H_5COOH$), aluminum chloride nonahydrate ($AlCl_3.9H_2O$), N,N-dimethylformamide (DMF), Triflouroacetic acid (TFA), 4,4'-Stilbenedicarboxylic acid ($H_2SDC$), (p-nitrophenyl acetate (PNPA), p-nitrophenyl butyrate (PNPB), p-nitrophenyl octanoate (PNPO), diethyl butylphosphonate, tris(hydroxymethyl)aminomethane (TRIS), citric acid, fluorescein, resorufin butyrate, and resorufin sodium salt were purchased from Sigma-Aldrich and used as received. Fe(III) meso-Tetra(4-carboxyphenyl)porphine chloride (FeTCPP) and meso-Tetra(4-carboxyphenyl) porphine (TCPP) were purchased from Frontier Scientific and used without further purification. Iron(III) nitrate nonahydrate ($Fe(NO_3)_3.9H_2O$) and sodium acetate trihydrate ($NaOOCCH_3.3H_2O$) were purchased from Alfa Aesar. AlexaFluor®647 dye was purchased from Life Technologies (Thermo Fisher Scientific). The ligand 1,3,6,8-tetrakis(p-benzoic acid)pyrene ($H_4TBAPy$) was synthesized following the published procedure. (See, Mondloch, J. E., et al. (2013). Vapor-Phase Metalation by Atomic Layer Deposition in a Metal-Organic Framework. *J. Am. Chem. Soc.* 135, 10294-10297.) NU-1000, CYCU-3, precursor [$Fe_3O(OOCCH_3)_6OH$], and PCN-600 were synthesized following published procedures. (See, Lo, S. H. (2013). A mesoporous aluminium metal-organic framework with 3 nm open pores. *J. Mater. Chem. A* 1, 324-329; Wang, K., et al. (2014). A Series of Highly Stable Mesoporous Metalloporphyrin Fe-MOFs. *J. Am. Chem. Soc.* 136, 13983-13986; Li, P., et al. (2015). Synthesis of nanocrystals of Zr-based metal-organic frameworks with csq-net: significant enhancement in the degradation of a nerve agent simulant. *Chem. Commun.* 51, 10925-10928.) *F. solani pisi* cutinase (MW=22.5 kDa) was made and purified according to a protocol described elsewhere. (See, Chen, S., et al. (2013). Cutinase: characteristics, preparation, and application. *Biotechnol. Adv.* 31, 1754-1767). Buffered aqueous solutions of cutinase ($10^{-5}$-$10^{-7}$M) were prepared at pHs of 6 (citric acid buffer) and 7.4 (tris-HCl buffer).

Powder X-Ray Diffraction.

Powder X-ray diffraction data were collected on a Rigaku model ATX-G diffractometer equipped with a Cu rotating anode X-ray source.

Gas Adsorption Measurements.

$N_2$ sorption isotherm measurements were performed on a Micromeritics Tristar II 3020 (Micromeritics, Norcross, Ga.) at 77 K. Between 30 and 100 mg of material was used for each measurement.

Scanning Electron Microscopy.

Scanning electron microscopy images were taken using a Hitachi SU8030 or a Hitachi S4800-II at the EPIC facility (NUANCE Center-Northwestern University).

NMR Spectroscopy.

$^1H$ and $^{13}C$ NMR spectrum were recorded on a Bruker 500 FT-NMR spectrometer (500 MHz for $^1H$ and 126 MHz for $^{13}C$) and $^{31}P$ NMR spectrum was recorded on an Agilent 400 FT-NMR spectrometer (400 MHz) at IMSERC (Integrated Molecular Structure Education and Research Center) of Northwestern University.

Electrospray Ionization Mass Spectrometry.

Electrospray ionization mass spectrometry (ESI-MS) data was recorded on a Bruker AmaZon SL Ion Trap at IMSERC (Integrated Molecular Structure Education and Research Center) of Northwestern University.

Zeta Potential Measurement.

Zeta potential of samples was measured using a Malvern Zetasizer Nano ZS. NU-1000 samples were made up in 18.2 MΩ deionized water at a concentration of 0.1 mg/mL and sonicated for 15 min. The pH from 3 to 8 of the solution was manually adjusted by the addition of 0.1 M HCl or NaOH to 10-15 mL of the suspension before the zeta potential was measured.

ICP-OES Analysis.

Quantification of zirconium (Zr) and sulfur (S) was accomplished using ICP-OES of acid digested samples using individual Zr and S elemental standards prepared by diluting a 10000 ppm certified Zr standard and 10000 ppm certified S standard (Ricca chemical company) to 1.5625, 3.125, 6.25, 12.5, 25, and 50 ppm concentrations with 3% nitric acid (v/v), up to a total sample volume of 10 mL. ICP-OES was performed on a computer-controlled (QTEGRA software v. 2.2) Thermo iCap 7600 Duo ICP-OES (Thermo Fisher Scientific, Waltham, Mass., USA) operating in standard mode and equipped with a SPRINT valve and CETAC 520 autosampler (Teladyne CETAC, Omaha, Nebr., USA). Each sample was acquired using a 5 sec sample loop fill (4 mL sample loop), 4 sec loop rinse plus a 4 sec extra loop rinse [Rinse was 2% $HNO_3$ (v/v) and 2% HCl (v/v)]. Samples were analyzed for Zr in radial view (339.198, 343.823, and 327.305 nm wavelengths) and Sin axial view (180.731, 182.034, and 182.624 nm wavelengths) with 3 replicates and an exposure time of 20 sec. Instrument performance is verified weekly via a performance report (passing manufacturer specifications). The enzymes loading is determined by comparing the experimental Zr:S ratio to the theoretical ratio given by the stoichiometry of Zr in the MOF to the number of cysteine thiols present in cutinase (Zr:S=96:1).

General Procedure for Kinetic Study of Hydrolysis Reaction:

Hydrolysis profiles of p-nitrophenyl acetate (PNPA), p-nitrophenyl butyrate (PNPB), p-nitrophenyl octanoate (PNPO) by using cutinase or immobilized cutinase were recorded on a Beckman Coulter DU 640 spectrophotometer. Stock solutions of the esters were prepared using DMSO as a diluent. NU-1000 immobilized cutinase suspensions and free cutinase solution concentrations were adjusted to give similar initial rate profiles and time course length prior to treatment with various substrate concentrations. The reactions were conducted in a 1 mL cuvette containing 10 µL of the ester stock solution, 10 µL enzyme solution/MOF-enzyme complex suspension, and 980 µL TBS+0.1% Triton-X100. Absorbance data at 410 nm (p-nitrophenyl absorption) were collected versus time. Michealis parameters for the enzyme substrate reactions were obtained using Lineweaver-Burke analysis of initial rate data.

Stability and Recyclability Test.

The stability of 5 nM cutinase and 5 nM immobilized cutinase in NU-1000 were compared using PNPB as a reactant in different media. For the recycling studies with NU-1000 immobilized cutinase, the reaction was performed with 300 µM PNPB by 20 µg cutinase@NU-1000-5 µm in TRIS buffer at pH 7 and room temperature. After reaction, the mixture was centrifuged and the supernatant was separated. The resulting solid was washed three times with TRIS buffer to remove any soluble residue. The recovered NU-1000 immobilized cutinase was used for the next reaction by adding the same amount of reactant and buffer. The procedure was repeated 5 times as describe above. The relative activity was calculated as a ratio of enzyme activity at any given cycle versus the enzyme activity during the first cycle.

Labeling Cutinase with Fluorescent Dye.

AlexaFluor-647 labeled cutinase (Cut647) was prepared by reacting cutinase (100 µM) with 1.2 equivalents of an AlexaFluor-647-(ethyl-p-nitrophenyl)-phosphonate conjugate followed by purification of the labeled protein by size-exclusion chromatography (SEC). (See, Modica, J. A., et al. (2012). Modular assembly of protein building blocks to create precisely defined megamolecules. *ChemBioChem* 13, 2331-2334). This rendered the enzyme catalytically inactive. AlexaFluor-647 was chosen due to the relative insensitivity of its fluorescence intensity and quantum yield to environmental conditions, and excitation/emission maxima (650 nm/665 nm) that occur far outside that of the pyrene struts (390 nm/471 and 529 nm) used to construct the MOF. In the CLSM experiment using deactivated cutinase (Cut647), the complete loss of hydrolysis activity was confirmed by PNPB activity assay.

Immobilization of Cutinase in MOFs.

2 mg of activated MOF (NU-1000, PCN-600, or CYCU-3) was added to 1 mL of deionized water and sonicated for 5 min until a uniform suspension was formed. The well dispersed solid was isolated by centrifugation at 15000 rpm for 1 min and the supernatant was decanted. The solid was then suspended in a solution of cutinase (500 µL, 100 µM) in TBS, pH 7.4 for a given time (1 day for nanosized MOF and 5 days for microsized MOF) at 25° C. After that, the MOF-cutinase composite was isolated by centrifugation at 15000 rpm for 1 min, and the supernatant was removed. The solid was further washed with TBS containing 0.1% Triton-X100 5 times and soaked in TBS buffer solution before further experiments.

Confocal Laser Scanning Microscopy Analysis.

NU-1000-10 µm crystals are used for all confocal laser scanning microscopy (CLSM) studies to monitor the uptake of cutinase and the distribution of enzymes throughout the matrix. (See, Han, S., et al. (2012). Transport into metal-organic frameworks from solution is not purely diffusive. *Angew. Chem. Int. Ed.* 51, 2662-2666.) Fluorescence was examined, applying CLSM on a Leica TCS SPS. The Ar laser was set to 5%. Bit depth was set to 12 to achieve 4096 grey levels intensity resolution. Laser line 633 with 3% laser power was used to visualize AlexaFluor-647 dye labeled cutinase on NU-1000. Quantitative analyses were performed employing the Leica LAS-AF image analysis, where a Region-of-interest (ROI) was manually selected using line tool. In a selected ROI, measurements of the relative mean intensity of the fluorescence signals were taken by the Leica LAS-AF image analysis program. The Mark and Find panel was used to locate the position (x, y, and z coordination) of the same single crystal of NU-1000 during the test at different time points. The loading process of Cut647 into a single crystal of NU-1000 was monitored using in-situ CLSM. The submerged NU-1000 crystals were first placed into a solution with TRIS buffer. Two-dimensional (xy) concentration profiles of Cut647 taken at a fixed z depth (corresponding to the center layer) within the crystal of NU-1000 were acquired on a Leica-SP5 CLSM once Cut647 was added to the solution. During imaging, the laser power was set as low as possible (5%, 1 mW HeNe laser) to avoid fluorescence saturation and to minimize photo bleaching. To obtain time-dependent Cut647 concentration profiles for the MOF and avoid decay of the fluorophore caused by repeated illumination by the laser, images were acquired only at given time intervals: 2 min, 60 min, 240 min, 960 min, 1440 min, 2880 min, 4320 min, and 7200 min. Using the line tool in Image J$^{51}$, fluorescence intensity profiles along the middle of an NU-1000 crystal for each sample were obtained and plotted as a function of the length of the crystal vs. time.

Titration of Active Sites for Cutinase and Immobilized Cutinase in MOFs.

The titration experiments were performed using the Molecular Devices Gemini EM Fluorescence/Chemiluminescence Plate Reader. A calibration curve relating cutinase activity to the intensity of liberated resorufin was generated by treating cutinase at several concentrations (8 µM, 6 µM, 4 µM, 2 µM, 1 µM, and 500 nM) in MES-saline buffer (20 mM MES, 150 mM NaCl, pH 6.0) with a solution of 5 µM resorufin phosphonate (RP) in IVIES-saline at 37° C. Steady-state fluorescence intensities at the completion of the reaction were plotted vs. enzyme concentration and fitted to a straight line to generate the calibration curve. For the titration experiments, 5 µg of nanosized empty NU-1000, empty PCN-600, cutinase@NU-1000 and cutinase@PCN-600 were treated with RP (5 µM) at 37° C. and the fluorescence intensity monitored for 5 hr. Background-subtracted steady state fluorescence values for each of the experimental samples were then compared to the calibration curve to yield the concentration of cutinase active sites present in the MOF-enzyme samples.

Supplemental Experimental Procedures

Numerical One-Dimensional Model of CUT647 Diffusion into NU-1000 Crystal

To extract a diffusion coefficient from our experimental CLSM data, the data were fit to the analytical solution of the one-dimensional diffusion equation:

$$\frac{\partial C}{\partial t} = D \frac{\partial^2 C}{\partial x^2} \tag{1}$$

where D is the diffusion coefficient, t is time, x is the dimension along the diffusion direction, and c is the normalized fluorescence intensity used as a proxy for concentration. Since the fluorescence values at the inside boundaries of the crystal ($X_0$ and $X_0+L$) do not instantaneously reach equilibrium, a solution was sought with boundary conditions that account for a surface barrier:

$$\frac{\partial c(x_0, t)}{\partial x} = \alpha [c(x_0, t) - u_0] \quad (2)$$

$$\frac{\partial c(x_0 + L, t)}{\partial x} = \alpha [u_0 - c(x_0 + L, t)] \quad (3)$$

where $u_0$ is the final equilibrium value of the fluorescence signal inside the crystal at long time scales and $\alpha$ is a scalar constant.

Initially, there is no fluorescently-labeled cutinase inside of NU-1000, so the following initial conditions were used:

$$c(x,0)=0 \text{ for } x_0 < x < x_0+L \quad (4)$$

$$c(x,0)=u_0 \text{ for } x < x_0 \quad (5)$$

$$c(x,0)=u_0 \text{ for } x > x_0+L \quad (6)$$

For each data set, four fitting parameters unique to that data set were used in addition to a global fitting parameter as described below. The solution that satisfied the diffusion equation along with the boundary and initial conditions could be found using an eigenvalue approach. (See, Dennery, P., and Krzywicki, A. (1996). *Mathematics for physicists*. (Courier Corporation).) The following solution applied to our particular system:

$$c(x, t) = \sum_{n=1}^{\infty} a_n \exp(-\lambda_n^2 Dt)\left(\sin(\lambda_n x) + \frac{\lambda_n}{\alpha \cos(\lambda_n X)}\right) \quad (7)$$

where the coefficients $\alpha_n$ are defined by:

$$a_n = \frac{2\alpha^2}{L(\alpha^2 + \lambda_n^2) + 2\alpha}(-u_0)\left[\frac{1-\cos(\lambda_n L)}{\lambda_n} + \frac{\sin(\lambda_n L)}{\alpha}\right] \quad (8)$$

and are eigenvalues of the function $$\tan \lambda L = \frac{2\alpha\lambda}{\lambda^2 - \alpha^2} \quad (9)$$

The fitting parameters were the equilibrium fluorescence value ($u_0$), a surface barrier coefficient ($\alpha$), and two parameters ($x_0$, L) used to define the crystal boundaries. These 4 parameters were fit for each data set separately. In addition, a global diffusion coefficient (D) assumed to be constant for all data sets was fitted.

The parameters were optimized by minimizing the mean squared error between the experimental and simulated concentration profiles using a Nelder-Mead simplex algorithm. (See, Nelder, J. A., and Mead, R. (1965). A simplex method for function minimization. *Computer J.* 7, 308-313.) For computational efficiency, only the first 200 terms of the infinite sum were used.

The optimal value for the diffusion coefficient of cutinase in NU-1000 crystals was found to be $2\times10^{-13}$ cm$^2$s$^{-1}$.

In Silico Modeling of Structure of Cutinase@NU-1000

To gain more insight into how the cutinase fits inside the hexagonal channels of NU-1000, molecular mechanics calculations were used. A section of NU-1000 was modeled with a length of six hexagonal rings forming the mesoporous channels with six peripheral triangular channels along the z axis. In these calculations, Materials Studio was used to perform energy minimizations based on classical molecular mechanics. (See, "Material Studio"; Accelrys Software Inc.: San Diego, San Diego, Ca 92121, USA, 2001-2011.) The initial atomic coordinates of NU-1000 were taken from published data. (See, Mondloch, J. E., et al. (2013). Vapor-Phase Metalation by Atomic Layer Deposition in a Metal-Organic Framework. *J. Am. Chem. Soc.* 135, 10294-10297.) The most stable arrangement of terminal aquo and hydroxo groups on the Zr-oxide nodes was obtained from recent work by Planas et al. (See, Planas, N., et al. (2014). Defining the Proton Topology of the Zr6-Based Metal-Organic Framework NU-1000. *The J. Phys. Chem. Lett.* 5, 3716-3723.) The atomic coordinates for cutinase were obtained from the protein data bank with the ID 1CEX. The Universal Force Field (UFF) was used to define all bonded and non-bonded interactions in the system. (See, Rappé, A. K., Casewit, C. J., Colwell, K. S., Goddard Iii, W. A., and Skiff, W. M. (1992). UFF, a full periodic table force field for molecular mechanics and molecular dynamics simulations. *J. Am. Chem. Soc.* 114, 10024-10035.) The pore model and the enzyme were treated as flexible except for the Zr atoms in NU-1000 metal cluster. Twenty minimization calculations were considered from different initial configurations of cutinase inside the pore model to reasonably cover all possible preferential sites. The geometry of each configuration was optimized using the smart algorithm in the Forcite module of Materials Studio.

The model revealed that the cutinase atoms came into close contact with the NU-1000 channel walls and the enzyme tightly fit in (only) the hexagonal channels. Interestingly, it was shown that the encapsulated enzyme could only reside in the channel when its longer axis was aligned with the direction of the hexagonal channels.

The steric accommodation was reflected in how the enzyme shrank to avoid congestion with the pore walls. The effects of solvent water molecules were not accounted for in the minimization calculations.

Synthesis of MOFs with Different Crystal Size

Solution A:

970 mg (3.00 mmol) of ZrOCl$_2$.8H$_2$O and 16.0 g (131 mmol) of benzoic acid were dissolved in 80 mL of DMF in a 100° C. oven.

Solution B:

200 mg (0.300 mmol) of the 1,3,6,8-tetrakis(p-benzoic acid)pyrene (H$_4$TBAPy) ligand was dissolved in 80 mL of DMF in a 100° C. oven.

10 μm NU-1000:

96 mg of ZrOCl$_2$.8H2O (0.30 mmol) and 2700 mg (22 mmol) of benzoic acid were mixed in 8 mL of DMF (in a 6-dram vial) and ultrasonically dissolved. The clear solution was incubated in an oven at 100° C. for 1 h. After cooling down to room temperature, 40 mg (0.06 mmol) of H4TBAPy was added to this solution and the mixture was sonicated for 20 min. The yellow suspension was heated in an oven at 120° C. for 48 h. After cooling down to room temperature, yellow polycrystalline material was isolated by filtration and washed with DMF and subsequently activated with HCl.

5 μm NU-1000:

96 mg of ZrOCl$_2$.8H$_2$O (0.30 mmol) and 2700 mg (22 mmol) of benzoic acid were mixed in 8 mL of DMF (in a 6-dram vial) and ultrasonically dissolved. The clear solution was incubated in an oven at 100° C. for 1 h. After cooling down to room temperature 40 mg (0.06 mmol) of $H_4TBAPy$ was added to this solution and the mixture was sonicated for 20 min. The yellow suspension was heated in an oven at 120° C. for 24 h. After cooling down to room temperature, yellow polycrystalline material was isolated by filtration and washed with DMF and subsequently activated with HCl.

1.5 μm NU-1000:

1 mL of solution A and 2 mL of solution B were added to a 1.5-dram vial containing 20 μL TFA (0.26 mmol), resulting in a translucent yellow solution. 10 sample vials were prepared under the same conditions at once and placed into an oil bath at 120° C. for 1 h, during which time a yellow suspension formed. After cooling down to room temperature, the 10 vials were combined and the suspension was isolated by centrifugation at 7800 rpm for 10 min. The samples was further washed with DMF and acetone twice, then subsequently activated with HCl.

800 nm NU-1000:

1 mL of solution A and 2 mL of solution B were added to a 1.5-dram vial containing 20 μL TFA (0.26 mmol), resulting in a translucent yellow solution. 10 sample vials were prepared under the same conditions at once and placed into an oil bath at 120° C. for 30 min, during which time a yellow suspension formed. After cooling down to room temperature, the 10 vials were combined and the suspension was isolated by centrifugation at 7800 rpm for 10 min. The samples was further washed with DMF and acetone twice, then subsequently activated with HCl.

600 nm CYCU-3:

a reaction mixture of $H_2SDC$ (0.1073 g, 0.40 mmol), $AlCl_3 \cdot 9H_2O$ (0.107 g, 0.4 mmol), TFA (0.114 ml, 2.0 mmol), and DMF (10.0 ml) was heated at 140° C. for 1 day. A pale-yellow powder was filtered off, washed with DMF twice and with acetone twice, and then activated at 100° C. under vacuum for 24 h.

4 μm CYCU-3:

a reaction mixture of $H_2SDC$ (0.322 g, 1.2 mmol), $AlCl_3 \cdot 9H_2O$ (0.321 g, 1.2 mmol), TFA (0.114 ml, 2.0 mmol), and DMF (6.0 ml) was heated at 140° C. for 1 day. A pale-yellow powder was filtered off, washed with DMF twice and with acetone twice, and then activated at 100° C. under vacuum for 24 h.

600 nm PCN-600:

$[Fe_3O(OOCCH_3)_6OH] \cdot 2H_2O$ (10 mg), FeTCPP (10 mg) and TFA (30 μL) in 2 mL of DMF were ultrasonically dissolved in a 20 mL Pyrex vial. The mixture was heated in 150° C. oven for 12 h. After cooling down to room temperature, dark needle shaped crystals were obtained and washed with DMF twice and with acetone twice, and then activated at 100° C. under vacuum for 24 h.

10 μm PCN-600:

$[Fe_3O(OOCCH_3)_6OH] \cdot 2H_2O$ (10 mg), FeTCPP (10 mg) and TFA (120 μL) in 2 mL of DMF were ultrasonically dissolved in a 20 mL Pyrex vial. The mixture was heated in 150° C. oven for 12 h. After cooling down to room temperature, dark needle shaped crystals were washed with DMF twice and with acetone twice, and then activated at 100° C. under vacuum for 24 h.

Preparation of Resorufin Phosphonate (RP).

To a solution of diethyl butylphosphonate (250 mg, 1.3 mmol) in dry $CH_2Cl_2$ (7 mL) was added oxalyl chloride (656 mg, 443 μL, 5.2 mmol) dropwise over 1 min. This resulted in evolution of gas. This mixture was stirred 5 hr and then concentrated on a rotary evaporator to yield the phosphoryl chloride as a golden liquid. The crude phosphoryl chloride was then diluted to 2 mL with $CH_2Cl_2$, and added to a solution of resorufin sodium salt (303 mg, 1.3 mmol) in pyridine (4 mL) at 0° C. This mixture was allowed to warm up to room temperature and stirred for 24 h. The reaction mixture was then diluted with 20 mL $CH_2Cl_2$ and poured into IN HCl (200 mL). The organic layer was separated off and the water extracted with additional $CH_2Cl_2$ (2×20 mL). The organic fraction was then washed with water (100 mL), brine (100 mL) and then dried over $Mg_2SO_4$. After filtration, the solution was concentrated to yield a red oil. The crude product was purified on silica gel using a gradient of 5%-10% acetone in $CH_2Cl_2$ to yield the resorufin phosphonate as an orange-red solid (57 mg, 12%). 1H NMR (500 MHz, $CDCl_3$) δ 7.74 (d, J=8.5 Hz, 1H), 7.42 (t, J=13.0 Hz, 1H), 7.22 (d, J=1.8 Hz, 2H), 6.84 (dd, J=9.8, 1.9 Hz, 1H), 6.31 (d, J=1.9 Hz, 1H), 4.29-4.11 (m, 2H), 1.93 (dt, J=16.3, 7.2 Hz, 2H), 1.70-1.64 (m, 2H), 1.43 (dd, J=14.9, 7.4 Hz, 2H), 1.32 (t, J=7.1 Hz, 3H), 0.95-0.90 (m, 3H). 13C NMR (126 MHz, CDCl3) δ 186.31 (s), 153.92 (d, J=8.4 Hz), 144.72 (s), 135.04 (s), 134.80 (s), 131.56 (s), 130.57 (s), 118.20 (d, J=4.7 Hz), 108.16 (d, J=4.8 Hz), 107.23 (s), 62.86 (d, J=7.0 Hz), 29.71 (s), 26.32 (s), 25.20 (s), 24.27 (d, J=5.5 Hz), 23.59 (d, J=17.7 Hz), 16.42 (d, J=6.0 Hz), 13.53 (s). 31P NMR (400 MHz, $CDCl_3$) δ 31.22 (s). MS (ESI+) m/z: 362.04 [M+H]+, 384.02 [M+Na]+.

Example 2: Immobilization of Organophosphorus Acid Anhydrolase by PCN-128y

This Example illustrates the use of the MOF PCN-128y to immobilize OPAA. OPAA is of interest as a catalytic enzyme for nerve agent detoxification.

Figure 9B:
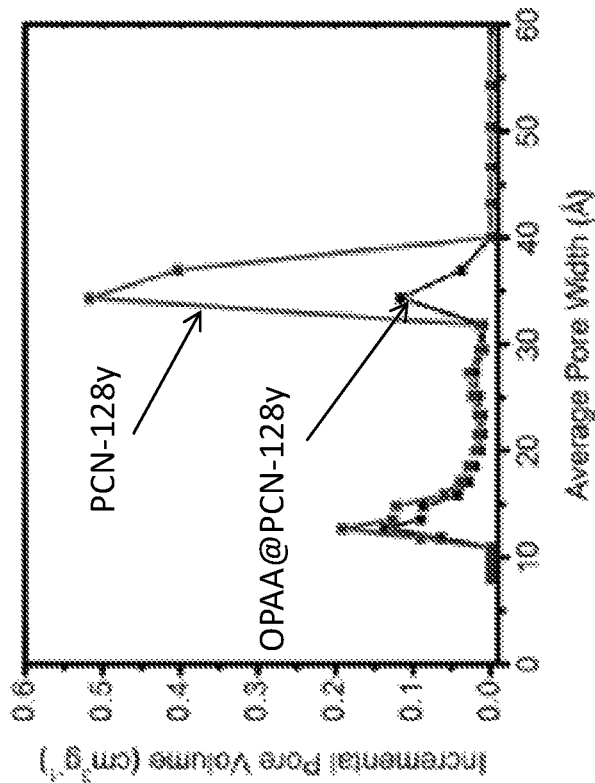
FIG. 9B depicts DFT pore size distributions for PCN-128y (gray) and OPAA@PCN-128y (black).
Figure 9A:
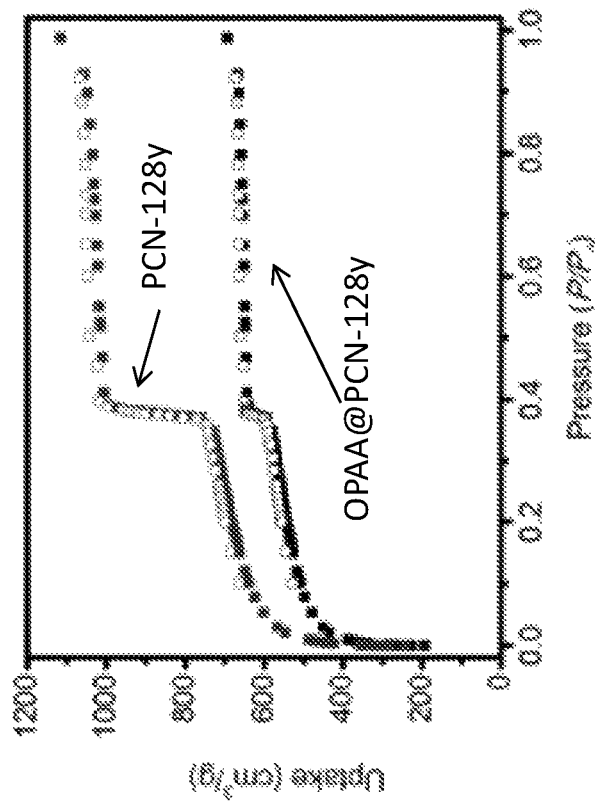
FIG. 9A shows $N_2$ adsorption-desorption isotherms
Figure 9D:
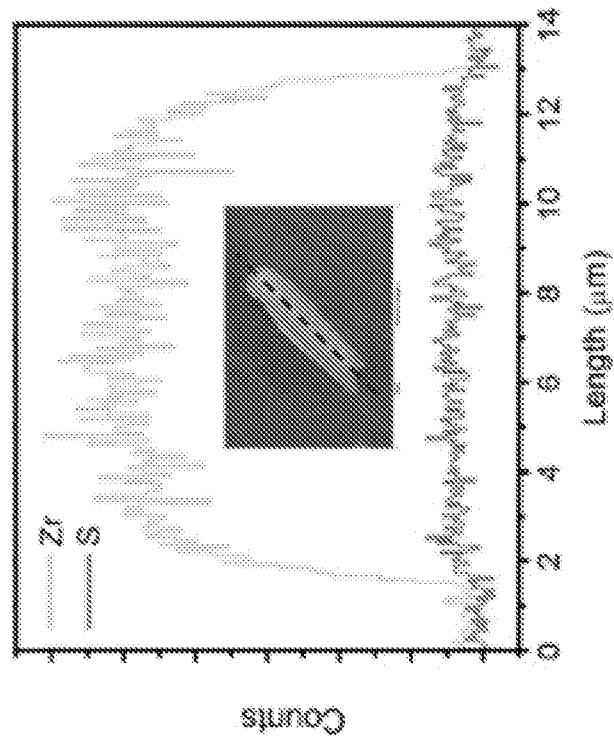
FIG. 9D shows an SEM image and EDX spectra of a single crystal of OPAA@ CN-128y. EDX scan lines for Zr and S are respectively in light gray and dark gray. The dashed line indicates where the EDX scan was taken.
Figure 9C:
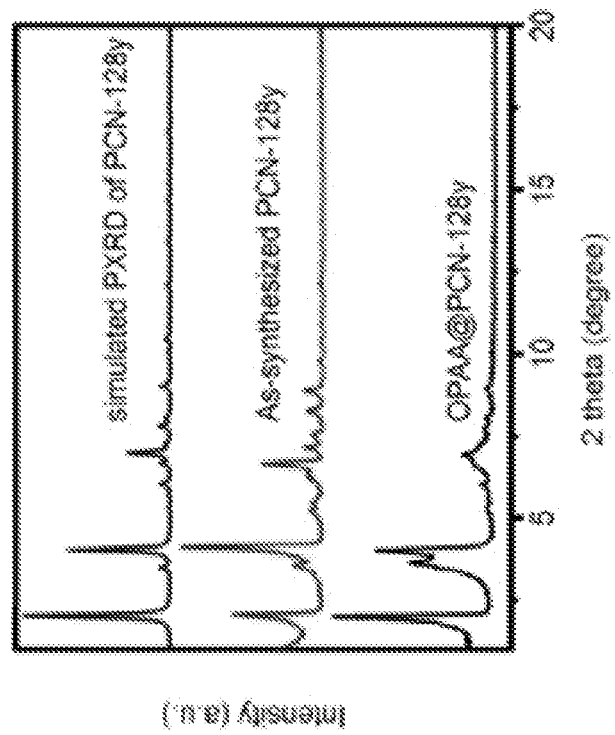
FIG. 9C shows PXRD patterns of simulated PCN-128y, experimental PCN-128y, and OPAA@PCN-128y.

The large mesoporous channels of the zirconium MOF PCN-128y (4.4 nm) are ideal for confining, but not constricting, the wild type OPAA (from bacterium *Alteromonas* sp. JD6.5, 440 amino acid), a protein featuring a small-axis length of ~4.4 nm, in highly concentrated, yet non-aggregated, form (FIG. 8A). In contrast, the narrower triangular channels (micropores) of PCN-128y should effectively exclude OPAA, leaving them free instead to transport molecule-sized reactants and products. Windows between small and large channels, present in high density, should permit reactants to readily access the immobilized OPAA (FIG. 8B). These features combined with the high chemical and thermal stability of PCN-128y, make this MOF a useful material for the preparation of an immobilized nerve agent antidote.

This example reports the successful encapsulation and characterization of OPAA in PCN-128y, and its catalytic performance in detoxifying the nerve agent simulant diisopropyl fluorophosphate (DFP) and the real nerve agent O-Pinacolyl methyl fluorophosphonate (Soman) (FIG. 8C). More importantly, the immobilized OPAA shows higher thermal stability than the free enzyme and shows superior long-term storage stability.

To immobilize OPAA, activated crystals of PCN-128y were treated with a bis-tris-propane buffer (BTP) solution of OPAA (0.2 mg/mL, pH 7.2) at 25° C. The uptake of OPAA by PCN-128y was followed using UV-vis spectroscopy and a maximum loading of 0.10-0.12 mg/mg was reached after 24 h. The solid sample (hereafter denoted as OPAA@PCN-128y) was then washed with BTP buffer solution five times to remove the OPAA adsorbed on the surface. To confirm the loading of OPAA in PCN-128y, inductively coupled plasma-optical emission spectroscopy (ICP-OES) was used to measure the ratio of Zr (Zr nodes in MOF) to S (methionines and cysteines in OPAA) in the digested OPAA@PCN-128y samples. The ICP analysis confirmed an OPAA uptake of 0.12 mg/mg. It was believed that the OPAA loading capacity of PCN-128y was much higher than that of any other porous material yet examined. The $N_2$ adsorption isotherm of OPAA@PCN-b128y exhibited a lower $N_2$ uptake capacity than that of PCN-128y (FIG. 9A). The density functional theory (DFT) pore size distribution analysis of PCN-128y and OPAA@PCN-128y showed that the pore volume corresponding to the triangular channels (1.2-1.5 nm) of PCN-128y dropped from 0.19 $cm^3/g$ to 0.14 $cm^3/g$, while the incremental pore volume corresponding to the hexagonal channels (3.3-4.0 nm) dropped from 0.52 $cm^3/g$ to 0.13 $cm^3/g$ after OPAA encapsulation (FIG. 9B). These results are in agreement with the contention that a considerable portion of the mesopores in PCN-128y are occupied by OPAA while the micropores in PCN-128y are still mostly empty. The powder X-ray diffraction (PXRD) patterns and scanning electron microscopy (SEM) images of PCN-128y before and after OPAA immobilization confirmed that bulk crystallinity and morphology of PCN-128y were retained (FIG. 9C). To determine the distribution of OPAA in PCN-128y crystals, in-situ confocal laser scanning microscopy (CLSM) was used to image AlexaFluor-647-tagged OPAA in crystals of PCN-128y at different depths. Comparison of CLSM micrographs from the bottom to the top of a 5 μm z-axis height indicated that OPAA was not only on the surface of PCN-128y but was dispersed throughout the PCN-128y crystals. In addition, SEM-EDX images showed an even distribution of sulfur along a single crystal of PCN-128y, which further confirms that OPAA was dispersed throughout the MOF (FIG. 9D).

Figures 10A, 10B:
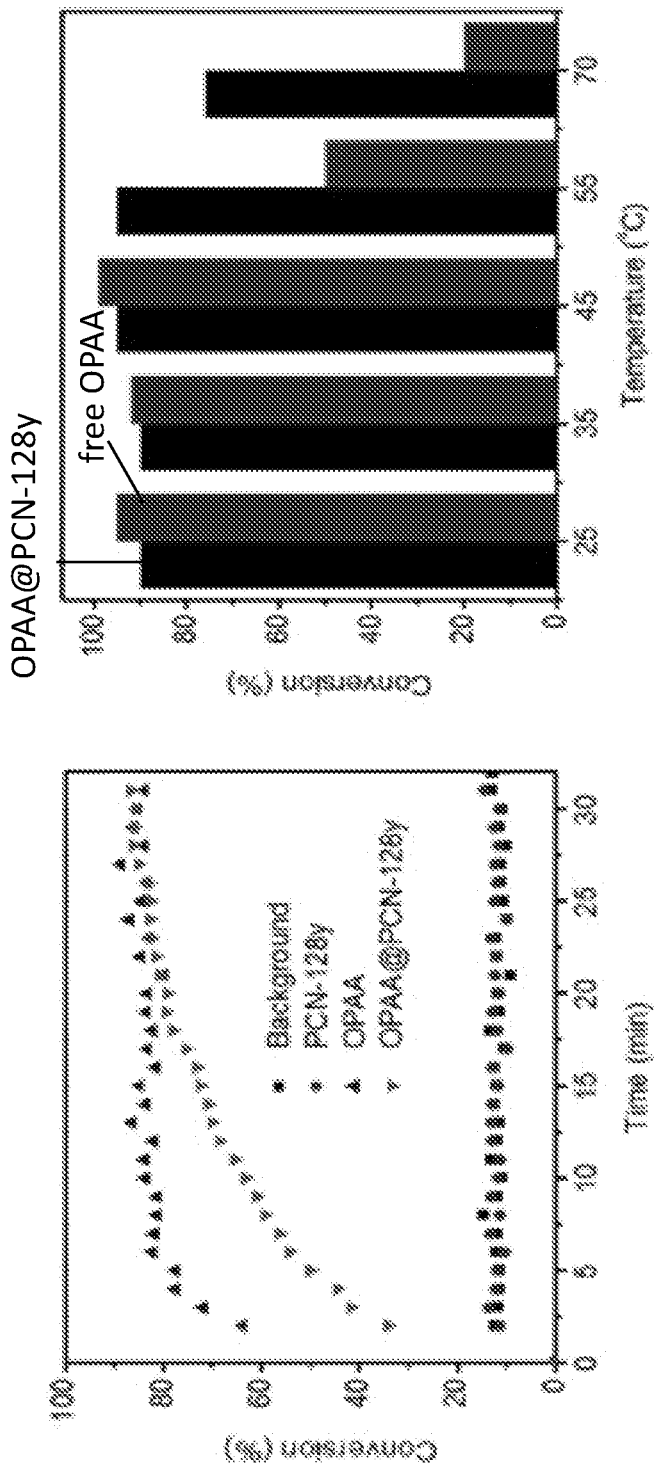
FIG. 10A shows a reaction profile of DFP hydrolysis by free OPAA, OPAA@PCN-128y, PCN-128y, and the background reaction.
FIG. 10B depicts thermal stability as measured in terms of conversion of DFP hydrolysis upon incubating at increasing temperatures (black bar for OPAA@PCN-128y and gray bar for free OPAA).
Figure 10D:
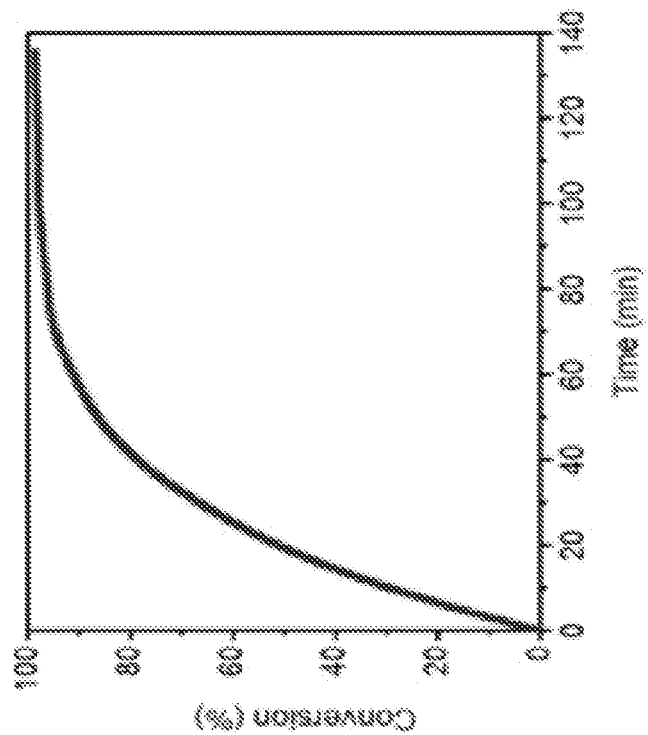
FIG. 10D shows a reaction profile of Soman hydrolysis by OPAA@PCN-128y.
Figure 10C:
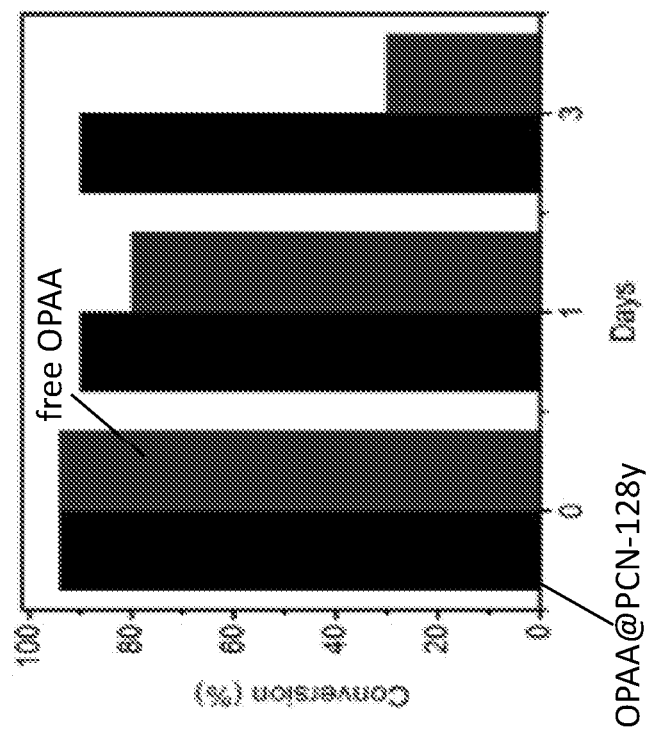
FIG. 10C shows long-term stability as measured in terms of conversion of DFP hydrolysis after room temperature storage in dry-powder form over time (black bar for OPAA@PCN-128y and gray bar for free OPAA).
Figure 10E:
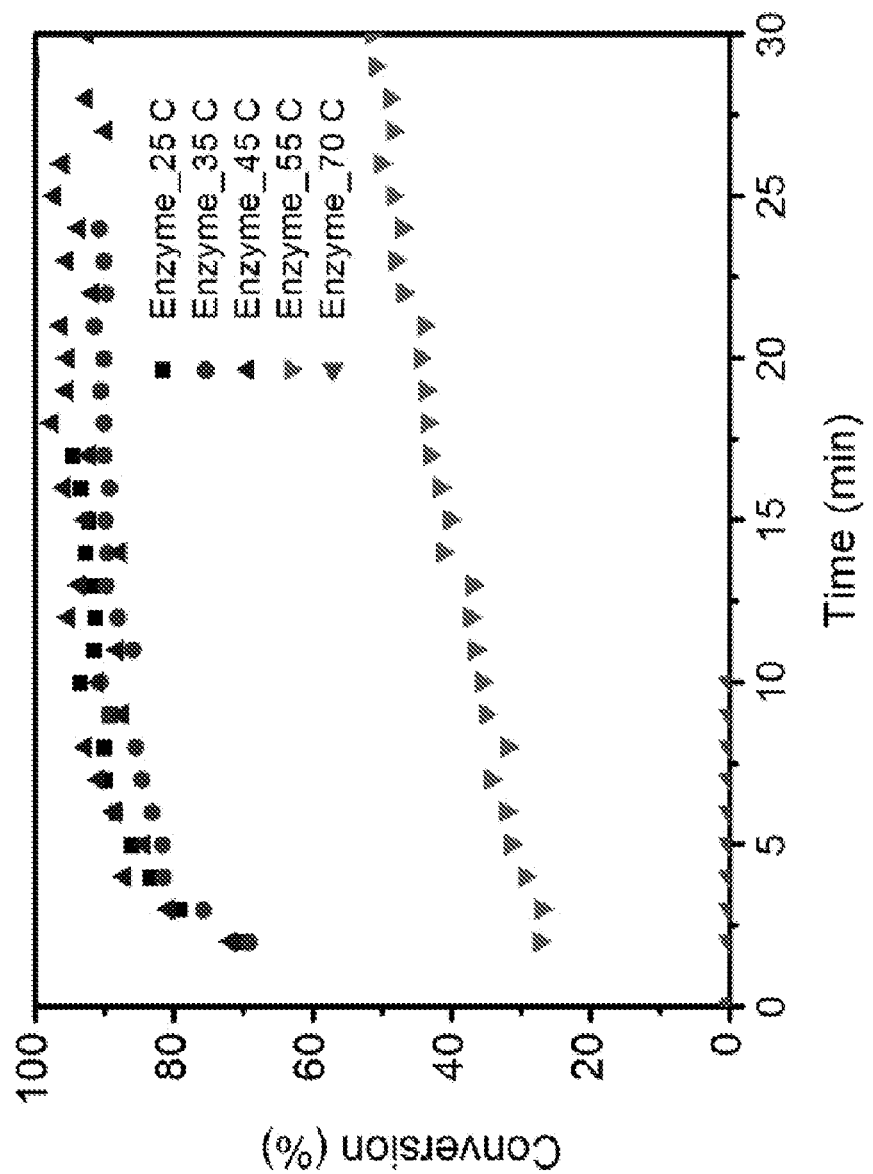
FIGS. 10E and 10F show hydrolysis of DFP over time by free OPAA (top) and OPAA@PCN-128 (bottom) incubated in BTP buffer (pH 7.2) at different temperatures.
Figure 10F:
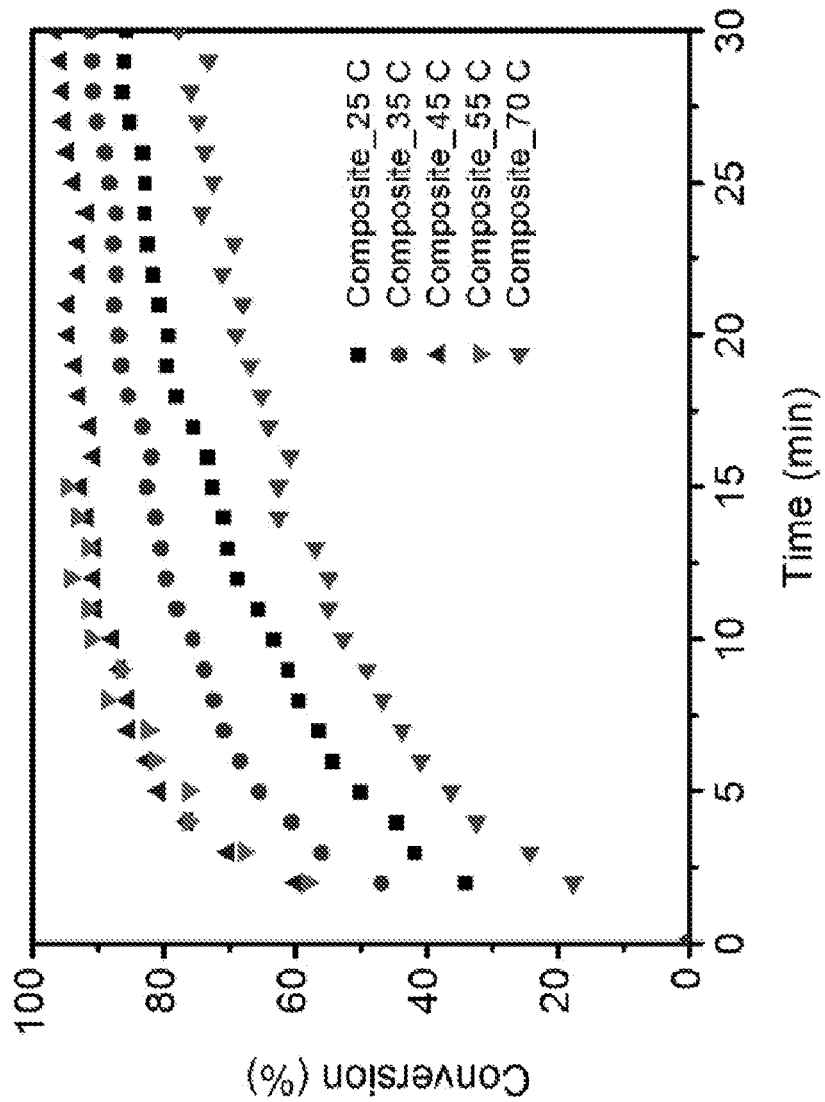
Figure 11:
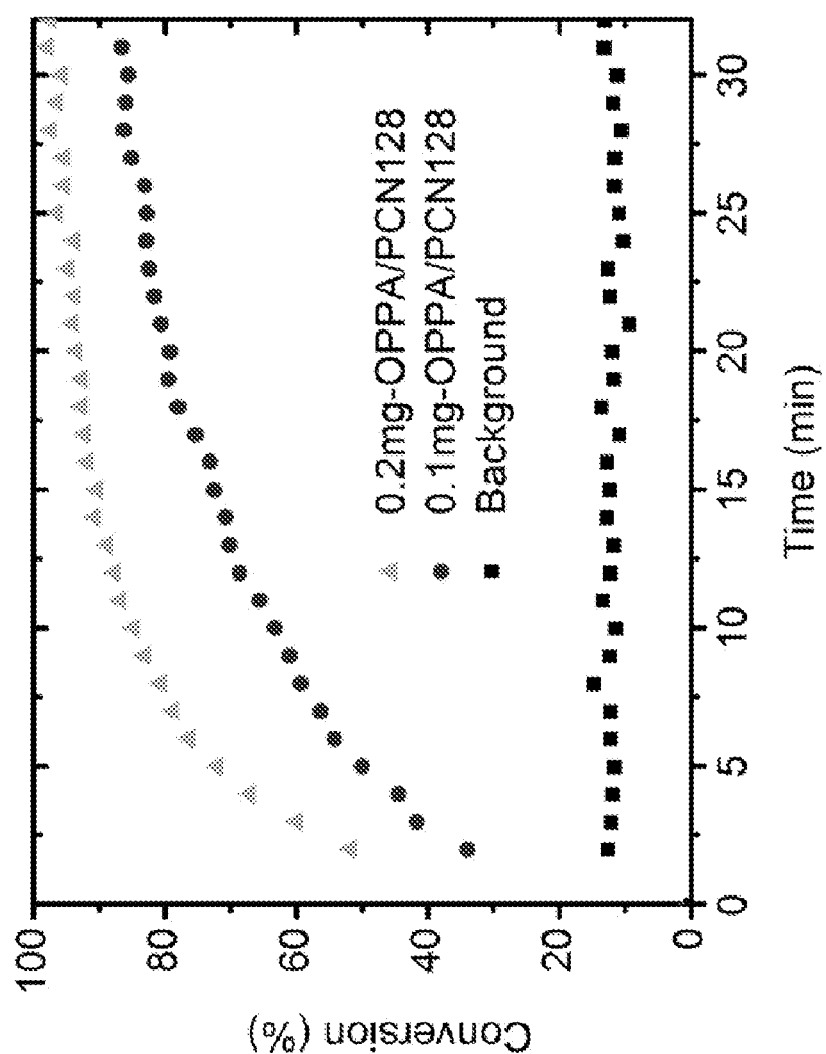
FIG. 11 shows hydrolysis of DFP over time by free OPAA (top) and OPAA@PCN-128 (bottom) incubated in BTP buffer (pH 7.2) at different temperatures.

The enzyme activity and encapsulation efficacy of OPAA@PCN-128y were next examined by utilizing a less toxic nerve agent simulant diisopropyl fluorophosphate (DFP) as a model substrate. Previous studies have demonstrated that zirconium MOFs themselves are excellent nerve agent detoxification catalysts, but only in buffered solutions at pH values of ca. 8.5 and higher. Enzyme-free PCN-128y in pH 7.2 BTP buffer, however, showed no catalytic activity the hydrolysis of DFP is evident (FIG. 10A). Compared to free OPAA under the same conditions, the initial rate of DFP hydolysis rate of OPAA@PCN-128y was comparatively low possibly due to slow intra-MOF diffusion by reactants and products (FIG. 10A). Nevertheless, for both free OPAA and OPAA@PCN-128y as catalysts, the conversion of DFP plateaued at 80-90%. To examine the enzyme accessibility after immobilization, composites with different enzyme loadings were prepared and tested for DFP hydrolysis (FIG. 11). The results indicated that the activity of composites systematically increased as the enzyme loadings increased. To assess enzyme thermal stability, the extent of hydrolytic degradation of DFP achieved over a range of incubation/reaction temperatures using free versus encapsulated OPAA as the catalyst was measured (FIGS. 10B, 10E and 10F). Both free OPAA and OPAA@PCN-128y showed optimal activity after incubation at 45° C. However, the incubation of free OPAA at 55° C. resulted in a significant loss of the conversion of DFP, indicating the loss of enzymatic activity. In contrast, OPAA@PCN-128y yielded around 90% conversion. When the incubation temperature was further increased to 70° C., the OPAA@PCN-128y showed remarkable stability and a conversion of almost 75%. In contrast, the low conversion for free OPAA at 70° C. suggests that free OPAA was denatured at this temperature.

Figure 12A:
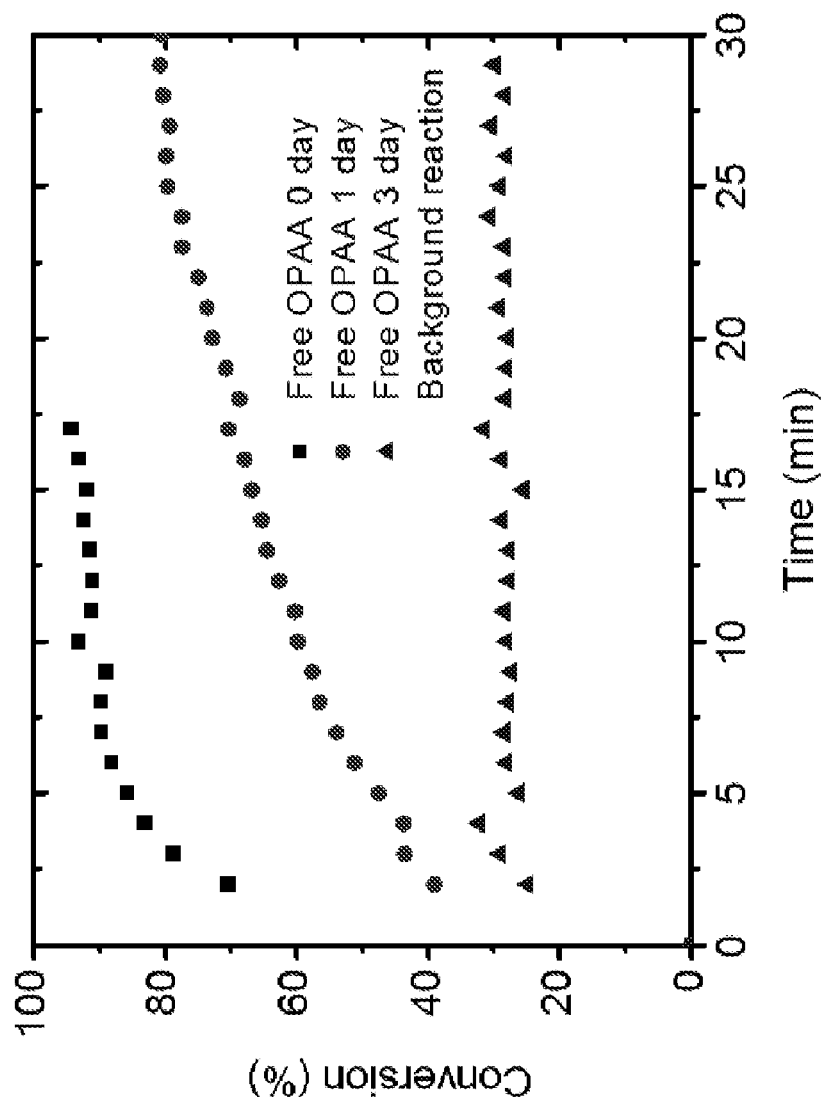
FIG. 12A shows hydrolysis of DFP over time by dried free OPAA.
Figure 12B:
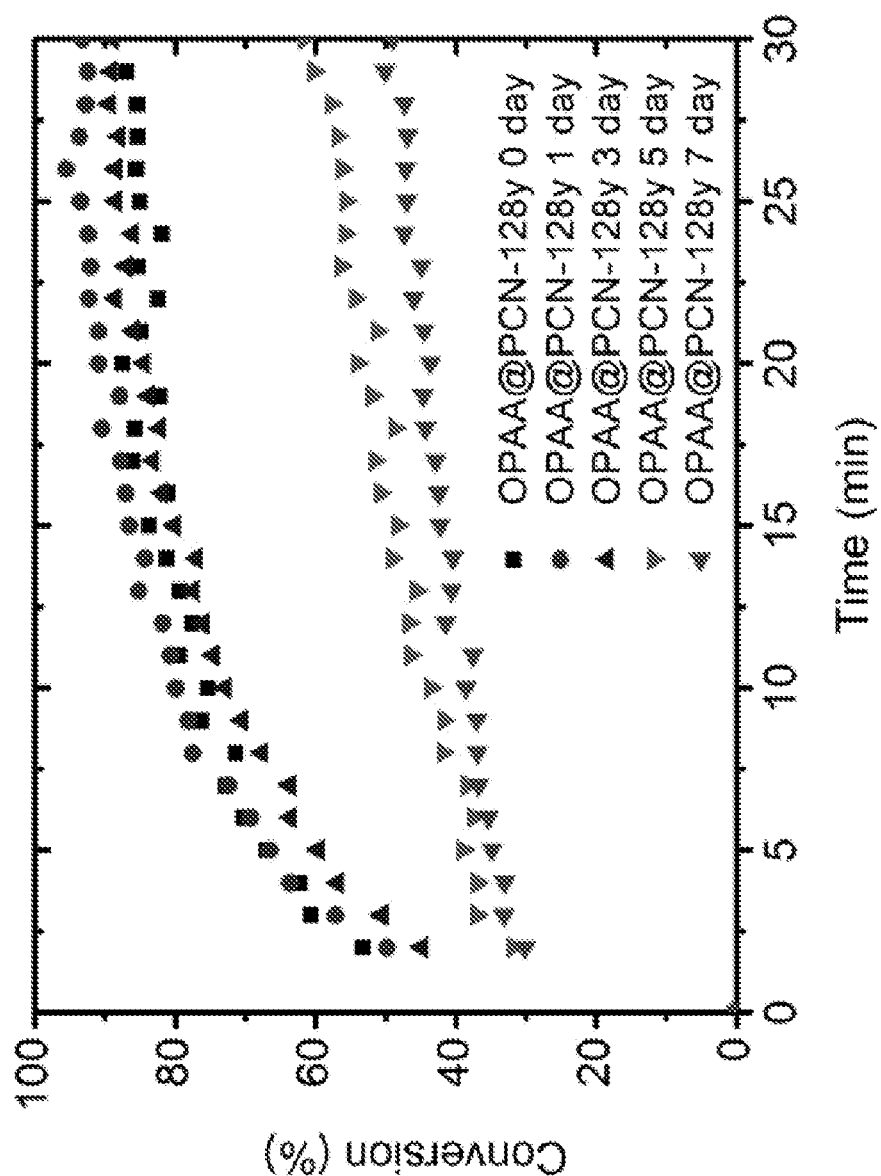
FIG. 12B depicts hydrolysis of DFP over time by OPAA@PCN-128y stored at room temperature for different time (days).
Figure 13:
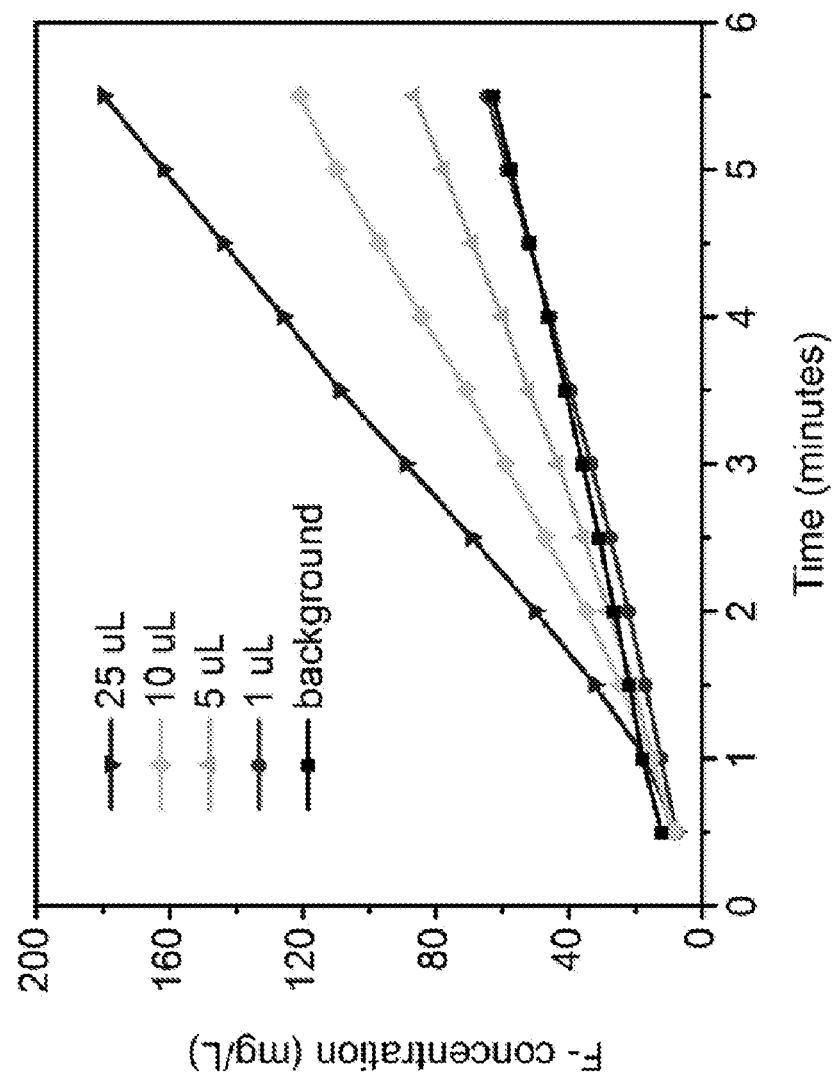
FIG. 13 depicts hydrolysis of soman by OPAA@PCN-128y with different catalyst dose and background reaction.
Figure 14A:
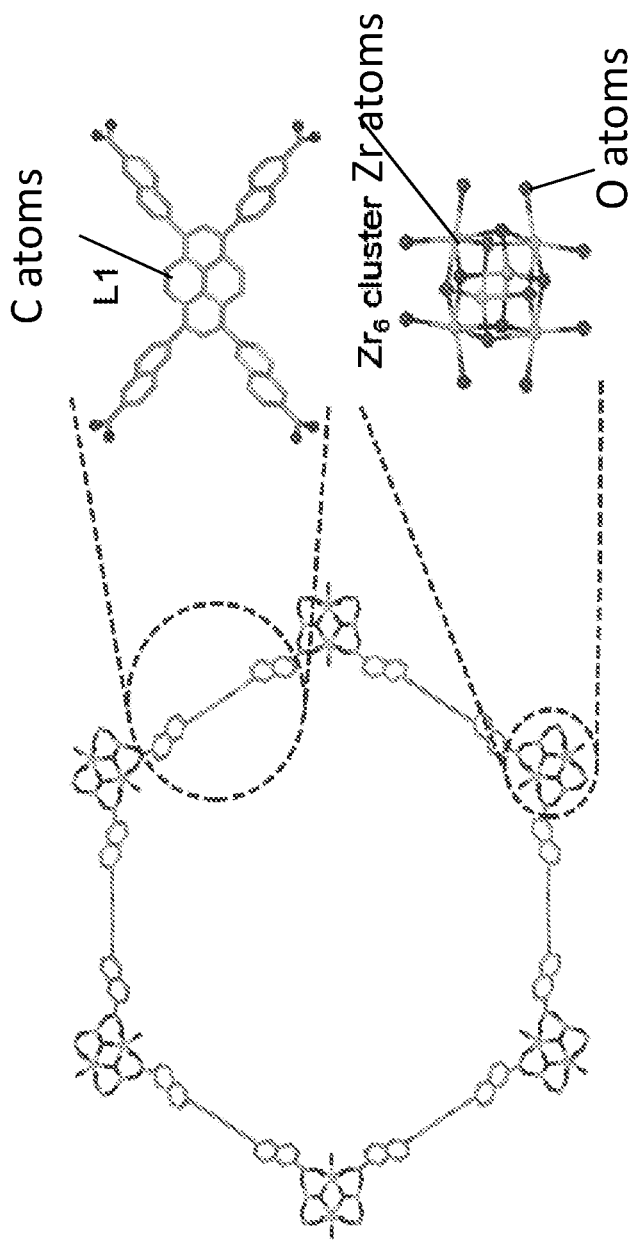
FIG. 14A depicts a simulated crystal structure of NU-1003 composed of tetratopic pyrene-based linker L1 and $Zr_6$ cluster.
Figure 14B:
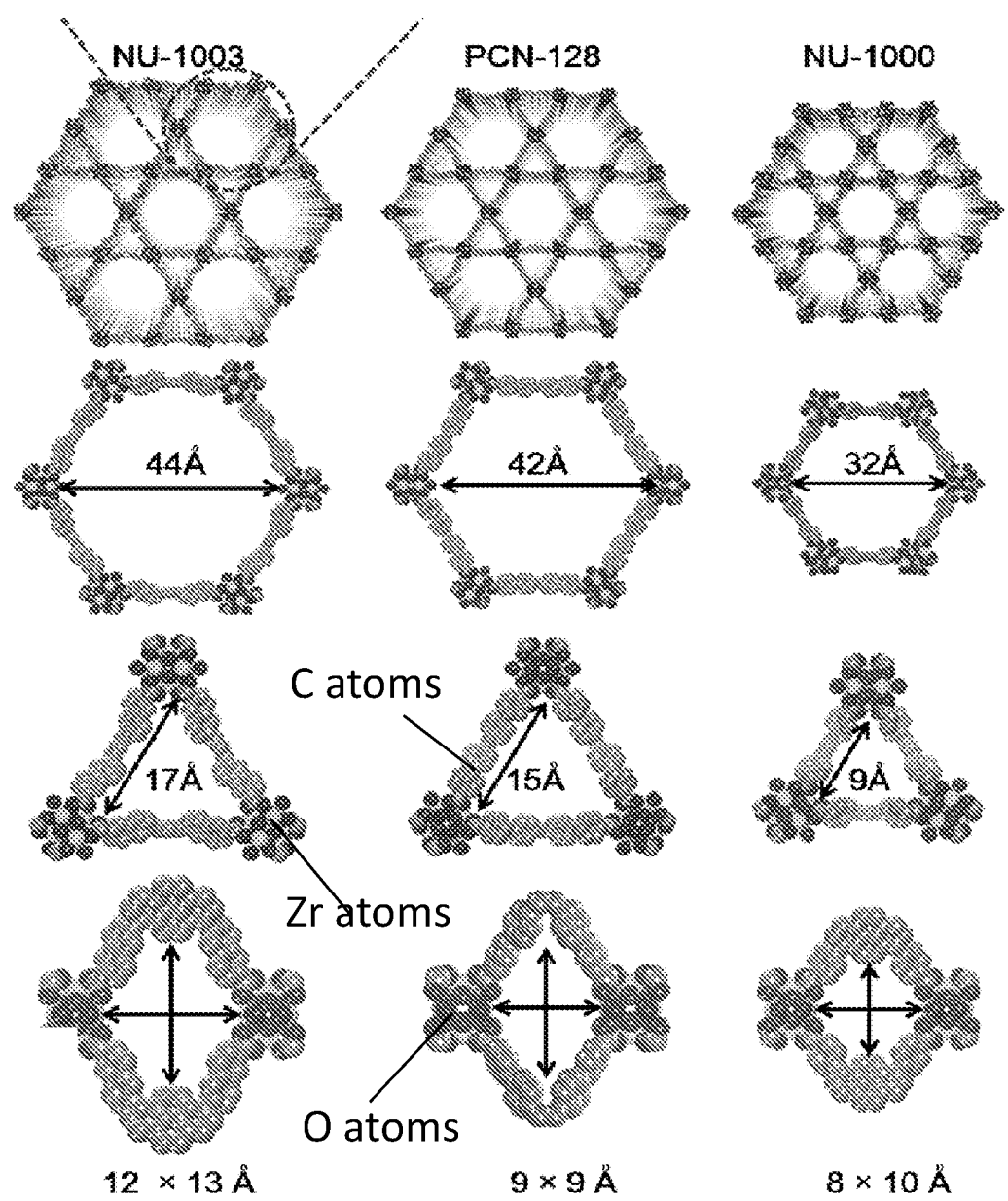
FIG. 14B depicts the packing diagram, hexagonal pores, triangular pores, and windows between hexagonal/triangular pores in NU-1003 (left), PCN-128 (middle), and NU-1000 (right). The pore lengths and diameters are measured between the two closest atoms in the direction of the arrows taking account the van der Waals radii of atoms.
Figure 15A:
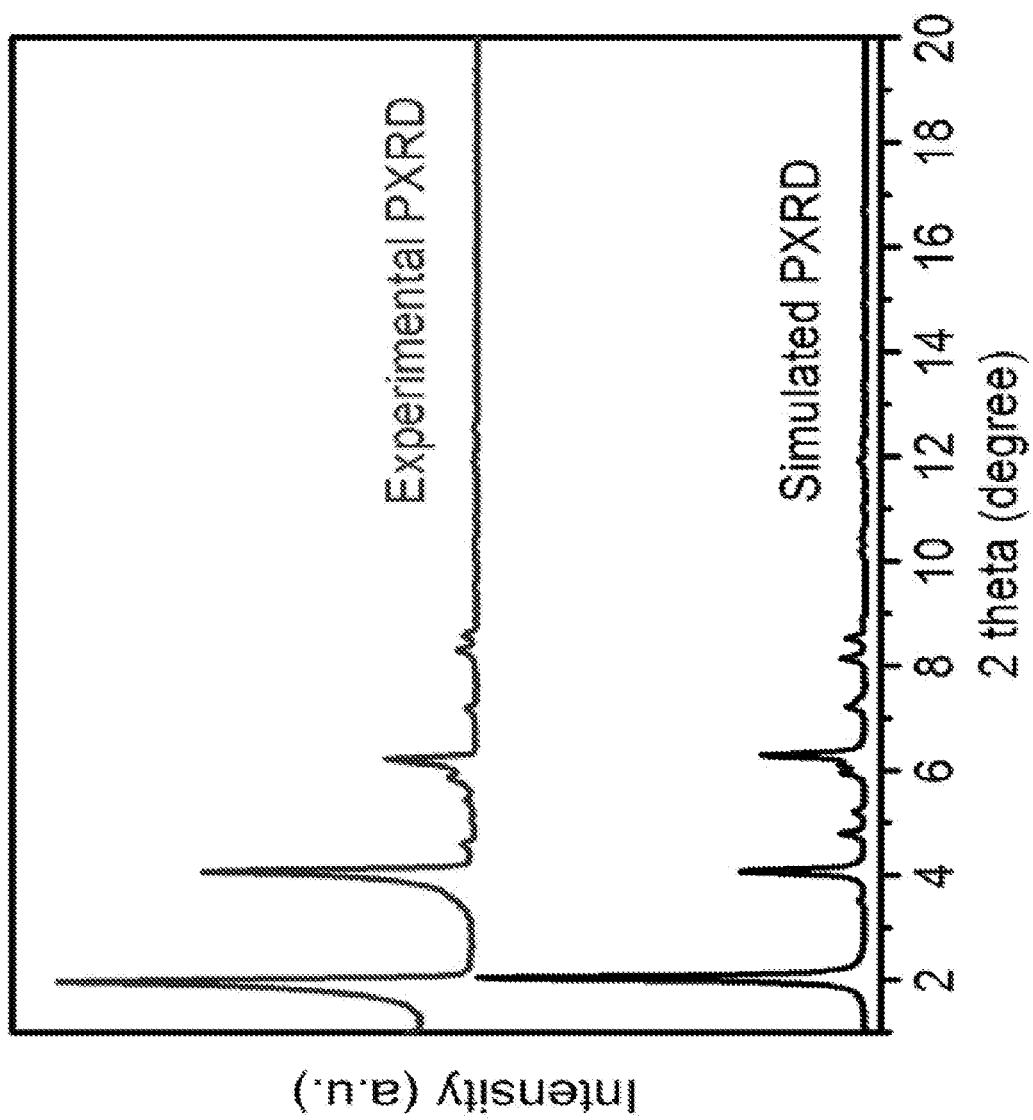
FIG. 15A shows experimental and simulated PXRD patterns of NU-1003 at 77K.
Figure 15B:
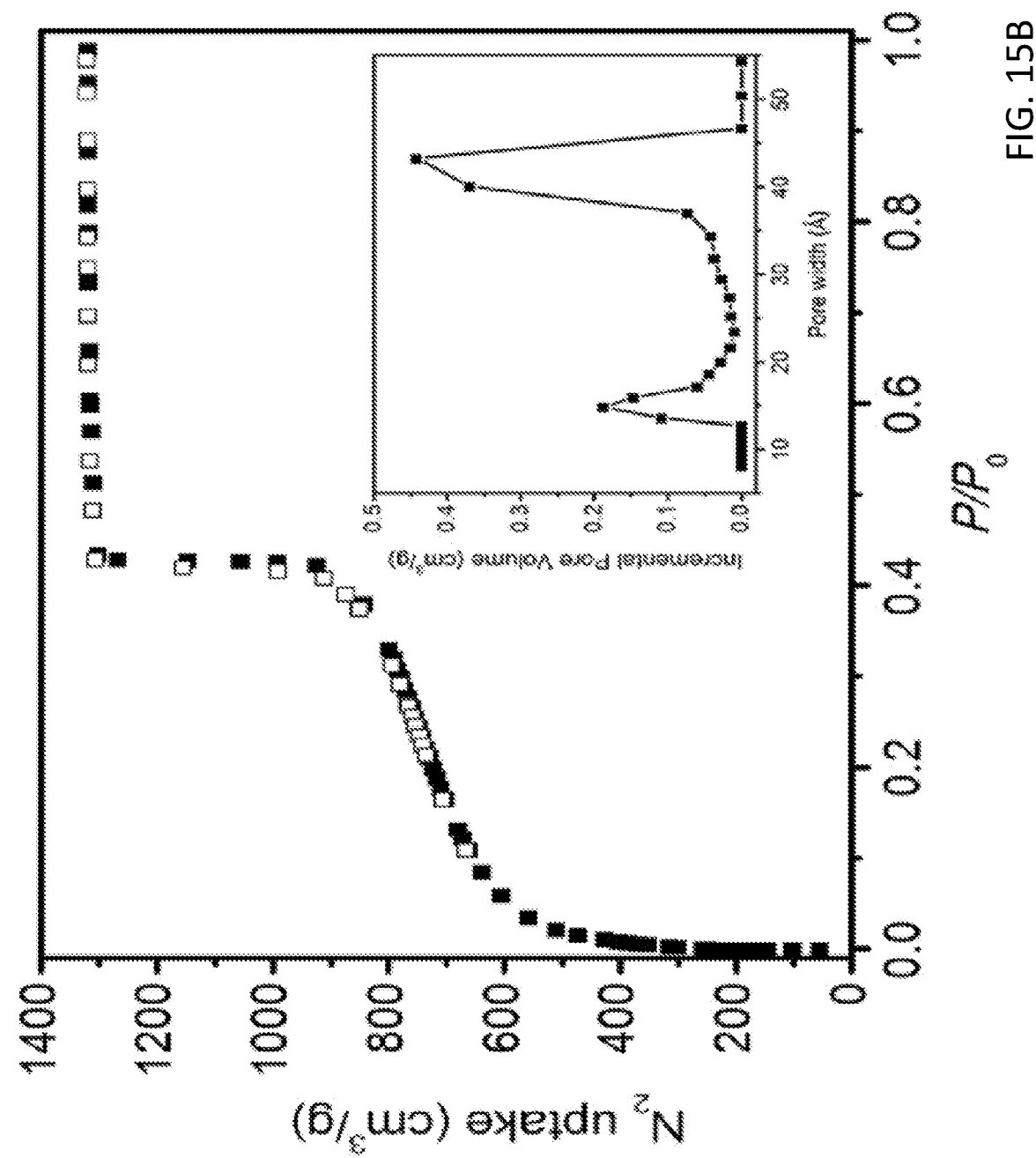
FIG. 15B depicts an $N_2$ isotherm of NU-1003 at 77K (inset: DFT pore size distribution) after activation by SCD.
Figure 16F:
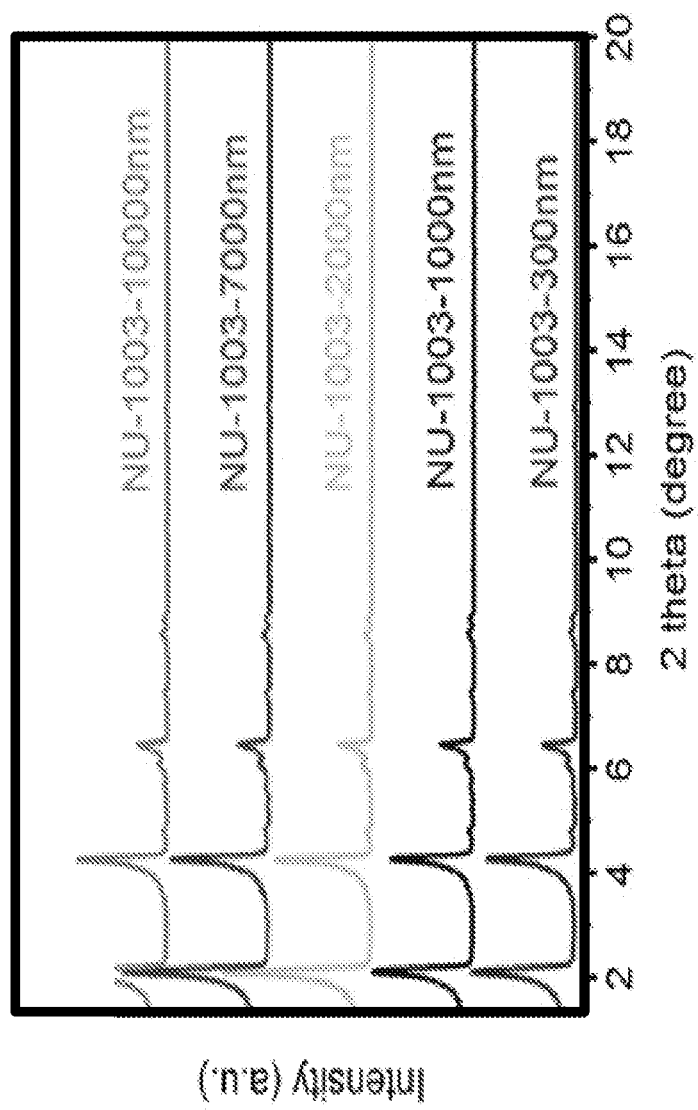
FIG. 16F shows PXRD patterns of different sizes of NU-1003 crystals.
Figure 17C:
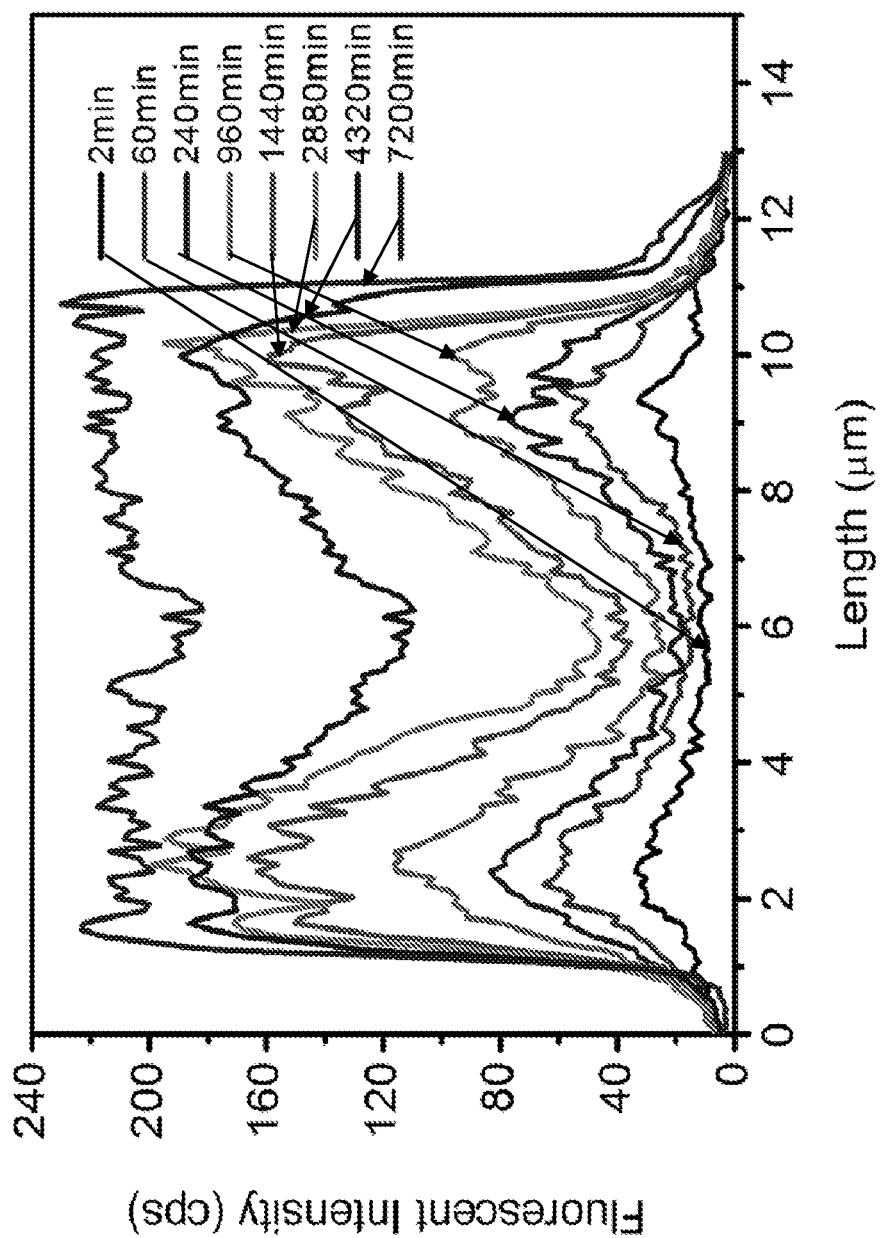
FIG. 17C shows plots of fluorescence intensity along a single crystal of OPAA@NU-1003-10000 nm with time.
Figures 18A, 18B:
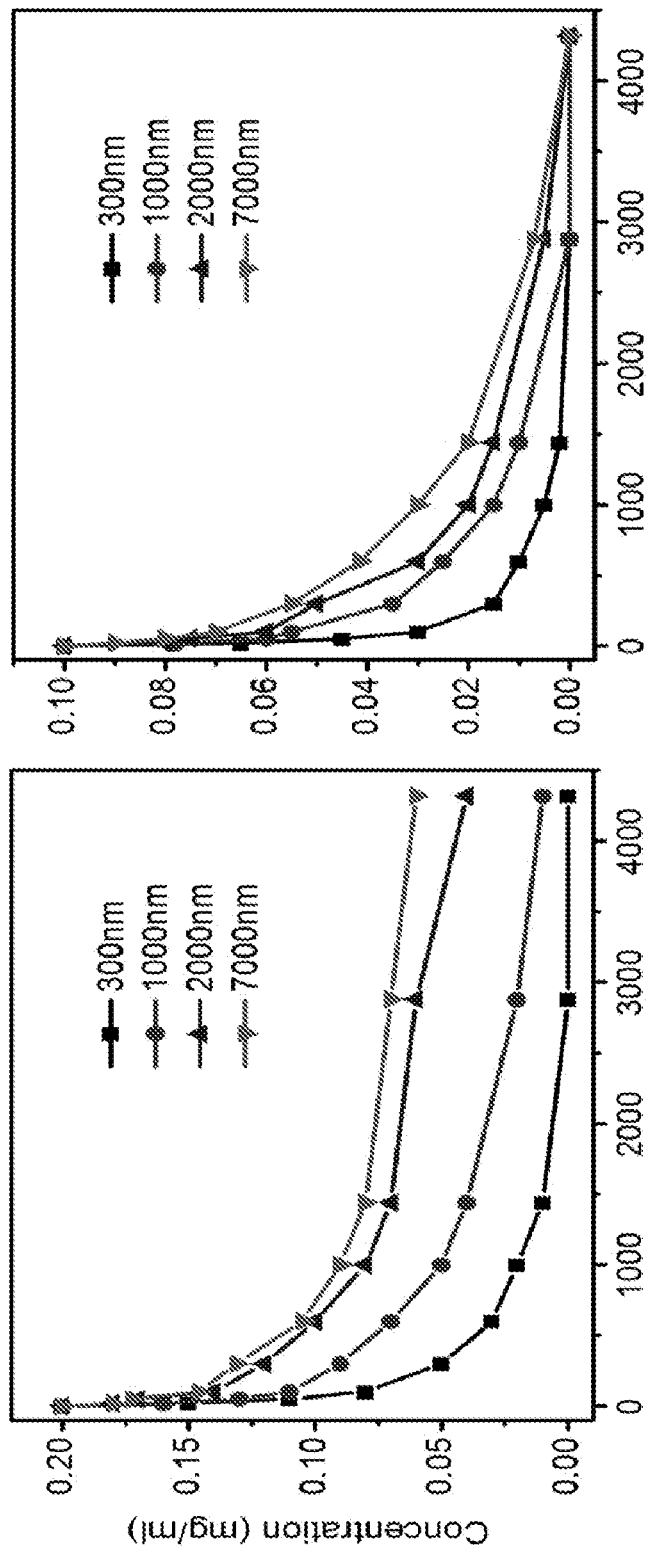
FIG. 18A depicts OPAA concentration in a supernatant after soaking different sizes of NU-1003 in a buffer solution of 0.2 mg/ml OPAA.
FIG. 18B shows OPAA concentration in the supernatant after soaking different sizes of NU-1003 in a buffer solution of 0.1 mg/ml OPAA.
Figure 18C:
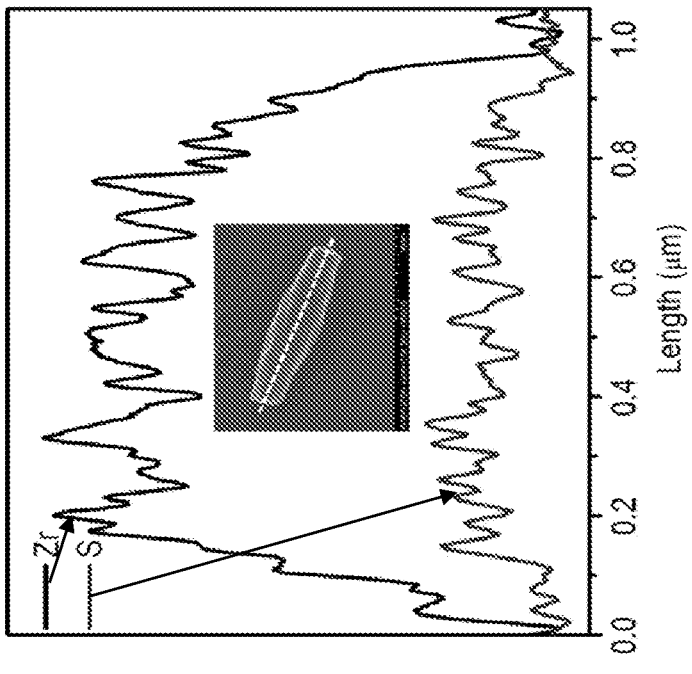
FIG. 18C shows an SEM image and EDX spectra of a single crystal of OPAA@NU-1003-300 nm.
Figure 18D:
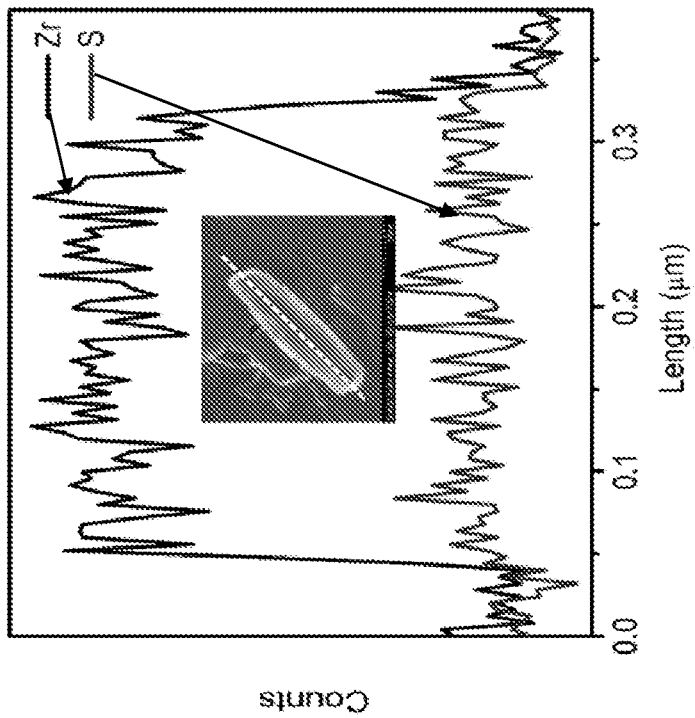
FIG. 18D shows an SEM image and EDX spectra of a single crystal of OPAA@NU-1003-1000 nm.
Figures 18E, 18F:
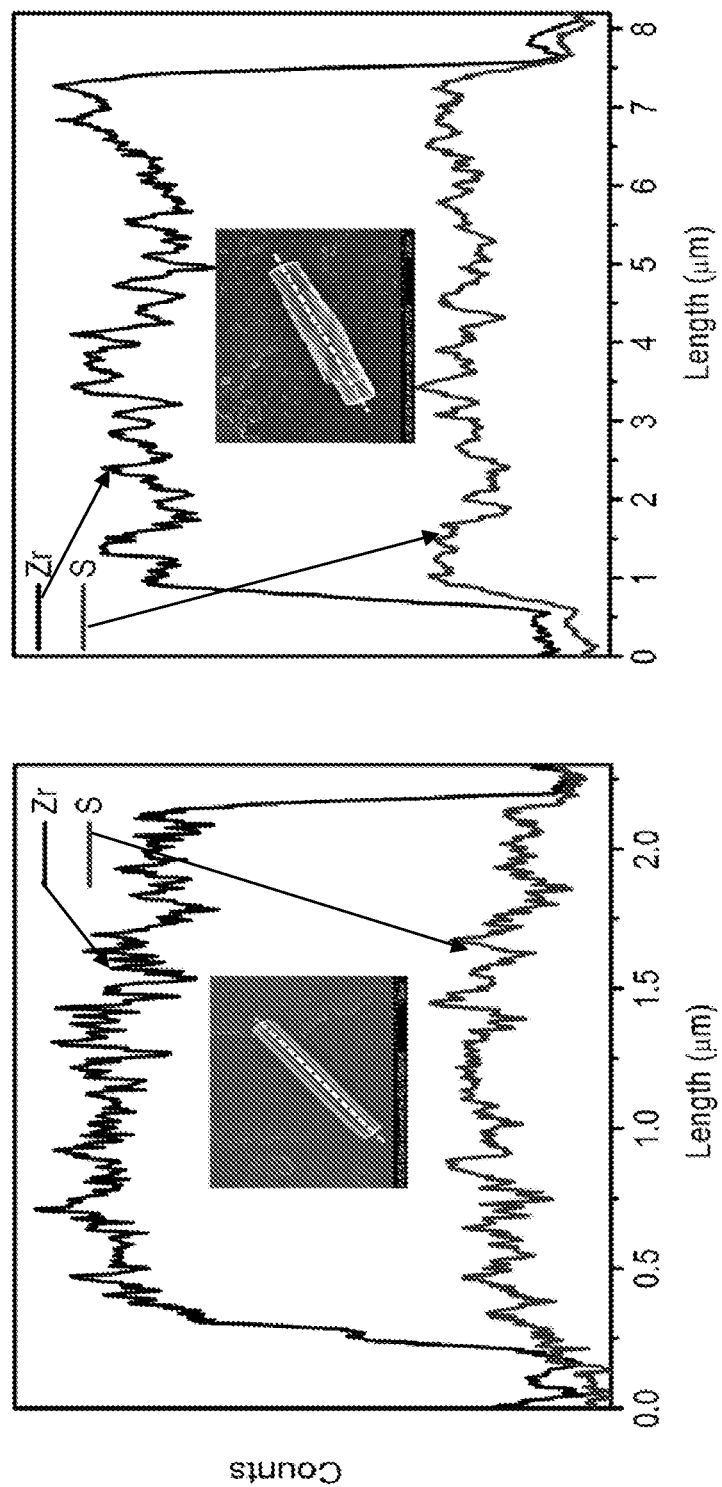
FIG. 18E shows an SEM image and EDX spectra of a single crystal of OPAA@NU-1003-2000 nm.
FIG. 18F show an SEM image and EDX spectra of a single crystal of OPAA@NU-1003-7000 nm. The dashed white lines indicate where the EDX scan was taken.

Encouraged by the high thermal stability of OPAA encapsulated in PCN-128y, the issue of long-term stability was next addressed, and is important one for field applications issue of OPAA or other detoxification enzymes. To assess temporal stability, the as-synthesized OPAA@PCN-128y was air dried and free OPAA was lyophilized. Both dried samples were then stored at room temperature, with smaller samples being removed and tested after storage for various lengths of time. (FIG. 10C and FIGS. 12A and 12B). Stability was measured by determining the conversion of DFP using the same conditions used previously. Initially, when reintroduced to DFP solutions, both the dried OPAA@PCN-128y and lyophilized OPAA achieved nearly 90% conversion. For lyophilized OPAA subjected to one day of dry storage, conversion plateaued at 79%, implying some loss of stability. After three days of drying, lyophilized free OPAA proved capable of catalyzing hydrolysis of 30% of the DFP present. In striking contrast, even after three days of dry storage, OPAA@PCN-128y remained capable of catalyzing the hydrolysis of 90% of the DFP present. These results show that the MOF can be used to protect and stabilize OPAA which is important for a portable antidote material to be used in extreme conditions (such as high temperatures in the desert with low humidity). To further demonstrate the efficacy of OPAA@PCN-128y as a decontaminant for G-type nerve agents, its catalytic performance for the hydrolysis of the real nerve agent, Soman, was examined. Caution: Soman is deadly. It can be safely and legally studied only by specifically trained and authorized personnel working in secure, approved facilities. The results indicated that OPAA@PCN-128y can efficiently defluorinate/deactivate Soman (thereby removing the leaving group that enables its binding to acetylcholinesterase). By using an F electrode, the initial reaction rate was calculated to be in the range of 56-75 μmol/min/mg (FIG. 13). Similar to its behavior in the hydrolysis of DFP, OPAA@PCN-128y hydrolyzed Soman and reached 90% conversion in 60 min using 3.75 μg OPAA@PCN-128y on 3 mM Soman at 25° C. (FIG. 10D).

In summary, the water-stable mesoporous channel-type zirconium MOF PCN-128y was shown to be capable of encapsulating OPAA with a high loading. This size-matching encapsulation process was performed rapidly under mild conditions and required no prior chemical modification of the protein of interest. More importantly, following OPAA uptake by the large (mesoporous) channels of PCN-128y, the smaller channels (microporoes) of the hierarchically structured host material remained open and available as conduits for reactant and product diffusion to and from the active sites of the encapsulated enzymes. In addition, that PCN-128y was shown to excel at stabilizing the enzyme at high temperature and in dry-form for up to one month, whereas the free enzyme degraded rapidly under these conditions. These findings demonstrate that MOF encapsulated OPAA (or related enzymes) is suitable for large area and personnel decontamination.

Materials and Methods

Materials

Zirconyl chloride octahydrate ($ZrOCl_2.8H_2O$), N,N-dimethylformamide (DMF), trifluoro acetic acid (TFA), diisopropyl fluorophosphate (DFP), and bis-tris-propane were purchased from Sigma-Aldrich and used as received. AlexaFluor®647 dye was purchased from Life Technologies (Thermo Fisher Scientific). The ligand 4,4',4'',4'''-(ethene-1,1,2,2-tetrayl) tetrakis (([1,1'-biphenyl]-4-carboxylic acid)) (H4ETTC) and PCN-128y were synthesized following the published procedure. (See, Bajgar, J., *Adv Clin Chem* 2004, 38 (1), 151-216.) The gene encoding the OPAA enzyme was originally cloned from *Alteromonas* sp. JD6.5, as described previously. (See, Yang, Y.-C., *Acc. Chem. Res.* 1999, 32 (2), 109-115.)

Physical Methods and Measurements Powder X-ray diffraction (PXRD) data were collected on a Rigaku model ATX-G diffractometer equipped with a Cu rotating anode X-ray source. $N_2$ sorption isotherm measurements were performed on a Micromeritics Tristar II 3020 (Micromeritics, Norcross, Ga.) at 77 K. Between 30 and 50 mg of material was used for each measurement. $^{31}P$ NMR spectrum was recorded on an Agilent 400 FT-NMR spectrometer (400 MHz). Scanning electron microscopy (SEM) images and energy dispersive spectroscopy (EDX) profiles were collected on a Hitachi SU8030. Samples were activated and coated with OsO4 to ~8 nm thickness in a Denton Desk III TSC Sputter Coater (Moorestown, N.J.) before SEM-EDX analysis. Inductively coupled plasma atomic-emission spectroscopy (ICP-AES) was performed on a computer-controlled (QTEGRA software v. 2.2) Thermo iCap 7600 Duo ICP-OES (Thermo Fisher Scientific, Waltham, Mass., USA) operating in standard mode and equipped with a SPRINT valve and CETAC 520 autosampler (Teladyne CETAC, Omaha, Nebr., USA). OPAA@PCN-128y samples (2-3 mg) were digested in a small amount (1 mL) of a mixture of 3:1 v/v conc. $HNO_3:H_2O_2$ (30 wt % in $H_2O$) by heating in a Biotage (Uppsala, Sweden) SPX microwave reactor (software version 2.3, build 6250) at 150° C. for 5 minutes. The acidic solution was then diluted to a final volume of 15 mL with ultrapure deionized $H_2O$ and analyzed for S (180.731, 182.034, and 182.624 nm) and Zr (339.198, 343.823, and 349.619 nm) content as compared to the standard solutions. The enzymes loading was determined by comparing the experimental Zr:S ratio to the theoretical ratio given by the stoichiometry of Zr in the MOF to the number of methionines and cysteines thiols present in OPAA.

Synthetic Procedures

OPAA Expression.

The OPAA gene utilized was a naturally occurring variant. It differed from previous OPAA entry Q44238.3 by three amino acids at sites 210, 211, and 314. The present gene, which was modified by site-directed mutagenesis, lacked the last 77 carboxyl-terminal amino acids of the OPAA enzyme. This truncated gene was cloned into the NcoI and EcoRI sites of the pSE420 expression vector of *E. coli*. Buffered aqueous solutions of OPAA (0.05-0.2 mg/ml) were prepared at pH of 7.2 (tris-bis propane buffer).

Labeling OPAA with Fluorescent Dye.

AlexaFluor-647 labeled OPAA (OPAA647) was prepared by reacting 0.5 mg OPAA with 1.2 equivalents of an AlexaFluor-647-(ethyl-p-nitrophenyl)-phosphonate conjugate followed by purification of the labeled protein by size-exclusion chromatography (SEC). AlexaFluor-647 was chosen due to the relative insensitivity of its fluorescence intensity and quantum yield to environmental conditions, and excitation/emission maxima (650 nm/665 nm) that occur far outside that of PCN-128 (400 nm/540 nm).

OPAA Immobilization in PCN-128y.

1 mg of activated PCN-128y was added to 1 mL of deionized water and sonicated for 5 min until a uniform suspension was formed. The well dispersed solid was isolated by centrifugation at 15000 rpm for 1 min and the supernatant was decanted. The solid was then suspended in a 1 ml solution of OPAA (0.2 mg/ml) in BTP buffer solution (pH 7.2). The absorbance of the supernatant solution at 280 nm was recorded over 24 h using a NanoDrop 2000 UV-Vis spectrophotometer. After that, the OPAA@PCN-128y composite was isolated by centrifugation at 15000 rpm for 1 min, and the supernatant was removed. The solid was further washed with BTP buffer (pH 7.2) 5 times before further experiments.

Confocal Laser Scanning Microscopy Experiments

Confocal laser scanning microscopy analysis (CLSM) was performed on 10 μm-long PCN-128y crystals to examine the distribution of enzymes throughout the matrix. Fluorescence was examined, applying CLSM on a Leica TCS SP5. The Ar laser was set to 5%. Bit depth was set to 12 to achieve 4096 grey levels intensity resolution. Laser line 633 with 3% laser power was used to visualize AlexaFluor-647 dye labeled OPAA on PCN-128y at different depth along z direction.

Catalytic Activity Experiments

Hydrolysis Activity for DFP.

Hydrolysis profiles of diisopropyl fluorophosphate (DFP) by using free OPAA or immobilized OPAA@PCN-128 were recorded on an Agilent 400 FT-NMR spectrometer (400 MHz) based on the $^{31}P$ NMR spectrum. The $^{31}P$ NMR spectrum for DFP consists of a doublet (−7.62 ppm and −13.69 ppm) due to the phosphorus-fluorine coupling. After the phosphorus-fluorine bond is hydrolyzed by OPAA, the spectrum consists entirely of a downfield singlet from the diisopropylphosphate (−0.95 ppm).[3] For a typical reaction, composite OPAA@PCN-128y (0.1 mg OPAA and 1 mg PCN-128y) was loaded into a 1.5 dram vial. Then 896 μL of BTP buffer (pH 7.2) and 100 μL deuterium water were added, and the reaction mixture was stirred for 1 min to disperse the MOF particles homogeneously, and then 4 μL (22 μmol) of DFP was added and the reaction mixture was swirled for 10 s. The reaction mixture was then transferred to a NMR tube and the spectrum was immediately measured. The first data point was collected 120 s after the start of the reaction. The progress of the reaction was monitored with 1 min increments for 30 min (number of scans=16, delay time=28 s). The degree of completion was assessed by calculating the ratio between integration of the product and the reactant peaks based on $^{31}P$ NMR. (percent conversion=product peak integral/(substrate+product peak integral)×100).

Different Enzyme Loading Test.

Given that 12 wt % is the maximum OPAA loading capacity for PCN-128y, two subsaturated OPAA@PCN0128y composites were prepared by soaking 2 mg PCN-128y in 1 ml buffer solution of 0.1 mg/ml OPAA or 0.2 mg/ml OPAA respectively. The complete immobilization of OPAA was monitored until the concentration of OPAA in supernatant became zero. The two composites containing 0.1 mg OPAA and 0.2 mg OPAA were then isolated by centrifugation and measured in terms of conversion of DFP hydrolysis as described above.

Thermal Stability and Long-Term Stability Test.

For thermal stability, free OPAA or OPAA@PCN-128y composite containing 0.1 mg OPAA was incubated in BTP buffer solution at different temperature, namely 25° C., 35° C., 45° C., 55° C., 70° C., 80° C., and 90° C. for 30 min. For long-term stability, free OPAA was lyophilized into dry powder sample, and OPAA@PCN-128y was isolated by centrifugation into solid sample. Both of them were left in air at room temperature for a different time period, namely 0 days (as-synthesized), 1 day, and 3 days. The stability of above prepared samples were measured in terms of conversion of DFP hydrolysis as described above.

Hydrolysis Activity for GD.

Kinetic constants for soman (GD) was determined by monitoring the release of free fluoride at 25° C. in 50 mM bis-tris-propane buffer, pH 8.0, using a fluoride electrode.

Initial screenings were conducted using a single fixed 3.0 mM substrate concentration. (See, Newmark, J., Arch. Neurol. 2004, 61 (5), 649-652.)

Example 3

This example illustrates the synthesis and characterization of a water-stable csq-net zirconium MOF, NU-1003, featuring the largest mesoporous aperture known for a zirconium MOF to date. By encapsulating OPAA in crystals of 300 nm length, the overall initial turnover rate for the hydrolysis of the nerve agent simulant, diisopropyl fluorophosphate (DFP), and the agent itself, Soman (GD), have been significantly improved. Indeed, the turnover frequencies and overall hydrolysis rates observed for encapsulated OPAA now exceed even those measured for the free enzyme under the same conditions.

Results and Discussion

Synthesis and Characterization of NU-1003.

Example 1 describes the use of a mesoporous zirconium-based MOF, NU-1000, with csq-net topology for enzyme immobilization. Based on the principle of isoreticular design, extending the pore and aperture size in csq-net topology zirconium MOFs should be possible by using longer linkers. However, previous attempts to extend the pore and aperture size of NU-1000 by adding C—C single or triple bonds between neighboring phenyl rings resulted in an isomorphic zirconium MOF with ftw topology. (See, Wang, T. C., et al., Ultrahigh Surface Area Zirconium Mofs and Insights into the Applicability of the Bet Theory. *J. Am. Chem. Soc.* 2015, 137 (10), 3585-3591; Kalidindi, S. B., et al., Chemical and Structural Stability of Zirconium-Based Metal-Organic Frameworks with Large Three-Dimensional Pores by Linker Engineering. *Angew. Chem., Int. Ed.* 2015, 127 (1), 223-228; Gomez-Gualdron, D. A., et al., Computational Design of Metal-Organic Frameworks Based on Stable Zirconium Building Units for Storage and Delivery of Methane. *Chem. Mater.* 2014, 26 (19), 5632-5639.) In order to address this challenge, we designed and synthesized (FIG. 14A) a tetracarboxylate linker L1 based on pyrene. The solvothermal reaction of zirconyl chloride octahydrate with L1 in DMF in the presence of TFA modulator indeed afforded rod-like microcrystals of NU-1003. However, the crystals were too small to obtain an experimental single-crystal structure of NU-1003.

Previously, a method has been developed for obtaining crystal structures from PXRD data by combining in silico construction of MOF structures and simulating their PXRD patterns along with classical force field structural optimization. This method has been used to simulate zirconium MOF structures by using the well-defined $Zr_6(\mu_3\text{-}O)_4(\mu_3\text{-}OH)_4(OH)_4(H_2O)_4$ ($Zr_6$-cluster) node and tetracarboxylate linkers. In accordance with the experimental PXRD pattern for the NU-1003, a P1 structure was found computationally (FIG. 15A). This simulated structure was composed of 8-connected $Zr_6$-cluster nodes and L1 linkers (FIG. 14A) and featured an extended csq-net topology. In comparison, (FIG. 14B) the diameters of the hexagonal pores (44 Å) of NU-1003 were larger than those of previously reported csq-net zirconium MOFs, including the mesoporous MOFs PCN-128 (42 Å) and NU-1000 (32 Å). (See, Mondloch, J. E., et al., Vapor-Phase Metalation by Atomic Layer Deposition in a Metal-Organic Framework. *J. Am. Chem. Soc.* 2013, 135 (28), 10294-10297; Zhang, Q., et al., Piezofluorochromic Metal-Organic Framework: A Microscissor Lift. *J. Am. Chem. Soc.* 2015, 137 (32), 10064-10067.) The side-length of the triangular pores (17 Å) of NU-1003 was also larger than that of PCN-128 (15 Å) and much larger than that of NU-1000 (9 Å). Most importantly, for NU-1003, the size of the windows (12×13 Å) between hexagonal and triangular pores was much larger than both PCN-128 (9×9 Å) and NU-1000 (8×10 Å). These larger micropores and windows between micro- and mesopores (one-dimensional channels) can aid with the diffusive transport of molecular substrate and product after enzyme immobilization selectively in the mesopores of NU-1003. After activation using supercritical drying (SCD) with $CO_2$, the BET area obtained from the measured $N_2$ isotherm (FIG. 15B) for NU-1003 was 2700 $m^2/g$. The calculated DFT pore size distribution (PSD) from the experimental $N_2$ isotherm indicated that there existed both mesopores (between 3.8 to 4.5 nm) and micropores (between 1.3 to 1.7 nm) in NU-1003. It is believed that NU-1003 presents the largest pore aperture among all zirconium MOFs reported to date.

Based on the previously reported method for synthesizing nanocrystals of zirconium MOFs with csq-net topology, hexagonal cylinder shaped NU-1003 crystals were obtained with lengths ranging from 300 nm to 10000 nm (FIGS. 16A-16E), here denoted as NU-1003-size (size=300 nm, 1000 nm, 2000 nm, 7000 nm, and 10000 nm). (See, Li, P., et al. Synthesis of Nanocrystals of Zr-Based Metal-Organic Frameworks with Csq-Net: Significant Enhancement in the Degradation of a Nerve Agent Simulant. *Chem. Commun.* 2015, 51 (54), 10925-10928; Liu, Y., et al., Dual-Function Metal-Organic Framework as a Versatile Catalyst for Detoxifying Chemical Warfare Agent Simulants. *ACS Nano* 2015, 9 (12), 12358-12364.) The bulk-phase PXRD patterns of different sizes of NU-1003 crystals were in excellent agreement with the simulated patterns (FIG. 15F).

Immobilization of OPAA.

To monitor the immobilization process of OPAA in NU-1003, NU-1003-10000 nm crystals were soaked in solution with AlexaFluor-647-tagged OPAA (OPAA647) (FIG. 17A). In-situ confocal laser scanning microscopy (CLSM) images on a single crystal of NU-1003-10000 nm were taken at 2 min, 60 min, 240 min, 960 min, 1440 min, 2880 min, 4320 min, and 7200 min (FIG. 17B). Using the line tool in Image J, fluorescence intensity profiles taken along the middle of an NU-1003-10000 nm crystal with time were obtained and plotted as a function of the length of the crystal (FIG. 17C). The results indicated that the diffusion of OPAA647 was one-dimensional from the two ends toward the center of the NU-1003-10000 nm crystals. To determine the accurate loading capacity of OPAA in NU-1003, the crystals of NU-1003-size (size=300 nm, 1000 nm, 2000 nm, 7000 nm, and 10000 nm) were immersed in an aqueous bis-tris-propane buffer (BTP, pH 7.2) solution of OPAA (0.2 mg/ml) at 25° C. The uptake of OPAA by different sizes of NU-1003 was followed using UV-vis spectroscopy and the maximum loadings of OPAA for different sizes of NU-1003 varied in the range of 0.12-0.20 mg/mg (FIG. 18).

These loading capacities were confirmed by inductively coupled plasma-optical emission spectroscopy (ICP-OES) measurements of Zr (Zr nodes in the MOF) and S (methionine and cysteine residues in OPAA). The loading profiles of OPAA in different sizes of NU-1003 indicated that the loading rate was generally inversely correlated with the size of the NU-1003 crystals, as one would expect for a primarily diffusive process. To compare the activity of OPAA immobilized in different sizes of NU-1003 crystals, sub-saturated (size=300 nm, 1000 nm, 2000 nm, 7000 nm, and 10000 nm) was prepared by using a 0.1 mg/ml initial solution of OPAA (FIG. 18B). After the completion of immobilization (3 days were allowed for all), the solid samples were centrifuged and then washed with BTP buffer solution to remove the OPAA adsorbed only on the surface. Not surprisingly, the $N_2$ adsorption isotherms of OPAA@NU-1003-size (size=300 nm, 1000 nm, 2000 nm, 7000 nm, and 10000 nm) exhibited less $N_2$ uptake than did enzyme-free samples of NU-1003-size (size=300 nm, 1000 nm, 2000 nm, 7000 nm, and 10000 nm). The density functional theory (DFT) pore-size distribution analyses of NU-1003-size and OPAA@NU-1003-size (size=300 nm, 1000 nm, 2000 nm, 7000 nm, and 10000 nm) showed that the pore volumes corresponding to the triangular channels (1.3-1.6 nm) of NU-1003 dropped from 0.20 to 0.15 $cm^3/g$, while the incremental pore volumes corresponding to the hexagonal channels (3.8-4.6 nm) dropped from 0.45 to 0.14 $cm^3/g$ after OPAA immobilization. These results suggest that a large amount of space in the mesopores in NU-1003 was filled by OPAA, while the micropores were relatively unoccupied. Powder X-ray diffraction (PXRD) patterns and scanning electron microscopy (SEM) images of different sizes of NU-1003 after OPAA immobilization confirmed that bulk crystallinity and morphology were retained. To determine the distribution of OPAA in NU-1003-size crystals, SEM with energy dispersive X-ray (EDX) spectroscopy were used to assess the distribution of sulfur along single crystals of NU-1003-size (size=300 nm, 1000 nm, 2000 nm, 7000 nm, and 10000 nm). These measurements confirmed, for the full range of crystallites sizes, that OPAA was evenly dispersed (FIGS. 18C-18F).

Size Effect on Nerve Agent Hydrolysis.

Figure 19A:
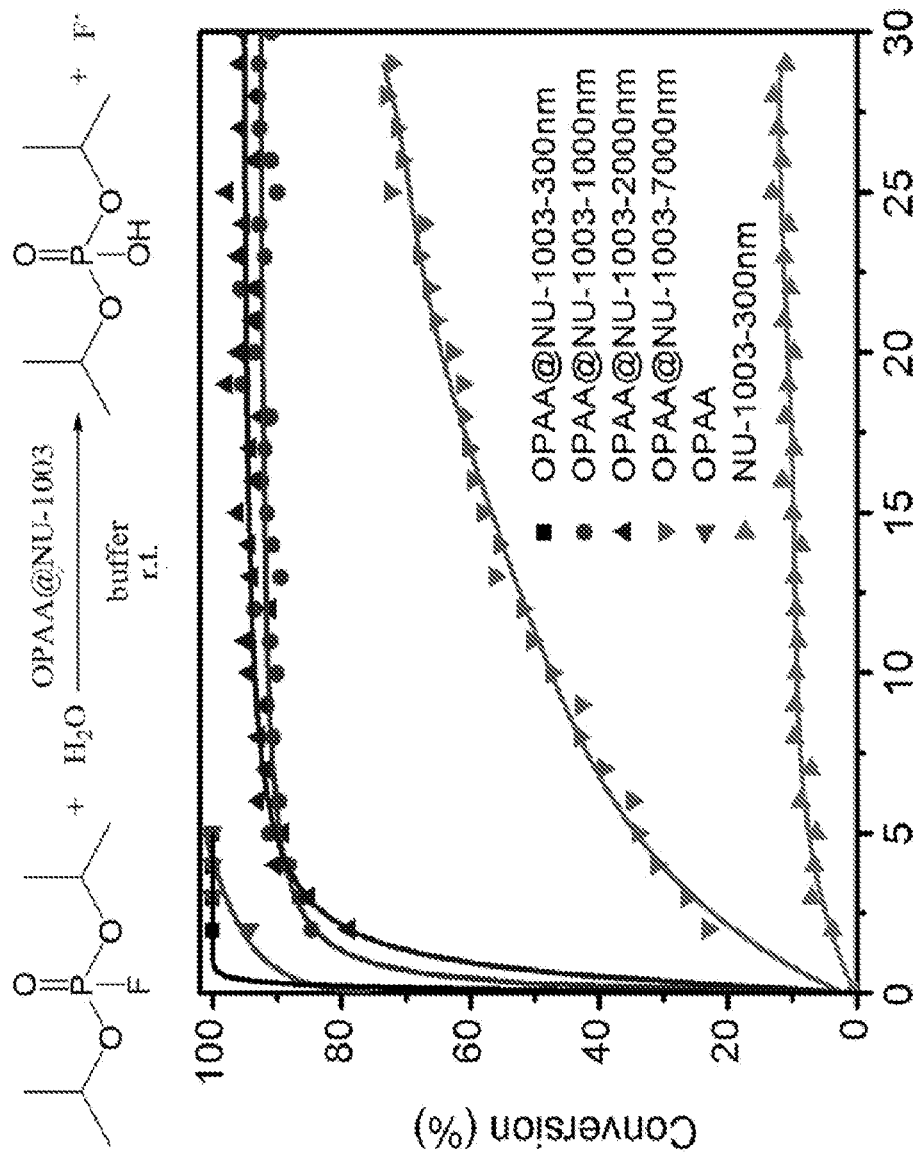
FIG. 19A depicts hydrolysis profiles of DFP catalyzed by different sizes of OPAA@NU-1003.
Figure 19B:
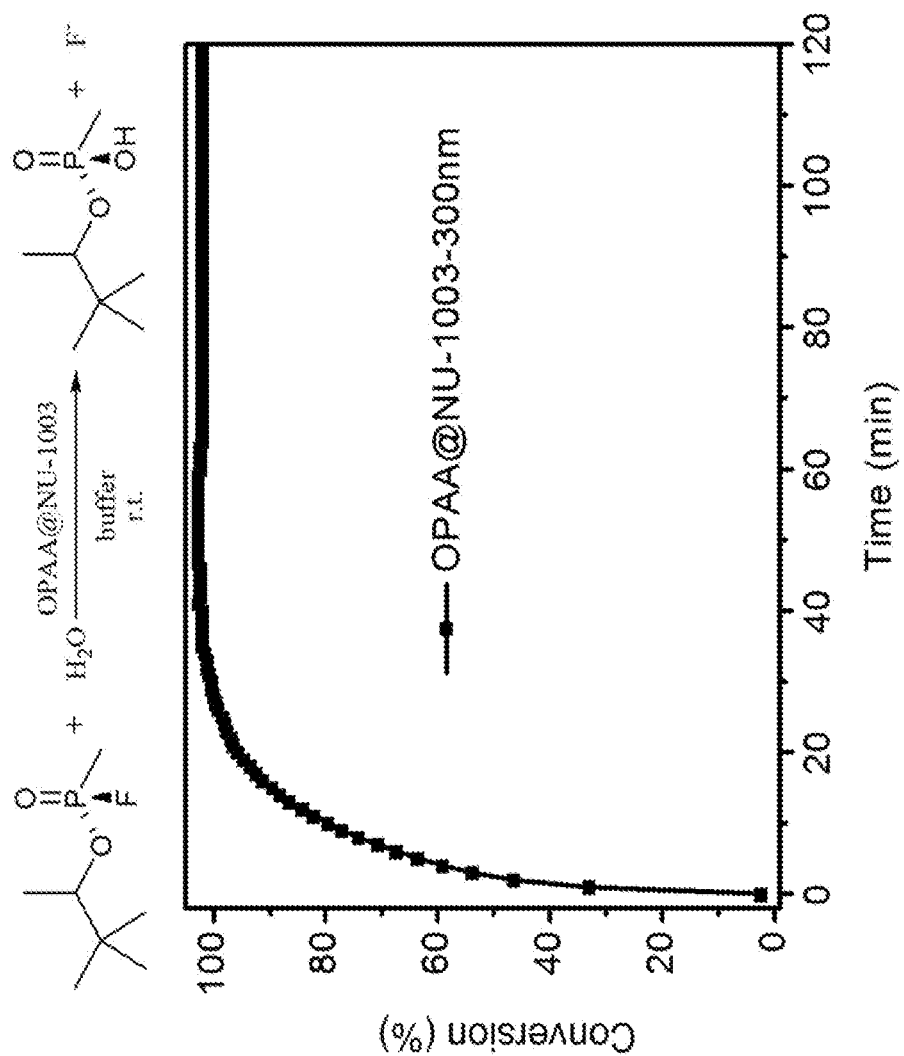
FIG. 19B shows a full hydrolysis curve of GD catalyzed by OPAA@NU-1003-300 nm.
Figure 19C:
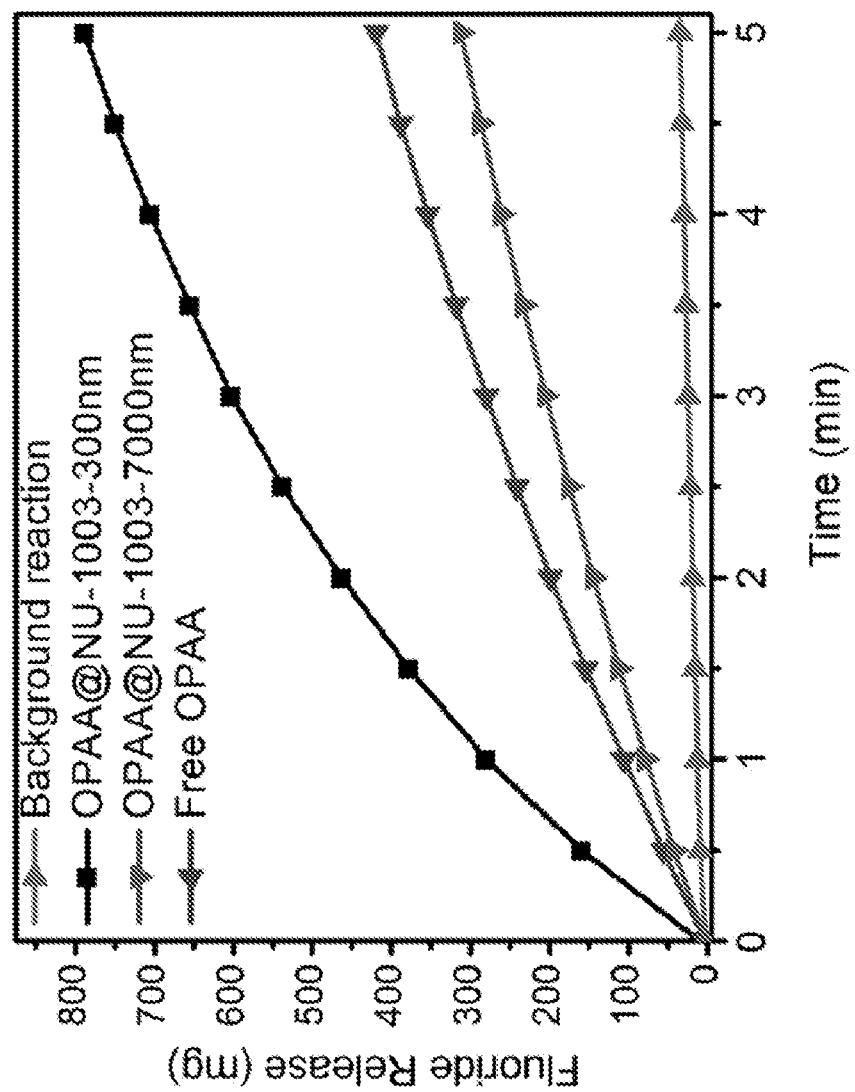
FIG. 19C depicts hydrolysis profiles of GD catalyzed by OPAA@NU-1003-300 nm, OPAA@NU-1003-7000 nm, free OPAA and the background reaction in the first 5 min.
Figure 19D:
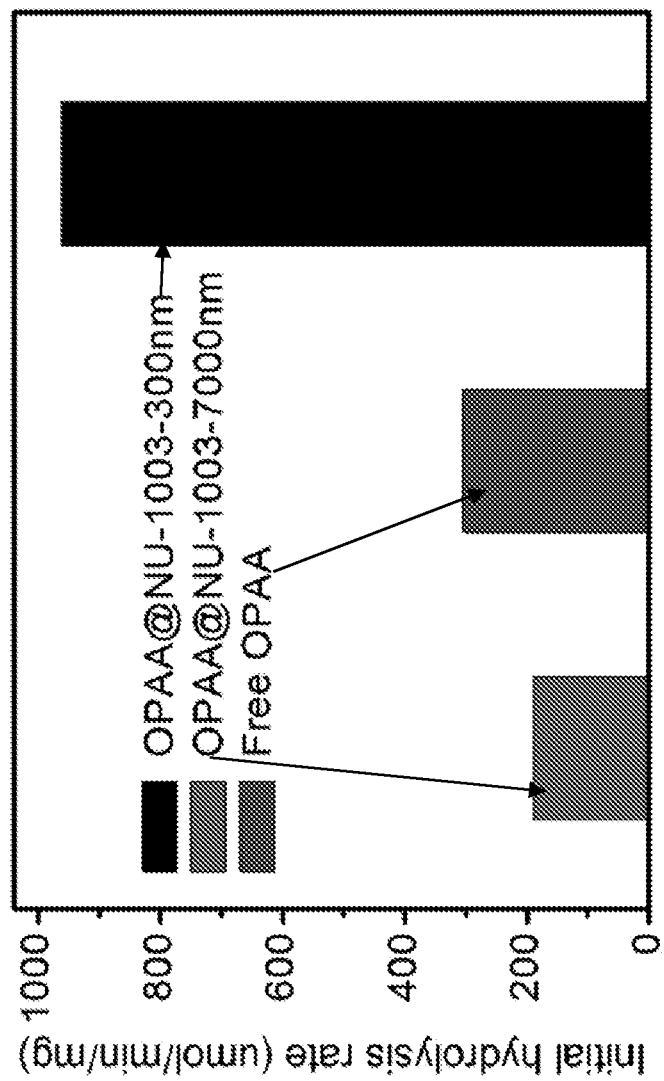
FIG. 19D depicts the initial turnover rate of OPAA@NU-1003-300 nm, OPAA@NU-1003-7000 nm, and free OPAA for hydrolysis of GD.
Figure 20E:
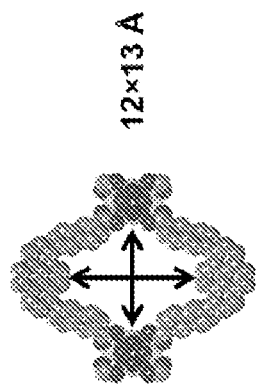
FIG. 20E shows the structure of MOF NU-1003.
Figure 20E:
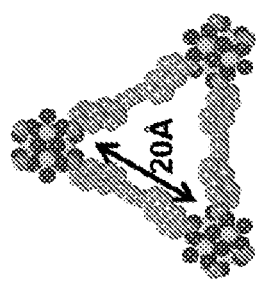
Figure 20E:
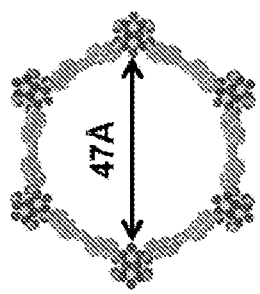
Figure 20E:
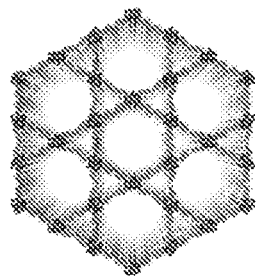
Figure 20F:
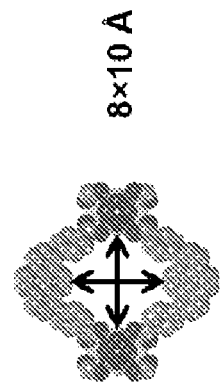
FIG. 20F shows the structure of MOF NU-1000.
Figure 20F:
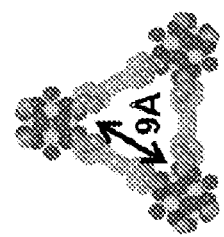
Figure 20F:
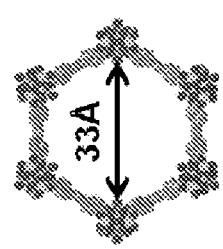
Figure 20F:
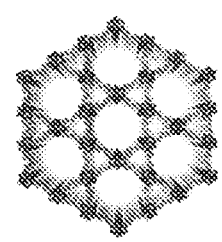

The enzyme activity after immobilization and the effect of particle size on diisopropyl fluorophosphate (DFP) hydrolysis were examined next (FIG. 19A). Although the $Zr_6$-cluster of NU-1003 was identical to those well-studied for nerve agent hydrolysis, at pH 7.2 or lower, NU-1003 did not show catalytic activity for the degradation of DFP. Compared to free OPAA under the same conditions, OPAA@NU-1003-7000 nm showed a much slower initial hydrolysis rate based on the first data point taken at 2 min. Nevertheless, by using smaller particles, NU-1003-2000 nm and NU-1003-1000 nm, the hydrolysis rate was significantly increased and became close to that of free OPAA with the conversion of DFP plateauing at 90%. Importantly, when NU-1003-300 nm was used as the enzyme carrier, the conversion of DFP reached 100% after only 2 min under the same conditions. Encouraged by the fast hydrolysis rate for DFP using OPAA@NU-1003-300 nm, the performance of OPAA@NU-1003-300 nm on a G-type nerve agent Soman (GD) was tested. In BTP pH 7.2 buffer, the degradation of GD catalyzed by OPAA@NU-1003-300 nm was complete after 30 min with an initial half-life of $t_{1/2}$=2 min (FIG. 19B). To accurately compare the initial turnover rate of free OPAA and OPAA@NU-1003-300 nm, the half-life of GD was determined by monitoring the release of free fluoride into the BTP buffer (pH 7.2), using a fluoride electrode (FIG. 19C). As a control, OPAA@NU-1003-7000 nm was also examined. Similar to the findings for DFP hydrolysis, the hydrolysis rate of OPAA@NU-1003-7000 nm (189 µmol/min/mg) was much slower than that of free OPAA (305 µmol/min/mg). Remarkably, the results also indicated that OPAA@NU-1003-300 nm can efficiently defluorinate/deactivate Soman with an initial reaction rate of 961 µmol/min/mg (FIG. 19D), which is more than three times faster than that of free OPAA.

The significantly increased overall turnover rate accompanying the reduction in size of the MOF-based enzyme carrier indicated that the inherent barriers to diffusive permeation of the carrier by molecular reactants and products could be substantially negated by decreasing in-crystal diffusion lengths and thereby rendering a larger fraction of the encapsulated enzyme accessible for catalytic hydrolysis. The finding that OPAA@NU-1003-300 nm catalyzed the hydrolysis of GD at a rate more than three times that of free enzyme may point to a beneficial confinement effect upon the enzyme's intrinsic activity. Alternatively, the enhancement may be indicative of elimination of previously unrecognized residual aggregation (and deactivation) in the solution phase. Regardless, such a large increase is significant as the OPAA enzyme already exhibits the highest reported GD activity of any enzyme known to us.

Finally, it should be noted that BTP buffer was intentionally chosen for the catalysis studies because its pH of 7.2 is close to that of human blood. The obtained results suggest that nanosized OPAA@NU-1003 has potential for use as an injectable antidotal formulation in the human body for highly efficient nerve agent hydrolysis.

CONCLUSIONS

In summary, a water stable zirconium metal-organic framework, NU-1003, has been designed and prepared. This MOF features a csq-net topology and has the largest mesoporous apertures (4.6 nm) known for a zirconium MOF to date. In addition, the size of NU-1003 crystals is tunable from 300 nm to 10000 nm. A nerve agent hydrolyzing enzyme, organophosphorus acid anhydrolase (OPAA), has been studied, and it has been shown that it can be encapsulated in the pores of NU-1003, causing the catalytic efficiency of the immobilized OPAA in the nanosized MOF to be significantly increased compared to that of free OPAA in BTP buffer. This report highlights a method for the highly efficient hydrolysis of a nerve agent using a nanosized enzyme carrier. These nanosized MOF-enzyme carriers could be used as a formulation for in vivo nerve agent degradation in the future.

Methods

Materials.

$ZrOCl_2 \cdot 8H_2O$ (98%), benzoic acid (>99.5%), 1,3,6,8-tetrabromopyrene (97%), diisopropyl fluorophosphate (DFP), bis-tris-propane, potassium hydroxide (90%), potassium phosphate tribasic (>98%), dioxane (>99.0%), and trifluoroacetic acid (99%) were purchased from Sigma-Aldrich. Tetrakis(triphenylphosphine)palladium(0) (99%) was purchased from Strem Chemicals. N,N'-Dimethylformamide (DMF, 99.8%) was obtained from Macron Fine Chemicals. AlexaFluor®647 dye was purchased from Life Technologies (Thermo Fisher Scientific). Methyl 6-(pinacolboryl)-2-naphthoate was synthesized using a published procedure. (See, He, Y., et al., A Robust Doubly Interpenetrated Metal-Organic Framework Constructed from a Novel Aromatic Tricarboxylate for Highly Selective Separation of Small Hydrocarbons. *Chem. Commun.* 2012, 48 (52), 6493-6495.) All chemicals were used without further purification. The gene encoding the OPAA enzyme was originally cloned from *Alteromonas* sp. JD6.5, as described previously. (See, Daczkowski, C. M., et al., Engineering the Organophosphorus Acid Anhydrolase Enzyme for Increased Catalytic Efficiency and Broadened Stereospecificity on Russian Vx. *Biochemistry* 2015, 54 (41), 6423-6433.) GD was obtained from the stocks at the Edgewood Chemical Biological Center and was 95.3+/−1.5% pure by $^{31}P$ NMR, NIST-traceable through an internal triethylphosphate standard.

Physical Methods and Measurements.

Powder X-ray diffraction (PXRD) spectra were collected on a Rigaku model Smartlab diffractometer equipped with a Cu rotating anode X-ray source. $N_2$ sorption isotherm measurements were performed on a Micromeritics Tristar II 3020 (Micromeritics, Norcross, Ga.) at 77 K. $^{31}P$ NMR specta were recorded on an Agilent 400 FT-NMR spectrometer (400 MHz). Scanning electron microscopy (SEM) images and energy dispersive spectroscopy (EDX) profiles were collected on a Hitachi SU8030. Samples were activated and coated with $OsO4$ to ~8 nm thickness in a Denton Desk III TSC Sputter Coater (Moorestown, N.J.) before SEM-EDX analysis. Inductively coupled plasma optical-emission spectroscopy (ICP-OES) was performed on a computer-controlled (QTEGRA software v. 2.2) Thermo iCap 7600 Duo ICP-OES (Thermo Fisher Scientific, Waltham, Mass., USA) operating in standard mode and equipped with a SPRINT valve and CETAC 520 autosampler (Teladyne CETAC, Omaha, Nebr., USA). OPAA@NU-1003 samples (2-3 mg) were digested in a small amount (1 mL) of a mixture of 3:1 v/v conc. $HNO_3:H_2O_2$ (30 wt % in $H_2O$) by heating in a Biotage (Uppsala, Sweden) SPX microwave reactor (software version 2.3, build 6250) at 150° C. for 5 minutes. The acidic solution was then diluted to a final volume of 15 mL with ultrapure deionized $H_2O$ and analyzed for S (180.731, 182.034, and 182.624 nm) and Zr (339.198, 343.823, and 349.619 nm) content as compared to the standard solutions. The enzymes loading is determined by comparing the experimental Zr:S ratio to the theoretical ratio given by the stoichiometry of Zr in the MOF to the number of methionines and cysteines thiols present in OPAA. Confocal laser scanning microscopy images were taken on a Leica TCS SP5. Electrospray ionization mass spectrometry (ESI-MS) data was recorded on a Bruker AmaZon SL Ion Trap at IMSERC (Integrated Molecular Structure Education and Research Center) of Northwestern University.

Synthesis of 1,3,6,8-tetra(6-methoxycarbonylnaphthalen-2-yl)pyrene (L1-OMe)

Dioxane (250 mL) was placed in a 500 mL three-necked round-bottom flask and purged with argon for 1.5 h. With argon purging and the use of a mechanical stirrer, tetrabromopyrene (5.0 g, 9.7 mmol), methyl 6-(pinacolboryl)-2-naphthoate (13.3 g, 42.5 mmol), potassium phosphate tribasic (16.5 g, 77.7 mmol) and tetrakis(triphenylphosphine)-palladium(0) (0.55 g, 0.48 mmol) were added. The reaction was heated to 90° C. for 72 h. The reaction mixture was allowed to cool to room temperature and then 250 mL of water was added. The yellow solid was filtered using a glass Buchner funnel (medium frit) and washed with water (2×500 mL), followed by 500 mL of acetone. The filter flask when then emptied and the solid was collected by passing hot chloroform (6×500 mL) through the fit and collecting the filtrate. Purification by flash column chromatography (silica gel) afforded the product as a light yellow solid (5.28 g, 58%). The product was analyzed by $^1H$-NMR spectroscopy. $^1H$ NMR (500 MHz, $CDCl_3$) δ/ppm=8.71 (s, 4H), 8.25 (s, 4H), 8.21 (s, 2H), 8.19 (s, 4H), 8.14-8.12 (m, 4H), 8.11 (dd, J=5.8, 3.0 Hz, 4H), 7.98-7.94 (m, 4H), 7.92-7.88 (m, 4H), 4.15-3.87 (m, 12H).

Synthesis of 1,3,6,8-tetra(6-carboxynaphthalen-2-yl)pyrene (L1)

L1-Ome (5 g, 5.3 mmol) was added to a 1000 mL single-necked flask and dioxane (250 mL) was then added while stirring. A solution of potassium hydroxide (3.0 g, 53 mmol; 250 mL of water) was added and the reaction mixture was heated to reflux while rigorously stirring for 18 h (at this point, a clear solution was observed). The reaction was allowed to cool down to room temperature. The organic solvent was removed using rotary evaporation and 500 mL of water was added to dissolve the solid obtained. Concentrated HCl was added to the solution dropwise with stirring until the solution reached pH 1. After stirring for an additional hour, the yellow precipitate was collected via centrifugation and washed with water (3×50 mL). The final solid product was recrystallized from DMF, filtered and dried (3.6 g, 68%). The product was analyzed by $^1H$ NMR and $^{13}C$ NMR spectroscopy. $^1H$ NMR (500 MHz, DMSO-$d_6$) δ/ppm=13.16 (s, 4H), 8.75 (s, 4H), 8.41 (s, 4H), 8.35 (d, J=8.5 Hz, 4H), 8.31 (m, 6H), 8.15 (d, J=8.7 Hz, 4H), 8.07 (d, J=8.5 Hz, 4H), 8.01 (d, J=8.4 Hz, 4H). $^{13}C$ NMR (500 MHz, DMSO-$d_6$) δ 167.92 (s), 140.27 (s), 137.23 (s), 135.51 (s), 131.91 (s), 130.84 (s), 130.67 (s), 129.98 (d), 129.69 (s), 129.18 (s), 129.01 (s), 128.29 (s), 126.31 (s), 126.08 (s), 125.85 (s). MS (ESI+) m/z: 881.22 $[M-H]^+$, 882.22 [M], 883.22 $[M+H]^+$.

Synthesis of Different Sizes of NU-1003.

A stock solution A was prepared as follows: $ZrOCl_2.8H_2O$ (200 mg, 0.62 mmol), benzoic acid (2.5 g, 20.5 mmol) and 50 mL of DMF were added into a 250 mL bottle. The solution was heated at 80° C. for 1 h and then allowed to cool down to room temperature. L1 (80 mg, 0.09 mmol) and 50 mL of DMF were added to the 250 ml bottle to form a clear solution.

NU-1003-300 nm:

To a 20 mL portion of stock solution A in an 8-dram vial, 100 μL of TFA (2.94 mmol) was added and the solution sonicated for 10 min. The reaction mixture was placed in an oven at 120° C. for 3 h during which time a light yellow suspension was formed.

NU-1003-1000 nm:

To a 20 mL portion of stock solution A in an 8-dram vial, 200 μL of TFA (5.89 mmol) was added and the solution was sonicated for 10 min. The reaction mixture was then placed in an oven at 120° C. for 3 h during which time a light yellow suspension was formed.

NU-1003-2000 nm:

To a 20 mL portion of stock solution A in an 8-dram vial, 250 μL of TFA (7.40 mmol) was added and the solution was sonicated for 10 min. The reaction mixture was then placed in an oven at 120° C. for 3 h during which time a light yellow suspension was formed.

NU-1003-7000 nm:

To a 20 mL portion of stock solution A in an 8-dram vial, 350 μL of TFA (10.30 mmol) was added and the solution was sonicated for 10 min. The reaction mixture was then placed in an oven at 120° C. for 3 h during which time a light yellow suspension was formed.

NU-1003-10000 nm:

To a 20 mL portion of stock solution A in an 8-dram vial, 500 μL of TFA (14.72 mmol) was added and the solution was sonicated for 10 min. The reaction mixture was then placed in an oven at 120° C. for 3 h during which time a light yellow suspension was formed.

MOF Isolation.

In each case (above), the light yellow suspension was centrifuged for 5 min at 7800 rpm. The solid was then washed with fresh DMF (3×30 mL) before soaking in 40 mL of fresh DMF with 40 μL of TFA for 16 h at room temperature. The sample was subsequently washed with fresh DMF (3×30 mL) and ethanol (3×30 mL).

SCD Activation Procedure.

(See, Farha, O. K., et al., Rational Design, Synthesis, Purification, and Activation of Metal-Organic Framework Materials. *Acc. Chem. Res.* 2010, 43 (8), 1166-1175.) NU-1003 (50 mg) was soaked in absolute ethanol (10 mL), and the soaking solution was replaced 6 times/day for 3 days. The sample was placed inside a supercritical $CO_2$ dryer and the ethanol was exchanged with liquid $CO_2$ over a period of 8 h. The liquid $CO_2$ was purged under positive pressure for three minutes every two hours. The rate of venting of liquid $CO_2$ was always kept below the rate of filling so as to maintain a full drying chamber. After 4 purge cycles, the temperature was raised to 38° C. (i.e., above the critical temperature for carbon dioxide), and the chamber was slowly vented over the course of 15 h at a rate of 0.5 cc/min. The activated MOF was then stored inside an inert-atmosphere glove box until further analysis.

Porosity Measurements.

The SCD-activated MOF material (50-100 mg) was evacuated on a SmartVacPrep instrument (Micromeritics Instrument Corporation, Norcross, Ga., USA) under dynamic vacuum ($10^{-5}$ torr) at room temperature for 7 h followed by 30° C. for 1 hr, 50° C. for 1 hr, 70° C. for 1 hr, and then 80° C. for 15 h. Nitrogen adsorption isotherm measurements were carried out on a Micromeritics Tristar II 3020 (Micromeritics Instrument Corporation) at 77 K. Pore-size distributions were obtained by DFT calculations using a carbon slit-pore model with a $N_2$ kernel.

MOF Purity.

Particle size and phase purity of NU-1003 were characterized using SEM (SU8030, Hitachi) and PXRD (Smartlab, Rigaku).

Labeling OPAA with Fluorescent Dye.

AlexaFluor-647 labeled OPAA (OPAA647) was prepared by reacting OPAA (0.5 mg, 10 nmol) with 1.2 equivalents of an AlexaFluor-647-(ethyl-p-nitrophenyl)-phosphonate conjugate followed by purification of the labeled protein by size-exclusion chromatography (SEC).

OPAA Immobilization in NU-1003.

NU-1003-size (1 mg) (size=300 nm, 1000 nm, 2000 nm, and 7000 nm) was added to 1 mL of deionized water and sonicated for 5 min until a uniform suspension was formed. The well-dispersed solid was isolated by centrifugation at 15000 rpm for 1 min and the supernatant was decanted. The solid was then suspended in a 1 mL solution of OPAA (0.2 mg/mL for saturated samples or 0.1 mg/mL for sub-saturated samples) in BTP buffer solution (pH 7.2). The absorbance of the supernatant solution at 280 nm was recorded over 72 h using a NanoDrop 2000 UV-vis spectrophotometer. The OPAA@NU-1003-size (size=300 nm, 1000 nm, 2000 nm, and 7000 nm) composites were isolated by centrifugation at 15000 rpm for 1 min, and the supernatant was removed. The solid was further washed with BTP buffer (pH 7.2) (5×1 mL) before further experiments.

Catalytic-Reaction Experiments

Hydrolysis Activity for DFP:

Hydrolysis profiles of diisopropyl fluorophosphates (DFP) using free OPAA or immobilized OPAA@NU-1003 were recorded on an Agilent 400 FT-NMR spectrometer (400 MHz) based on the $^{31}P$ NMR spectrum. The $^{31}P$ NMR spectrum for DFP consists of a doublet (−7.62 ppm and −13.69 ppm) due to the phosphorus-fluorine coupling. After the phosphorus-fluorine bond is hydrolyzed by OPAA, the spectrum consists entirely of a downfield singlet from the diisopropylphosphate (−0.95 ppm). For a typical reaction, composite OPAA@NU-1003 (0.1 mg OPAA and 1 mg NU-1003) was loaded into a 1.5 dram vial. Then 896 µL of BTP buffer (pH 7.2) and 100 µL of deuterated water were added, and the reaction mixture was stirred for 1 min to disperse the MOF crystals homogeneously. 4 µL (22 µmol) of DFP was then added and the reaction mixture was swirled for 10 s. The reaction mixture was then transferred to an NMR tube and the $^{31}P$ NMR spectrum was immediately measured; the first data point was collected 120 s after the start of the reaction. The progress of the reaction was monitored with 1 min increments for 30 min (number of scans=16, delay time=28 s). The degree of completion was assessed by calculating the ratio between integration of the product and the reactant peaks in the $^{31}P$ NMR spectra (percent conversion=product peak integral/(substrate+product peak integral)×100).

Hydrolysis Activity for GD.

The reaction rates for Soman (GD) were determined by monitoring the release of free fluoride at 25° C. in 50 mM bis-tris-propane buffer, pH 7.2, using a fluoride electrode with fixed initial 3.0 mM GD concentration.

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more".

The foregoing description of illustrative embodiments of the invention has been presented for purposes of illustration and of description. It is not intended to be exhaustive or to limit the invention to the precise form disclosed, and modifications and variations are possible in light of the above teachings or may be acquired from practice of the invention. The embodiments were chosen and described in order to explain the principles of the invention and as practical applications of the invention to enable one skilled in the art to utilize the invention in various embodiments and with various modifications as suited to the particular use contemplated. It is intended that the scope of the invention be defined by the claims appended hereto and their equivalents.

What is claimed is:

1. An enzyme-immobilizing metal-organic framework compound of comprising:
   a channel-type metal-organic framework compound comprising $Zr_6$ cluster nodes and having a hierarchical pore structure comprising a first set of large channels, a second set of small channels running alongside of the large channels, and openings defined between the large channels and the small channels, the large channels having a larger diameter than the small channels, wherein the channel-type metal-organic framework compound has a csq-net topology in which the large channels have a hexagonal cross-section and the small channels have a triangular cross-section; and
   catalytically active enzymes immobilized in the large channels.

2. The enzyme-immobilizing metal-organic framework compound of claim 1, wherein the smaller channels are free of the catalytically active enzymes.

3. The enzyme-immobilizing metal-organic framework compound of claim 1, wherein the $Zr_6$ cluster nodes are connected by tetratopic organic linkers.

4. The enzyme-immobilizing metal-organic framework compound of claim 3, wherein the tetratopic organic linkers comprise pyrene groups.

5. The enzyme-immobilizing metal-organic framework compound of claim 3, wherein the tetratopic organic linkers comprise parylene groups.

6. The enzyme-immobilizing metal-organic framework compound of claim 3, wherein the tetratopic organic linkers comprise porphyrin groups.

7. The enzyme-immobilizing metal-organic framework compound of claim 1 having an enzyme loading of at least 10 weight percent.

8. An enzyme-immobilizing metal-organic framework compound of comprising:
a channel-type metal-organic framework compound comprising $Zr_6$ cluster nodes and having a hierarchical pore structure comprising a first set of large channels, a second set of small channels running alongside of the large channels, and openings defined between the large channels and the small channels, the large channels having a larger diameter than the small channels, wherein the channel-type metal-organic framework compound has a length in the range from 100 nm to 1000 nm; and
catalytically active enzymes immobilized in the large channels.

9. The enzyme-immobilizing metal-organic framework compound of claim 8, wherein the large channels have diameters in the range from 2 nm to 8 nm, the small channels have side lengths in the range from 0.5 nm to 5 nm, and the openings have heights and widths in the range from 0.5 nm to 3 nm.

10. A method of enzymatically catalyzing a reaction using enzyme-immobilizing metal-organic framework compounds comprising:
channel-type metal-organic framework compound comprising $Zr_6$ cluster nodes and having a hierarchical pore structure comprising a first set of large channels, a second set of small channels running alongside of the large channels, and openings defined between the large channels and the small channels, the large channels having a larger diameter than the small channels, wherein the channel-type metal-organic framework compound has a csq-net topology in which the large channels have a hexagonal cross-section and the small channels have a triangular cross-section; and
catalytically active enzymes immobilized in the large channels of the channel-type metal-organic framework compounds,
the method comprising: exposing the enzyme-immobilizing metal-organic framework compounds to a sample comprising chemical reactants and allowing the immobilized enzymes to catalyze a reaction between the reactants to form one or more reaction products.

11. The method of claim 10, wherein the smaller channels are free of the catalytically active enzymes.

12. The method of claim 10, wherein the $Zr_6$ cluster nodes are connected by tetratopic organic linkers.

13. The method of claim 10, wherein the tetratopic organic linkers comprise pyrene groups.

14. The method of claim 10, wherein the tetratopic organic linkers comprise parylene groups.

15. The method of claim 10, wherein the tetratopic organic linkers comprise porphyrin groups.

16. The method of claim 10, wherein the large channels have diameters in the range from 2 nm to 8 nm, the small channels have side lengths in the range from 0.5 nm to 5 nm, and the openings have heights and widths in the range from 0.5 nm to 3 nm.

17. The method of claim 10, wherein the enzyme-immobilizing metal-organic framework compounds have an enzyme loading of at least 10 weight percent.

18. The method of claim 10, wherein the channel-type metal-organic framework compounds have lengths in the range from 100 nm to 1000 nm.

\* \* \* \* \*